United States Patent [19]

Lok et al.

[11] 4,440,871

[45] Apr. 3, 1984

[54] CRYSTALLINE SILICOALUMINOPHOSPHATES

[75] Inventors: Brent M. Lok, New City; Celeste A. Messina, Ossining; Robert L. Patton, Katonah, all of N.Y.; Richard T. Gajek, New Fairfield, Conn.; Thomas R. Cannan, Valley Cottage; Edith M. Flanigen, White Plains, both of N.Y.

[73] Assignee: Union Carbide Corporation, Danbury, Conn.

[21] Appl. No.: 400,438

[22] Filed: Jul. 26, 1982

[51] Int. Cl.$^3$ .............................................. B01J 27/14
[52] U.S. Cl. ................................................... 502/214
[58] Field of Search ........... 252/435, 437, 430, 455 R; 423/305; 501/80

[56] References Cited

U.S. PATENT DOCUMENTS

| | | | |
|---|---|---|---|
| 2,270,044 | 1/1942 | Fulton et al. ................... | 252/435 X |
| 3,044,954 | 7/1962 | Hirschler ............................ | 252/430 |
| 3,355,246 | 11/1967 | Kuehl .................................... | 23/113 |
| 3,443,892 | 5/1969 | Wacks et al. ....................... | 23/113 |
| 3,649,523 | 3/1972 | Bertolaceni et al. ........... | 252/437 X |
| 3,791,964 | 2/1974 | Kuehl ............................... | 252/435 X |
| 3,867,279 | 2/1975 | Young ............................... | 252/435 X |
| 3,923,883 | 12/1975 | Gaengler et al. ............... | 252/437 X |
| 3,941,871 | 3/1976 | Dwyer et al. ............. | 252/431 N X |
| 4,061,724 | 12/1977 | Grose et al. .................... | 423/339 X |
| 4,118,588 | 10/1978 | Fouquet et al. ..................... | 560/210 |
| 4,158,621 | 6/1979 | Swift et al. ..................... | 252/437 X |
| 4,310,440 | 1/1982 | Wilson et al. .................. | 423/305 X |
| 4,364,839 | 12/1982 | McDaniel .......................... | 252/430 |

FOREIGN PATENT DOCUMENTS

| | | |
|---|---|---|
| 911410 | 10/1972 | Canada . |
| 53-132545 | 11/1978 | Japan .................................. 252/437 |
| 984502 | 2/1965 | United Kingdom . |

OTHER PUBLICATIONS

"Phosphorus Substitution in Zeolite Frameworks", E. M. Flanigen et al., (1971), [Advances in Chemistry Series No. 101–ACS].

Inorganic Chemistry, vol. 10, No. 11, (1971), G. H. Kühl.

*Primary Examiner*—William G. Wright
*Attorney, Agent, or Firm*—Richard G. Miller

[57] ABSTRACT

A novel class of crystalline microporous silicoaluminophosphates is synthesized by hydrothermal crystallization of silicoaluminophosphate gels containing a molecular structure-forming templating agent. The class comprises a number of distinct species, each with a unique crystal structure. The compositions exhibit properties somewhat analogous to zeolitic molecular sieves which render them useful as adsorbent or catalysts in chemical reactions such as hydrocarbon conversions.

38 Claims, 3 Drawing Figures

CRYSTALLINE SILICOALUMINOPHOSPHATES

BACKGROUND OF THE INVENTION

1. Field of the Invention

The present invention relates to a novel class of crystalline microporous silicoaluminophosphates, to the method for their preparation, and to their use as adsorbents and catalysts. These compositions are prepared hydrothermally from gels containing reactive phosphorus, silicon and aluminum compounds and organic templating agents which function in part to determine the course of the crystallization mechanism and hence the structure of the crystalline product.

2. Description of the Prior Art

Molecular sieves of the crystalline aluminosilicate zeolite type are well known in the art and now comprise over 150 species or both naturally occurring and synthetic compositions. In general the crystalline zeolites are formed from corner-sharing $AlO_2$ and $SiO_2$ tetrahedra and characterized by having pore openings of uniform dimensions, having a significant ion-exchange capacity and being capable of reversibly desorbing an adsorbed phase which is dispersed throughout the internal voids of the crystal without displacing any atoms which make up the permanent crystal structure.

Other crystalline microporous compositions which are not zeolitic, i.e. do not contain $AlO_2^-$ tetrahedra as essential framework constituents, but which exhibit the ion-exchange and/or adsorption characteristics of the zeolites are also known. Metal organosilicates which are said to possess ion-exchange properties, have uniform pores and are capable of reversibly adsorbing molecules having molecular diameters of about 6 A or less are reported in U.S. Pat. No. 3,941,871 issued Mar. 2, 1976 to Dwyer et al. Also a pure silica polymorph, silicalite, having molecular sieving properties and a neutral framework containing neither cations nor cation sites is disclosed in U.S. Pat. No. 4,061,724 issued Dec. 6, 1977 to R. W. Grose et al.

The most recently reported class of microporous compositions and the first framework oxide molecular sieves synthesized without silica, are the crystalline aluminophosphate compositions disclosed in U.S. Pat. No. 4,310,440 issued Jan. 12, 1982 to Wilson et al. These materials are formed from $AlO_2$ and $PO_2$ tetrahedra and have electrovalently neutral frameworks as in the case of silica polymorphs. Unlike the silica molecular sieve, silicalite, which is hydrophobic due to the absence of extra-structural cations, the aluminophosphate molecular sieves are moderately hydrophilic, apparently due to the difference in electronegativity between aluminum and phosphorus. Their intracrystalline pore volumes and pore diameters are comparable to those known for zeolites and silica molecular sieves.

Several years ago, when the synthesis of zeolitic aluminosilicates had become established as a significant field for research, a number of attempts by various investigators were made to isomorphously replace a portion of the $SiO_2$ tetrahedra of zeolites with $PO_2$ tetrahedra during the synthesis process. Barrer et al. (J. Chem. Soc. 1965, pgs. 6616-6628) attempted to synthesize the mineral viseite, which contains $AlO_2$, $SiO_2$ and $PO_2$ tetrahedra, by hydrothermal crystallization from reaction mixtures containing silica, phosphorous and aluminum compounds along with the oxides of sodium and/or calcium. Although a number of aluminosilicates and phosphates were formed, no evidence of isomorphous substitution of phosphorus for silicon was found. Wacks et al. (U.S. Pat. No. 3,443,892, issued May 13, 1969) reported the preparation of a faujasite-type zeolite having the formula:

$$0.5\text{-}1.1Na_2O:Al_2O_3 \cdot 0\text{-}0.2P_2O_5:2.3\text{-}3.3SiO_2:0\text{-}7.2H_2O$$

It is not stated whether there was any isomorphous substitution of phosphorus into the zeolite lattice.

Substantial success in preparing zeolite analogues containing phosphorus was reported by Flanigen and Grose, Molecular Sieve Zeolites-I, ACS, Washington, D.C. (1971), using a synthesis technique utilizing gel crystallization involving controlled copolymerization and coprecipitation of all the framework component oxides, aluminate, silicate and phosphate into a relatively homogeneous gel phase, with subsequent crystallization at 80° C. to 210° C. This technique resulted in the production of aluminosilicophosphates with the following types of zeolite frameworks; analcime, chabazite, phillipsite-harmotome, Type A zeolite, Type L zeolite and Type B zeolite, all of which contained significant amounts of phosphorus (5-25 wt.-% $P_2O_5$) incorporated into the crystal framework.

Insofar as is presently known, none of the heretofore synthesized phosphorus-containing zeolite analogues have been utilized commercially.

The substitution of phosphorus for silicon did not appear to impart any beneficial properties to the substituted compositions not possessed by their aluminosilicate analogues with the possible exception that the individual crystals tended to be significantly larger. To the contrary, many of the physical and chemical properties of the phosphorus-substituted analogues were inferior to those of the unsubstituted species. The substitution of phosphorus in the framework structure of a Type L zeolite resulted in approximately a 50% reduction in its adsorption capacity and also a reduction in apparent pore size from about 10 A to 6-7 A. Phosphorus-substituted Type B was not stable toward thermal activation, and several of the cation forms of other of the phosphorus-substituted compositions prepared by Flanigen and Grose were not as stable as their aluminosilicate analogues. There are no known reports on observed differences in catalytic activity resulting from any phosphorus substitution which may have been achieved by prior known techniques.

SUMMARY OF THE INVENTION

There has now been discovered a novel class of silicon-substituted aluminophosphates which are both crystalline and microporous and exhibit properties which are characteristic of both the aluminosilicate zeolites and the more recently discovered aluminophosphates of Wilson et al., supra. Members of this novel class of silicoaluminophosphate materials have a three-dimensional microporous crystal framework structure of $PO_2^+$, $AlO_2^-$ and $SiO_2$ tetrahedral units, and whose essential empirical chemical composition on an anhydrous basis is:

$$mR:(Si_xAl_yP_z)O_2$$

wherein "R" represents at least one organic templating agent present in the intracrystalline pore system: "m" represents the moles of "R" present per mole of $(Si_xAl_yP_z)O_2$ and has a value of from zero to 0.3, the maximum value in each case depending upon the molecular dimensions of the templating agent and the available void volume of the pore system of the particular silicoaluminophosphate species involved, "x", "y" and "z" represent the mole fractions of silicon, aluminum and phosphorus, respectively, present as tetrahedral oxides, said mole fractions being such that they are within the pentagonal compositional area defined by points A B C D and E of the ternary diagram which is FIG. 1 of the drawings, the said points A B C D and E representing the following values for "x", "y" and "z":

| Point | Mole Fraction | | |
|---|---|---|---|
| | x | y | z |
| A | 0.01 | 0.47 | 0.52 |
| B | 0.94 | 0.01 | 0.05 |
| C | 0.98 | 0.01 | 0 01 |
| D | 0.39 | 0.60 | 0.01 |
| E | 0.01 | 0.60 | 0.39 |

When synthesized in accordance with the novel process of the present invention, the minimum value of "m" in the formula above is 0.02. In a preferred sub-class of the silicoaluminophosphates of this invention, the values of "x", "y" and "z" in the formula above are confined to those within the pentagonal compositional area defined by the points a b c d and e of the ternary diagram which is FIG. 2 of the drawings, the said points a b c d and e representing the following values for "x", "y" and "z":

| Point | Mole Fraction | | |
|---|---|---|---|
| | x | y | z |
| a | 0.02 | 0.49 | 0.49 |
| b | 0.25 | 0.37 | 0.38 |
| c | 0.25 | 0.48 | 0.27 |
| d | 0.13 | 0.60 | 0.27 |
| e | 0.02 | 0.60 | 0.38 |

The term "essential empirical chemical composition" is meant to include the crystal framework and can include any organic templating agent present in the pore system, but does not include alkali metal or other cations which can be present by virtue of being contained in the reaction mixture or as a result of post-synthesis ion-exchange. Such cation species, when present, function as charge-balancing ions for $AlO_2^-$ tetrahedra not associated with a $PO_2^+$ tetrahedron or an organic ion derived from the organic templating agent. Thus, for example, in the preparation of SAPO-20 disclosed hereinafter in Example 28, sodium aluminate was employed as the source of aluminum in the reaction mixture, and accordingly the as-synthesized SAPO-20 product was found to contain 0.5 moles $Na_2O$ per mole of $Al_2O_3$ in addition to 0.3 moles $(TMA)_2O$ per mole of $Al_2O_3$. The overall composition of the as-synthesized SAPO-20, calculated using the chemical analysis data and expressed in terms of molar oxide ratios was:

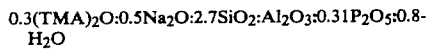

0.3(TMA)$_2$O:0.5Na$_2$O:2.7SiO$_2$:Al$_2$O$_3$:0.31P$_2$O$_5$:0.8-H$_2$O

The essential empirical as-synthesized formula on an anhydrous basis is, however:

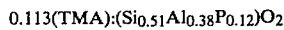

0.113(TMA):(Si$_{0.51}$Al$_{0.38}$P$_{0.12}$)O$_2$ using the aforementioned formula form of

$$mR:(Si_xAl_yP_z)O_2$$

This essential empirical as-synthesized formula is readily computed from the molar oxide ratio expression in which the components R(TMA), Si, Al and P are present in the molar ratio of:

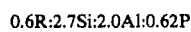

0.6R:2.7Si:2.0Al:0.62P

The sum (Si+Al+P)=(2.7+2.0+0.62)=5.32 is normalized to (Si+Al+P)=1.00 by dividing each term by 5.32, thusly: m=(0.6/5.32)=0.113; x=(2.7/5.32)=0.51; y=(2.0/5.32)=0.38; and z=(0.62/5.32)=0.12.

The aforesaid novel silicoaluminophosphates are synthesized by hydrothermal crystallization from a reaction mixture containing reactive sources of silica, alumina and phosphate, an organic templating, i.e., structure-directing, agent, preferably a compound of an element of Group VA of the Periodic Table, and optionally an alkali metal.

The reaction mixture is placed in a sealed pressure vessel, preferably lined with an inert plastic material such as polytetrafluoroethylene and heated, preferably under autogenous pressure at a temperature of at least about 100° C., and preferably between 100° C. and 250° C., until crystals of the silicoaluminophosphate product are obtained, usually a period of from 2 hours to 2 weeks. The product is recovered by any convenient method such as centrifugation or filtration.

IN THE DRAWINGS

DETAILED DESCRIPTION OF THE INVENTION

Figure 1:
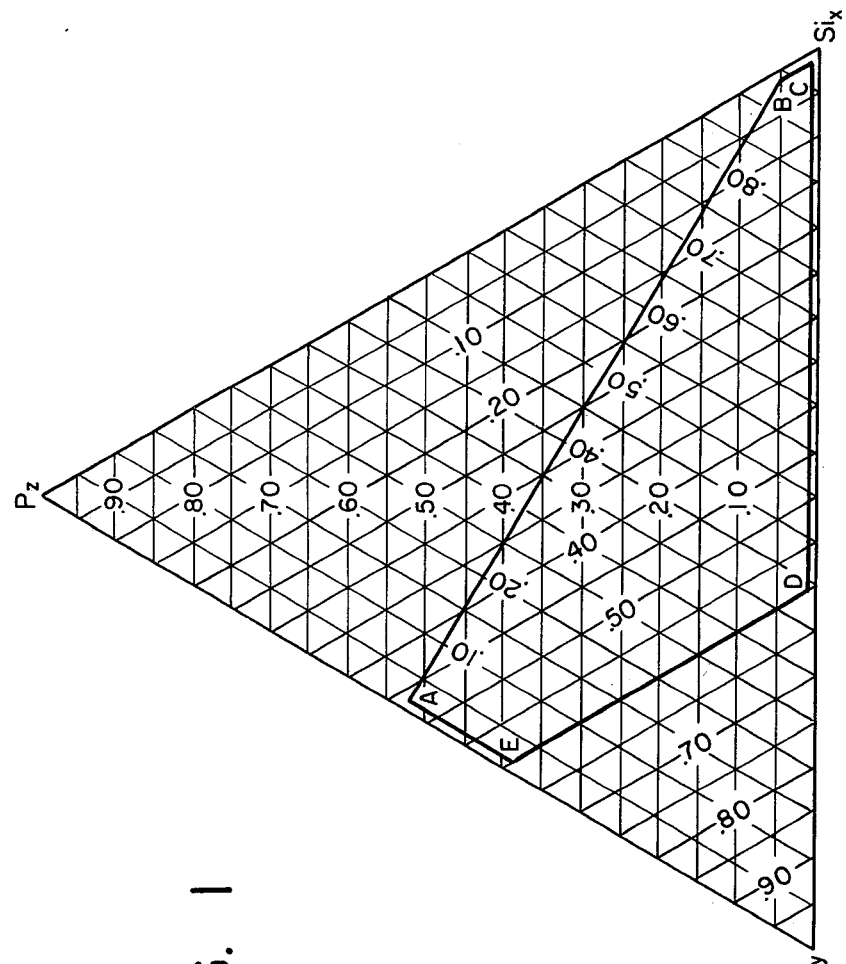
FIG. 1 is a ternary diagram showing the compositional parameters of the silicoaluminophosphates of this invention in terms of mole fractions of silicon, aluminum and phosphorous.

In synthesizing the SAPO compositions of the present invention, it is preferred that the reaction mixture be essentially free of alkali metal cations, and accordingly a preferred reaction mixture composition expressed in terms of molar oxide ratios is as follows:

$$aR_2O:(Si_xAl_yP_z)O_2:bH_2O$$

wherein "R" is an organic templating agent: "a" has a value great enough to constitute an effective concentration of "R" and is within the range of >0 to 3; "b" has a value of from zero to 500, preferably 2 to 30; "x", "y" and "z" represent the mole fractions, respectively of silicon, aluminum and phosphorus in the $(Si_xAl_yP_z)O_2$ constituent, and each has a value of at least 0.01. In this expression the reaction mixture composition is normalized with respect to a total of (Si+Al+P)=(x+y+z)=1.00 mole, whereas in many of the working examples appearing hereinafter the reaction mixtures are expressed in terms of molar oxide ratios normalized to 1.00 mole of $Al_2O_3$. The procedure for converting this latter form to the former is the same as that illustrated hereinabove for the product compositions. Thus, for example, in a reaction mixture expressed in terms of molar oxide ratios as

the molar ratios of Si, Al and P are

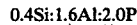

and $(Si+Al+P)=4.0$. the mole fractions of x, y and z are thus computed by dividing each coefficient by 4.0 resulting in:

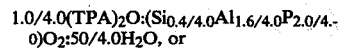

When alkali metal cations are optionally present in the reaction mixture it is preferred to form an aluminophosphate gel, or at least an aluminophosphate protogel, by admixing at least a portion of each of the aluminum and phosphorus sources in the substantial absence of the silicon source so that the procedure is avoided whereby the phosphorus source is added to a highly basic aluminosilicate gel, as was done in most of the prior art attempts to substitute isomorphously $PO_2$ tetrahedra for $SiO_2$ tetrahedra in known zeolite structures. Although the reaction mechanism is by no means clear at this time, it appears that the templating function of the organic species favors the incorporation of $PO_2$ and $AlO_2$ tetrahedra in the framework structures of the crystalline products with $SiO_2$ tetrahedra isomorphously replacing $PO_2$ tetrahedra. This is consistent with the present finding that several of the new silicoaluminophosphate compositions appear to be structurally related to prior known $AlPO_4$ compositions for which there are no known aluminosilicate structural analogues. Moreover, certain of the known zeolites which have structures similar to certain of the present silicoaluminophosphates also have structural counterparts among the known $AlPO_4$ materials. Still further, in at least one instance in which two compositions having similar X-ray diffraction patterns, one being prepared in the organic-containing system of the present invention and the other being prepared in an alkali metal-containing system free of an organic templating agent, it is found that the hydrothermal and thermal stability of the two phases is not at all the same, the former being substantially more stable. Whether this is an indication of fundamental structural difference or simply a difference in the degree of defect structure has not yet been determined. It is quite apparent, however, that the presence of the organic templating agent in the reaction mixture, and consequently in the as-synthesized composition, is highly beneficial both with respect to enabling the production of a much larger number of different structures and in enhancing their physical and chemical properties.

Figure 3:
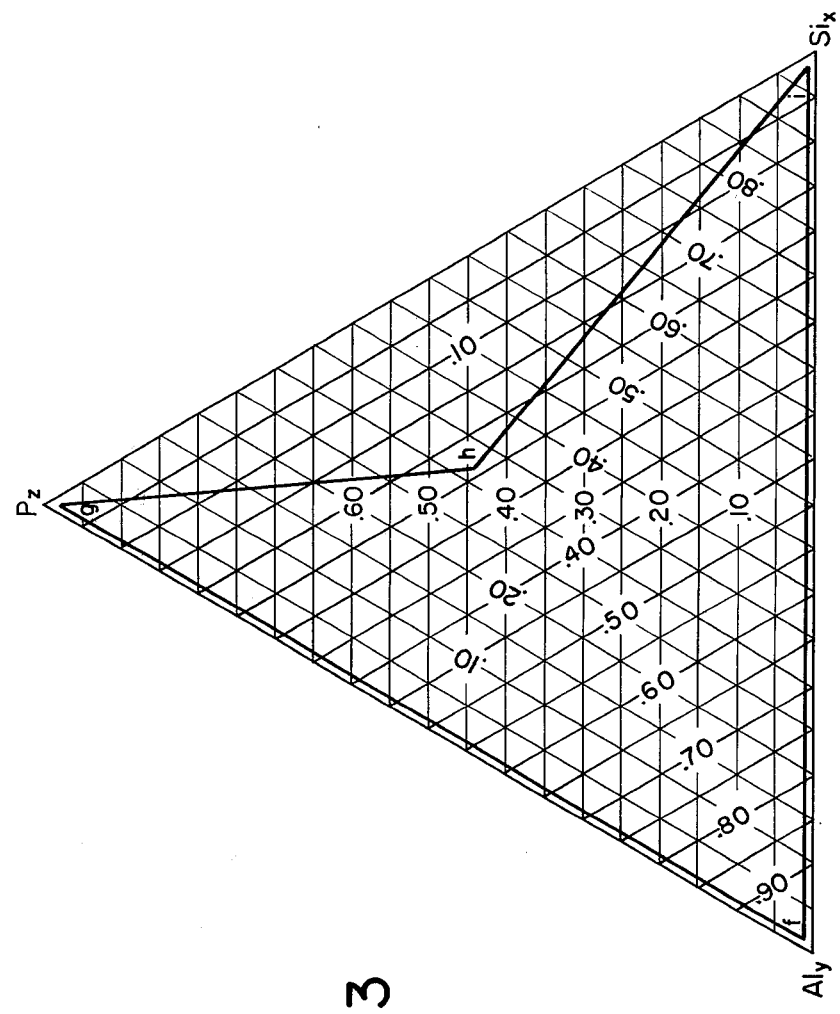
FIG. 3 is a ternary diagram showing the compositional parameters of the reaction mixtures used to prepare the silicoaluminophosphates of this invention in terms of mole fractions of silicon, aluminum and phosphorous.

In any event, the preferred synthesis procedure when alkali metals are not excluded from the reaction mixture is to prepare a reaction mixture having a composition expressed in terms of molar oxide ratios as follows:

$$aR_2O:bM_2O:(Si_xAl_yP_z)O_2:cH_2O$$

wherein "R" is an organic templating agent; "a" has a value great enough to constitute an effective concentration of "R" and is within the range >0 to 3; "M" is an alkali metal; "b" has a value of zero to 2.5; "c" has a value of from zero to 500, preferably 2 to 30; "x", "y" and "z" represent the mole fractions, respectively, of silicon, aluminum and phosphorus in the $(Si_xAl_yP_z)O_2$ constituent, and each has a value of at least 0.01 and being within the quadrilateral compositional area defined by points f g h and i which is FIG. 3 of the drawings, the said points f g h and i representing the following values for "x", "y" and "z":

| Point | Mole Fraction | | |
|---|---|---|---|
| | x | y | z |
| f | 0.01 | 0.98 | 0.01 |
| g | 0.01 | 0.01 | 0.98 |
| h | 0.32 | 0.24 | 0.44 |
| i | 0.98 | 0.01 | 0.01; | said reaction mixture having been formed by combining at least a portion of each of the aluminum and phosphorous sources in the substantial absence of the silicon source and thereafter combining the resulting mixture with the remaining constituents to form the complete reaction mixture.

Although alkali metal silicates can be employed as the silica source in reaction gels to produce certain of the present SAPO compositions, the high alkali metal content and concomitant high pH conditions necessarily imparted to gels where high molar $SiO_2/Al_2O_3$ ratios are desired, results in a marked tendency to produce extraneous aluminophosphates which appear to be dense, i.e., non-microporous, compositions. While the high pH conditions can be avoided by the in situ neutralization of the alkali with an acid and the consequent formation of a precipitated silica, this is, in effect, the use of silica as a reagent rather than an alkali metal silicate. Accordingly it is preferred that if alkali metal silicate is employed as a reagent, it is used in conjunction with a form of silica and is a minor proportion of the overall silica source. In that event, the reaction mixture should have the same composition expressed in terms of mole ratios of oxides as set forth hereinabove when alkali metals are not excluded, and in addition comply with the proviso that at least the major source of silica be a form of silica with the alkali metal silicate comprising a minor proportion, i.e., less than half, of the silica source.

In forming the reaction mixture from which the present silicoaluminophosphates are crystallized the organic templating agent can be any of those heretofore proposed for use in the synthesis of conventional zeolitic aluminosilicates and microporous aluminophosphates. In general these compounds contain elements of Group VA of the Periodic Table of Elements, particularly nitrogen, phosphorus, arsenic and antimony, preferably N or P and most preferably N, which compounds also contain at least one alkyl or aryl group having from 1 to 8 carbon atoms. Particularly preferred nitrogen-containing compounds for use as templating agents are the amines and quaternary ammonium compounds, the latter being represented generally by the formula $R_4N^+$ wherein each R is an alkyl or aryl group containing from 1 to 8 carbon atoms. Polymeric quaternary ammonium salts such as [(C$_{14}$H$_{32}$N$_2$)(OH)$_2$]$_x$ wherein "x" has a value of at least 2 are also suitably employed. Both mono-, di and tri-amines are advantageously utilized, either alone or in combination with a quaternary ammonium compound or other templating compound. Mixtures of two or more templating agents can either produce mixtures of the desired silicoaluminophosphates or the more strongly directing templating species may control the course of the reaction with the other templating species serving primarily to establish the pH conditions of the reaction gel. Representative templating agents include tetramethylammonium, tetraethylammonium, tetrapropylammonium or tetrabutylammonium ions; di-n-propylamine, tripropylamine, triethylamine; triethanolamine; piperidine; cyclohexylamine; 2-methylpyridine; N,N-dimethylbenzylamine; N,N-diethylethanolamine; dicyclohexylamine; N,N-dimethylethanolamine; choline; N,N'-dimethylpiperazine; 1,4-diazabicyclo(2,2,2)octane; N-methyldiethanolamine, N-methylethanolamine; N-methylpiperidine; 3-methylpiperidine; N-methylcyclohexylamine; 3-methylpyridine; 4-methylpyridine; quinuclidine; N,N'-dimethyl-1,4-diazabicyclo(2,2,2)octane ion; di-n-butylamine, neopentylamine; di-n-pentylamine; isopropylamine; t-butylamine; ethylenediamine; pyrrolidine; and 2-imidazolidone. As will be readily apparent from the illustrative Examples set forth hereinafter, not every templating agent will direct the formation of every species of silicoaluminophosphate (SAPO), i.e. a single templating agent can, with proper manipulation of the reaction conditions, direct the formation of several SAPO compositions, and a given SAPO composition can be produced using several different templating agents.

Though not necessary, alkali metal usually introduced as the hydroxides, may facilitate the crystallization of particular SAPO phases. Ordinarily when such cations as Na$^+$, or K$^+$ are present in the reaction gels, these cations also appear in the SAPO products, either as merely occluded (extraneous) compounds or, as stated hereinbefore, as structural cations balancing net negative charges at various sites in the crystal lattice if such should happen to exist. It will be understood that although the essential empirical chemical formulae for the SAPO compositions do not specifically recite such constituents, it is not intended that they be excluded in the same sense that hydrogen cations and/or hydroxyl groups are not specifically provided for in the conventional empirical formulae of zeolitic aluminosilicates.

The most suitable phosphorus source yet found for the present process is phosphoric acid, but organic phosphates such as triethyl phosphate have been found satisfactory, and so also have crystalline or amorphous aluminophosphates such as the AlPO$_4$ composition of U.S. Pat. No. 4,310,440. Organo-phosphorus compounds, such as tetrabutylphosphonium bromide do not, apparently, serve as reactive sources of phosphorus, but these compounds do function as templating agents. Conventional phosphorus salts such as sodium metaphosphate, may be used, at least in part, as the phosphorus source, but are not preferred.

The preferred aluminum source is either an aluminum alkoxide, such as aluminum isopropoxide, or pseudoboehmite. The crystalline or amorphous aluminophosphates which are a suitable source of phosphorus are, of course, also suitable sources of aluminum. Other sources of alumina used in zeolite synthesis, such as gibbsite, sodium aluminate and aluminum trichloride, can be employed but are not preferred.

Silica is preferably introduced into the reaction system as either a silica sol or as fumed silica, but other conventional sources of silica used in zeolite synthesis procedures can be employed, for example, a reactive solid amorphous precipitated silica, silica gel, alkoxides of silicon, silicic acid or alkali metal silicate, the last two named being not preferred.

While not essential to the synthesis of SAPO compositions, it has been found that in general stirring or other moderate agitation of the reaction mixture and/or seeding the reaction mixture with seed crystals of either the SAPO species to be produced or a topologically similar aluminophosphate or aluminosilicate composition, facilitates the crystallization procedure.

After crystallization the SAPO product is isolated and advantageously washed with water and dried in air. The as-synthesized SAPO contains within its internal pore system at least one form of the templating agent employed in its formation. Most commonly the organic moiety is an occluded molecular species, but it is possible, steric considerations permitting, that at least some of the templating agent is present as a charge-balancing cation as is commonly the case with as-synthesized zeolites prepared from organic-containing systems. As a general rule the templating agent, and hence the occluded organic species, is too large to move freely through the pore system of the SAPO product and must be removed by calcining the SAPO at temperatures of 200° C. to 700° C. to thermally degrade the organic species. In a few instances the pores of the SAPO product are sufficiently large to permit transport of the templating agent, particularly if the latter is a small molecule, and accordingly complete or partial removal thereof can be accomplished by conventional desorption procedures such as carried out in the case of zeolites. It will be understood that the term "as-synthesized" as used herein and in the claims does not include the condition of the SAPO phase wherein the organic moiety occupying the intracrystalline pore system as a result of the hydrothermal crystallization process has been reduced by post-synthesis treatment such that the value of "m" in the composition formula

$$mR.(Si_xAl_yP_z)O_2$$

has a value of less than 0.02. The other symbols of the formula are as defined hereinabove. In those preparations in which an aluminum alkoxide is employed as the source of aluminum, the corresponding alcohol is necessarily present in the reaction mixture since it is a hydrolysis product of the alkoxide. It has not been determined whether this alcohol participates in the syntheses process as a templating agent. For the purposes of this application, however, this alcohol is arbitrarily omitted from the class of templating agents, even if it is present in the as-synthesized SAPO material.

Since the present SAPO compositions are formed from AlO$_2$, PO$_2$ and SiO$_2$ tetrahedral units which, respectively, have a net negative charge, a net positive charge and electrical neutrality, the matter of cation exchangeability is considerably more complicated than in the case of zeolitic molecular sieves in which, ideally, there is a stoichiometric relationship between AlO$_2$ tetrahedra and charge-balancing cations. In the SAPO compositions, an AlO$_2$$^-$ tetrahedron can be balanced electrically either by association with a PO$_2$$^+$ tetrahedron or a simple cation such as an alkali metal cation or an organic cation derived from the templating agent, or both. It has also been postulated that non-adjacent $AlO_2^-$ and $PO_2^+$ tetrahedral pairs can be balanced by $Na^+$ and $OH^-$ respectively (Flanigen and Grose, supra). The apparent departure from the Loewenstein rule [W. Loewenstein, Am. Mineral, 39, 92-6(1954)] in such SAPO species as those having compositions in the near proximity of the line D-E in the ternary diagram of FIG. 1 may simply be attributed to inadequate analytical capabilities, or may reflect more fundamental considerations such as the presence of $(H_3O_2)^-$ tetrahedral units which are not taken into account in the composition formulae.

In any event, all of the SAPO compositions of the present invention examined to date have exhibited cation-exchange capacity, in some cases to a significant degree, when analyzed using ion-exchange techniques heretofore employed with zeolitic aluminosilicates. All have uniform pore diameters which are inherent in the lattice structure of each species and which are at least about 3 A in diameter. Ion exchange is ordinarily possible only after the organic moiety present as a result of synthesis has been removed from the pore system. Dehydration to remove water present in the as-synthesized SAPO compositions can usually be accomplished, to some degree at least, in the usual manner without removal of the organic moiety, but the absence of the organic species greatly facilitates adsorption and desorption procedures. As illustrated hereinafter, the SAPO materials have various degrees of hydrothermal and thermal stability, some being quite remarkable in this regard, and function well as molecular sieve adsorbents and hydrocarbon conversion catalysts or catalyst bases.

The invention is illustrated by the following Examples:

EXAMPLE 1

(Preparation of SAPO-5)

A reaction mixture was prepared by combining 7.69 grams of 85 wt.% orthophosphoric acid ($H_3PO_4$) and 33.29 grams of water, to which was added 4.58 grams of a hydrated aluminum oxide, (a pseudo-boehmite phase, 74.2 wt.% $Al_2O_3$, 25.8 wt.% $H_2O$), and stirred until homogeneous. To this mixture was first added 1.08 grams of 37 wt.% HCl, and then 2.16 grams of a fumed silica (92.8 wt.% $SiO_2$, 7.2 wt.% $H_2O$) and the mixture stirred until homogeneous. Finally there was added 16.30 grams of an aqueous solution of 40 wt.% tetraethylammonium hydroxide (TEAOH) and the mixture stirred until homogeneous. The composition of the final reaction mixture in molar oxide ratios was:

$$Al_2O_3:P_2O_5:0.665(TEA)_2O:SiO_2:0.33HCl:80H_2O$$

in terms of molar proportions in which the silicon, aluminum and phosphorus sources are expressed as $TO_2$, i.e., $(Si_xAl_yP_z)O_2$ units, the reaction mixture can be expressed as:

$$0.27(TEA):(Si_{0.20}Al_{0.40}P_{0.40})O_2:16H_2O$$

A portion of this reaction mixture was sealed in a stainless steel pressure vessel lined with polytetrafluoroethylene and heated in an oven at 150° C. at autogenous pressure for 168 hours. The solid reaction product was recovered by filtration, washed with water, and dried in air overnight at room temperature. The composition of the as-synthesized solid product was determined in accordance with the law of mass balance using data from the chemical analysis of the mother liquor, specifically:

| | |
|---|---|
| $Al_2O_3$ | 0.94 mgs./ml |
| $P_2O_5$ | 24.6 mgs./ml |
| $SiO_2$ | 1.11 mgs./ml |
| $Na_2O$ | 0.15 mgs./ml |
| C | 65 mgs./ml |
| N | 9.3 mgs./ml |
| Cl | 7.2 mgs./ml |

The $(TEA)_2O$ content was calculated from the carbon analysis, and the $H_2O$ content was determined by difference. The as-synthesized composition, denominated SAPO-5, thus had a chemical composition (anhydrous basis):

$$0.05(TEA).(Si_{0.22}Al_{0.45}P_{0.33})O_2$$

The chemical composition in terms of mole ratios of oxides was:

$$0.985Al_2O_3:0.716P_2O_5:0.97SiO_2:0.109(TEA)_2O.$$

A portion of the solids was analyzed chemically and found to contain 6.9 wt.-% C, 1.0 wt.-% N, 16.3 wt.-% $SiO_2$, 28.9 wt.-% $Al_2O_3$, 38.3 wt.-% $P_2O_5$ and 14.4 wt.-% LOI, giving a product compositon in molar oxide ratios of:

$$1.0Al_2O_3:0.95P_2O_5:0.96SiO_2:0.13(TEA)_2O:0.8H_2O$$

which corresponds to the formula (anhydrous basis):

$$0.053(TEA).(Si_{0.2}Al_{0.41}P_{0.39})O_2$$

The x-ray powder diffraction pattern of the SAPO-5 product was characterized by the following data:

TABLE A

| 2θ | d | 100 × I/I₀ |
|---|---|---|
| 7.5 | 11.8 | 100 |
| 12.9 | 6.86 | 12 |
| 15.0 | 5.91 | 26 |
| 19.9 | 4.46 | 61 |
| 21.1 | 4.21 | 53 |
| 22.45 | 3.96 | 77 |
| 24.8 | 3.59 | 5 |
| 26.0 | 3.43 | 30 |
| 29.1 | 3.07 | 17 |
| 30.15 | 2.96 | 19 |
| 33.65 | 2.66 | 5 |
| 34.65 | 2.59 | 16 |

This x-ray pattern and all other x-ray patterns appearing hereinafter were obtained using standard X-ray powder diffraction techniques. The radiation source was a high-intensity, copper target, X-ray tube operated at 50 Kv and 40 ma. The diffraction pattern from the copper $K\alpha$ radiation and graphite monochromator is suitably recorded by an X-ray spectrometer scintillation counter, pulse height analyzer and strip chart recorder. Flat compressed powder samples are scanned at 2° (2 theta) per minute, using a two second time constant. Interplanar spacings (d) in Angstrom units are obtained from the position of the diffraction peaks expressed as 2θ where θ is the Bragg angle as observed on the strip chart. Intensities were determined from the heights of diffraction peaks after subtracting background, "$I_o$" being the intensity of the strongest line or peak, and "I" being the intensity of each of the other peaks.

As will be understood by those skilled in the art the determination of the parameter 2 theta is subject to both human and mechanical error, which in combination, can impose an uncertainty of about ±0.4° on each reported value of 2 theta. This uncertainty is, of course, also manifested in the reported values of the d-spacings, which are calculated from the 2 theta values. This imprecision is general throughout the art and is not sufficient to preclude the differentiation of the present crystalline materials from each other and from the compositions of the prior art. In some of the X-ray patterns reported, the relative intensities of the d-spacings are indicated by the notations vs, s, m, w and vw which represent very strong, strong, medium, weak and very weak, respectively.

EXAMPLE 2

(Preparation of SAPO-5)

(a) A reaction mixture was prepared by combining 11.50 grams of 85 wt.% orthophosphoric acid ($H_3PO_4$) and 1.37 grams of a hydrated aluminum oxide (a pseudo-boehmite phase, 74.2 wt.% $Al_2O_3$, 25.8 wt.% $H_2O$) and stirring until homogeneous. To this mixture was added slowly and with stirring 88.50 grams of an aqueous solution of 23 wt.% tetra-n-propyl-ammonium hydroxide (TPAOH). Lastly there was added 71.30 grams of an aqueous silica gel containing 33.7 wt.% $SiO_2$, and the mixture stirred until homogeneous. The composition of the final reaction mixture in molar oxide ratios was:

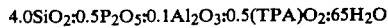

4.0$SiO_2$:0.5$P_2O_5$:0.1$Al_2O_3$:0.5(TPA)$_2$O:65$H_2O$

A portion of the reaction mixture was sealed in a stainless steel pressure vessel lined with polytetrafluorethylene and heated in an oven at 200° C. at autogenous pressure for 168 hours. The solid reaction product was separated and recovered by centrifugation and filtering, suspending in water and decanting to eliminate easily suspended amorphous material, then drying in air at room temperature. A portion of the solids was submitted for X-ray analysis. The above product was impure, but the major crystalline phase had an X-ray powder diffraction pattern characterized by the data of Table A, supra. The major phase was thus established to be SAPO-5.

(b) A reaction mixture having the same relative concentration of reagents as in part (a) of this Example 2 was prepared by using five times the quantity of each ingredient and changing the order of admixture so that the phosphoric acid and the alumina were first admixed, followed by admixture with the silica sol and finally with the TPAOH. The reaction mixture was crystallized in a sealed reactor at 200° C. for 24 hours. Part of the larger, denser crystalline particles in the product were concentrated by elutriation with an upflow of water. This portion of the solids was submitted for X-ray analysis and had an X-ray powder diffraction pattern essentially identical to that in Example 1.

(c) A sample of the solids of part (b) supra were examined using a scanning electron microscope which showed the presence of hexagonal tablet-shaped crystals (a morphology found common to SAPO-5 preparations) with some plate-like growths attached, along with what appeared to be amorphous dried gel particles. Certain of the hexagonal tablets were subjected to energy dispersive analysis by X-rays (EDAX) and were found to contain about 90 percent silicon and the balance aluminum and phosphorus in approximately equal proportions.

EXAMPLE 3

(Preparation of SAPO-5)

A reaction mixture was prepared by combining 9.6 grams of a hydrated aluminum oxide (a pseudo-boehmite phase, 74.2 wt. % $Al_2O_3$, 25.8 wt. % $H_2O$) and 16.2 grams of 85% $H_3PO_4$ and mixing until homogeneous. To this mixture was added 125.1 grams of an aqueous sol containing 33.7 wt. % $SiO_2$, and the mixture stirred until homogeneous. To this mixture was added 10.3 grams of tri-n-propylamine ($Pr_3N$) and the resulting mixture stirred until homogeneous. The composition of the final reaction mixture in molar oxide ratios was:

10.0$SiO_2$:$Pr_3N$:$Al_2O_3$:$P_2O_5$:69.7$H_2O$

A portion of the reaction mixture was sealed in a stainless steel pressure vessel lined with polytetrafluoroethylene and heated in an oven at 200° C. at autogenous pressure for 96 hrs. The solid reaction product was recovered by filtration, washed with $H_2O$ and dried in air at room temperature. A portion of the solids was submitted for X-ray analysis. The product was impure but the major crystalline phase had an X-ray diffraction pattern essentially identical to that in Example 1.

EXAMPLE 4

(Preparation of SAPO-5)

Another portion of the gel prepared in Example 1 was similarly digested but at 125° C. for 2 weeks. The X-ray diffraction pattern of the washed, filtered, room temperature dried solid was essentially identical to that of Example 1 with the exception of a minor amount of crystalline impurity.

EXAMPLE 5

(Preparation of SAPO-5)

A first mixture was prepared by combining 80.1 grams of an aqueous silica sol (30 wt. % $SiO_2$) with 176.0 grams of an aqueous solution of 23 wt. % tetra-n-propylammonium hydroxide (TPAOH) and heating to boiling with loss of 37.0 grams of water. A second mixture was prepared by combining 27.5 grams of a hydrated aluminum oxide (pseudo-boehmite, 74.2 wt. % $Al_2O_3$, 25.8 wt. % $H_2O$) with 46.1 grams of 85 wt. % orthophosphoric acid and 143.6 grams of water and stirring until homogeneous. The two reactions mixtures were mixed together, and the resultant mixture stirred until homogeneous. The composition of the final reaction mixture in molar oxide ratios was:

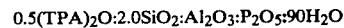

0.5(TPA)$_2$O:2.0$SiO_2$:$Al_2O_3$:$P_2O_5$:90$H_2O$

A portion of the reaction mixture was sealed in a stainless steel pressure vessel having an inert liner, and heated in an oven at 200° C. at autogenous pressure for 22 hours. The solid reaction product was recovered by filtration, washed with water, and dried in air at 100° C. A portion of the solids was subjected to X-ray analysis. The product was impure but the major phase and an X-ray powder diffraction pattern corresponding essentially to that in Example 1.

EXAMPLE 6

(Preparation of SAPO-5)

A reaction mixture was prepared by combining 90.7 grams of aluminum isopropoxide (Al(OC$_3$H$_7$)$_3$) and 100 grams of water, to which was added 46.2 grams of 85 wt. % orthophosphoric acid (H$_3$PO$_4$) and 11 grams of water. To this mixture was added 1.33 grams of a fume silica (95% SiO$_2$, 5% LOI) and the mixture stirred until homogeneous. To one third by weight of this mixture was added 27.2 grams of an aqueous solution of 40 wt. % tetraethylammonium hydroxide (TEAOH), and the mixture stirred until homogeneous. The composition of the final reaction mixture in molar oxide ratios was:

0.5(TEA)$_2$O:0.1SiO$_2$:Al$_2$O$_3$:0.9P$_2$O$_5$:42H$_2$O

The reaction mixture was placed in a stainless steel pressure vessel lined with an inert plastic material (polytetrafluoroethylene) and heated in an oven at 150° C. at autogeneous pressure for 45 hours. The solid reaction product was recovered by centrifugation, washed with water, and dried in air at room temperature. A portion of the solids was subjected to X-ray analysis. The above product (SAPO-5) was impure but the major phase had an X-ray powder diffraction pattern characterized by the data in Table B, below.

TABLE B

| 2θ | d | 100 × I/I$_o$ |
|---|---|---|
| 7.50 | 11.8 | 100 |
| 12.95 | 6.84 | 12* |
| 15.00 | 5.91 | 23 |
| 19.90 | 4.46 | 56 |
| 20.95 | 4.24 | 52* |
| 22.50 | 3.95 | 68 |
| 24.70 | 3.60 | 2 |
| 26.15 | 3.40 | 29 |
| 28.90 | 3.09 | 8 |
| 30.25 | 2.95 | 17 |
| 33.75 | 2.66 | 3 |
| 34.80 | 2.58 | 12 |
| 37.10 | 2.42 | 2 |
| 37.70 | 2.39 | 7 |
| 41.80 | 2.16 | 1 |
| 42.60 | 2.12 | 2 |
| 48.10 | 1.89 | 2* |
| 52.10 | 1.76 | 2 |

*contains impurity peak

EXAMPLE 7

(Preparation of SAPO-5)

A reaction mixture was prepared by combining 57.8 grams of 85 wt. % orthophosphoric acid (H$_3$PO$_4$) and 29.5 grams of water wth 102.1 grams aluminum isopropoxide (Al(OC$_3$H$_7$)$_3$). The well-stirred mixture was added to 30.1 grams of an aqueous silica sol containing 30 wt. % SiO$_2$, and 4 grams of water and the resulting mixture stirred until homogeneous. To 58.5 grams of this mixture was added 54.2 grams of an aqueous solution of 25 wt. % tetra-n-propylammonium hydroxide (TPAOH), and the mixture stirred until homogeneous. The composition of the final reaction mixture in terms of molar oxide ratios was:

0.5(TPA)$_2$O:0.6SiO$_2$:Al$_2$O$_3$:P$_2$O$_5$:51H$_2$O

In terms of molar proportions in which the silicon, aluminum and phosphorus sources are expressed as TO$_2$, i.e., (Si$_x$Al$_y$P$_z$)O$_2$, units, the reaction mixture can be expressed as:

0.22(TPA):(Si$_{0.13}$Al$_{0.43}$P$_{0.43}$)O$_2$:11.1H$_2$O

A portion of the reaction mixture was placed in a stainless steel pressure vessel having an inert liner, and heated in an oven at 200° C. at autogeneous pressure for 48 hours. The solid reaction product was recovered by centrifugation, washed with water, and dried in air at 100° C. As indicated by X-ray analysis the above product was impure but the major phase (SAPO-5) has an X-ray powder diffraction pattern essentially identical to that in Example 6.

EXAMPLE 8

(Preparation of SAPO-5)

A first mixture was prepared by combining 57.7 grams of 85 wt. % orthophosphoric acid (H$_3$PO$_4$) and 15.0 grams of water and adding to 102.1 grams of aluminum isopropoxide (Al(OC$_3$H$_7$)$_3$) and mixing well. A solution of 6.0 grams of NaOH in 11.8 grams of water was mixed into 30.1 grams of an aqueous sol containing 30 wt. % SiO$_2$ stabilized with a small amount of NaOH, to form a second mixture. The two mixtures were combined and stirred until homogeneous. To 71.0 grams of this third mixture were added 24.6 grams of an aqueous solution of 40 wt. % tetraethylammonium hydroxide (TEAOH) and 26.0 grams of water, and the mixture stirred until homogeneous. The chemical composition of the final reaction mixture in terms of molar oxide ratios was:

0.5(TEA)$_2$O:0.3Na$_2$O:Al$_2$O$_3$:P$_2$O$_5$:0.6SiO$_2$:60H$_2$O

A portion of the reaction mixture was placed in a stainless steel pressure vessel lined with polytetrafluoroethylene and heated in an oven at 200° C. at autogenous pressure for 48 hours. The solid reaction product was recovered by centrifugation, washed with water, and dried in air at 100° C. The above product was impure but a major crystalline phase had an X-ray powder diffraction pattern essentially identical to that in Example 6. The product was designated SAPO-5.

EXAMPLE 9

(Preparation of SAPO-5)

(a) A reaction mixture was prepared by combining 18.44 grams of 85 wt. % orthophosphoric acid (H$_3$PO$_4$) and 11.56 grams of water, to which was added 11.04 grams of hydrated aluminum oxide (a pseudo-boehmite phase, 74.2 wt. % Al$_2$O$_3$, 25.8 wt. % H$_2$O), and stirred until homogeneous. To this mixture was added a dispersion of 2.08 grams of a fumed silica (92.8 wt. % SiO$_2$, 7.2 wt. % H$_2$O), in 81.64 grams of an aqueous solution of 40% tetra-n-propylammonium hydroxide (TPAOH), and the mixture stirred until homogeneous. The composition of the final reaction mixture in molar oxide ratios was:

Al$_2$O$_3$:P$_2$O$_5$:0.4SiO$_2$:(TPA)$_2$O:50H$_2$O

A portion of the reaction mixture was sealed in a stainless steel pressure vessel lined with an inert plastic material and heated in an oven at 225° C. at autogeneous pressure for 24 hours. The solid reaction product was recovered by centrifuging and washing with water, and dried in air at room temperature. The above product has an X-ray powder diffraction pattern characterized by the following data:

TABLE C

| 2θ | d | 100 × I/I$_o$ |
|---|---|---|
| 7.4 | 11.95 | 100 |
| 12.9 | 6.86 | 11 |
| 14.9 | 5.95 | 25 |
| 19.7 | 4.51 | 51 |
| 21.1 | 4.21 | 67 |
| 22.3 | 3.99 | 92 |
| 24.8 | 3.59 | 5 |
| 25.8 | 3.453 | 37 |
| 28.9 | 3.089 | 21 |
| 29.9 | 2.988 | 22 |
| 33.6 | 2.667 | 5 |
| 34.4 | 2.607 | 16 |
| 36.8 | 2.442 | 3 |
| 37.6 | 2.392 | 9 |
| 41.5 | 2.176 | 3 |
| 42.2 | 2.141 | 5 |
| 42.8 | 2.113 | 3 |
| 43.5 | 2.080 | 3 |
| 44.9 | 2.019 | 3 |
| 47.6 | 1.910 | 8 |

Chemical analysis established that the solids (product) comprised 8.0 wt. % C, 0.97 wt. % N., 7.22 wt. % SiO$_2$, 33.5 wt. % Al$_2$O$_3$, 44.5 wt. % P$_2$O$_5$, 12.8 wt. % LOI, giving a product composition in terms of molar oxide ratios of:

0.085(TPA)$_2$O:0.37SiO$_2$:1.0Al$_2$O$_3$:0.96P$_2$O$_5$:0.26-H$_2$O

In terms of moles of organic constituent per average mole of TO$_2$ units, the composition was (anhydrous basis):

0.040(TPA):(Si$_{0.08}$Al$_{0.47}$P$_{0.45}$)O$_2$ (b) A portion of solid crystalline product was calcined in air at about 600° C. for 1 hour. The calcined product had an X-ray powder diffraction pattern characterized by the following data:

TABLE D

| 2θ | d | 100 × I/I$_o$ |
|---|---|---|
| 7.5 | 11.79 | 100 |
| 13.0 | 6.81 | 27 |
| 15.0 | 5.91 | 11 |
| 19.9 | 4.46 | 42 |
| 21.3 | 4.17 | 62 |
| 22.6 | 3.93 | 96 |
| 25.0 | 3.56 | 4 |
| 26.0 | 3.427 | 44 |
| 29.2 | 3.058 | 23 |
| 30.2 | 2.959 | 23 |
| 33.8 | 2.652 | 6 |
| 34.6 | 2.592 | 17 |

(c) Adsorption capacities were measured on the calcined product of part (b), supra using a standard McBain-Bakr gravimetric adsorption apparatus. The following data were obtained on a sample activated at 350° C.

| | Kinetic Diameter, A | Pressure, Torr | Temp., °C. | Wt. % Adsorbed |
|---|---|---|---|---|
| O$_2$ | 3.46 | 100 | −183 | 14.5 |
| O$_2$ | 3.46 | 750 | −183 | 19.8 |
| Cyclohexane | 6.0 | 60 | 24 | 10.9 |
| Neopentane | 6.2 | 743 | 24 | 7.6 |
| H$_2$O | 2.65 | 4.6 | 24 | 14.7 |
| H$_2$O | 2.65 | 20.0 | 24 | 31.3 |

The pore size of the calcined product is greater than 6.2 A, as shown by adsorption of neopentane, kinetic diameter of 6.2 A.

(d) Ion-exchange studies were carried out on 1.0 gram of the product of part (a) calcined in air for 2 hours at 600° C. The sample was stirred at room temperature for 10 minutes with 25 cc of a saturated NaCl solution containing 1.0 grams of NaHCO$_3$. After being washed with 1 liter of hot water and then 1 liter of cold water, the product was dried in air at 100° C. for 2 hours. Chemical analysis of the product showed 29.5 wt. % Al$_2$O$_3$, 39.0 wt. % P$_2$O$_5$, 7.6 wt. % SiO$_2$, 3.3 wt. % Na$_2$O corresponding to a product composition in molar oxide ratios of 1.0Al$_2$O$_3$:0.95P$_2$O$_5$:0.44SiO$_2$:0.18Na$_2$O

EXAMPLE 10

(Preparation of SAPO-5)

Using a procedure essentialy the same as in Example 9(a) supra, and using aluminum isopropoxide as the alumina source, phosphoric acid as the P$_2$O$_5$ source, a fumed silica as the silica source and a 25% aqueous solution of tetra-n-butylammonium hydroxide (TBAOH) as the templating agent, the following gel composition was prepared in terms of mole ratios of oxides:

Al$_2$O$_3$:P$_2$O$_5$:0.4SiO$_2$:(TBA)$_2$O:100H$_2$O

The gel was digested and crystallized for 72 hours under autogenous pressure in a sealed reactor at 200° C. SAPO-5 was produced as evidenced by the X-ray powder diffraction pattern of the solid product.

EXAMPLE 11

(Preparation of SAPO-5)

Using essentially the same procedure as in Example 9(a) supra, and using a pseudo-boemite as the alumina source, triethylphosphate as the P$_2$O$_5$ source, a fumed silica as the SiO$_2$ source and a mixture of tetra-n-propylammonium hydroxide and tetramethylammonium hydroxide as the templating agents, the following gel composition was prepared in terms of mole ratios of oxides.

Al$_2$O$_3$:P$_2$O$_5$:0.4SiO$_2$:0.5(TPA)$_2$O:0.01(TMA)$_2$0.50-H$_2$O

The gel was digested and crystallized under autogenous pressure in a sealed reactor for 24 hours at 200° C. SAPO-5 was produced as evidenced by the X-ray powder diffraction pattern of the solid product.

EXAMPLE 12

(Preparation of SAPO-5)

(a) A reaction mixture was prepared by combining 40.9 grams aluminum isopropoxide (Al(OC$_3$H$_7$)$_3$) and 44.1 grams H$_2$O to which was added 23.1 grams of 85 wt. % orthophosphoric acid (H$_3$PO$_4$) and 5 grams H$_2$O and the mixture stirred well. Then 60.7 grams of an aqueous sol containing 30 wt. % SiO$_2$ was added to the mixture which was stirred until homogeneous. To this mixture was added 28.7 grams of tri-n-propylamine (Pr$_3$N), and the mixture stirred until homogeneous. The composition of the final reaction mixture in molar oxide ratios was:

2.0Pr$_3$N:0.3SiO$_2$:Al$_2$O$_3$:P$_2$O$_5$:40H$_2$O

A portion of the reaction mixture was sealed in a stainless steel pressure vessel lined with polytetrafluoroethylene and heated in an oven at 150° C. at autogenous pressure for 168 hours. The solid reaction product was recovered by centrifugation, washed with water and dried in air at 100° C. The product had an X-ray powder diffraction pattern essentially identical to that in Example 6, was designated SAPO-5. Chemical analysis showed 5.5 wt. % C, 0.70 wt. % N, 35.3 wt. % Al$_2$O$_3$, 46.2 wt. % P$_2$O$_5$, 1.6 wt. % SiO$_2$, 15.1 wt. % LOI, giving a product composition (anhydrous basis):

0.038Pr$_3$N:(Si$_{0.02}$Al$_{0.51}$P$_{0.47}$)O$_2$

The composition in terms of mole ratios of oxides is:

0.15Pr$_3$N:AL$_2$O$_3$:0.94P$_2$O$_5$:0.08SiO$_2$:1.3H$_2$O

EDAX (energy dispersive analysis by X-ray) microprobe analysis, performed in conjunction with SEM (scanning electron microscope) study, on relatively clean crystals having a crystal morphology characteristic of SAPO-5 gives the following analysis, based on relative peak heights:
 Si: 0.2
 Al: 1.0
 P: 0.9

The product was calcined in air at about 550° C. for 23 hours. The calcined product had an X-ray powder diffraction pattern essentially identical to that in Example 6.

(b) Adsorption capacities were measured on the calcined product of part (a) using a standard McBain:Bakr gravimetric adsorption apparatus. The following data were obtained on a sample activated at 350° C.

|  | Kinetic Diameter, A | Pressure Torr | Temp., °C. | Wt. % Adsorbed |
|---|---|---|---|---|
| O$_2$ | 3.46 | 102 | −183 | 12.0 |
| O$_2$ | 3.46 | 743 | −183 | 14.9 |
| Cyclohexane | 6.0 | 52 | 24.6 | 7.8 |
| Neopentane | 6.2 | 99 | 24.8 | 5.0 |
| H$_2$O | 2.65 | 4.6 | 23.9 | 6.8 |
| H$_2$O | 2.65 | 20.2 | 23.2 | 22.1 |

The pore size of the calcined product is greater than 6.2 A, as shown by adsorption of neopentane, kinetic diameter of 6.2 A.

(c) SAPO-5 was also produced using the mixing procedure of part (a) supra and using as the templating agent choline hydroxide [(CH$_3$)$_3$NCH$_2$CH$_2$OH]OH in proportions with the other reagents to form a reaction gel having a composition in terms of mole ratios:

1.0 Choline hydroxide:Al$_2$O$_3$:P$_2$O$_5$:0.3SiO$_2$:60H$_2$O when the gel was crystallized at 200° C. for 48 hours.

EXAMPLE 13

(Preparation of SAPO-5)

(a) A reaction mixture was prepared by combining 23.06 grams of 85 wt. % orthophosphoric acid (H$_3$PO$_4$) and 82.47 grams of water, to which was added 13.81 grams of hydrated aluminum oxide, (74.2 wt. % Al$_2$O$_3$, 25.8 wt. % H$_2$O) and stirred until homogeneous. To this mixture was added a dispersion of 2.59 grams of fumed silica (92.8 wt. % SiO$_2$, 7.2 wt. % H$_2$O) in 29.41 grams of tri-n-propylamine (Pr$_3$N), and the mixture stirred until homogeneous. The composition of the final reaction mixture in molar oxide ratios was:

Al$_2$O$_3$:P$_2$O$_5$:0.4SiO$_4$:2.0Pr$_3$N:50H$_2$O

The reaction mixture was sealed in a stainless steel pressure vessel lined with an inert plastic material and heated in an oven at 200° C. at autogenous pressure for 24 hours. The solid reaction product was recovered by centrifuging, washing with water, and drying in air at room temperature. The product was impure but the major phase had an X-ray powder diffraction pattern characterized by the following data.

TABLE E

| 2θ | d | 100 × I/I$_o$ |
|---|---|---|
| 7.4 | 11.95 | 88 |
| 12.8 | 6.92 | 14 |
| 14.8 | 5.99 | 21 |
| 19.6 | 4.53 | 47 |
| 20.9 | 4.25 | 61 |
| 22.2 | 4.00 | 100 |
| 24.6 | 3.62 | 5 |
| 25.9 | 3.44 | 33 |
| 28.9 | 3.089 | 23 |
| 30.0 | 2.979 | 21 |
| 33.5 | 2.675 | 5 |
| 34.4 | 2.607 | 16 |
| 36.8 | 2.442 | 7 |
| 37.5 | 2.398 | 14 |
| 40.6 | 2.222 | 2 |
| 41.4 | 2.181 | 3 |
| 42.0 | 2.151 | 5 |
| 42.6 | 2.122 | 5 |
| 43.5 | 2.080 | 3 |
| 47.6 | 1.910 | 7 |

Chemical analysis established that the SAPO-5 product had a composition (anhydrous basis):

0.042Pr$_3$N:(Si$_{0.095}$Al$_{0.47}$P$_{0.435}$)O$_2$ which corresponds, in terms of mole ratios of oxides (anhydrous basis)

Al$_2$O$_3$:0.92P$_2$O$_5$:0.4SiO$_2$:0.18Pr$_3$N (b) Adsorption capacities were measured on the calcined product (600° C. for 1 hour in air) using a standard McBain-Bakr gravimetric adsorption apparatus. The following data were obtained on a sample activated at 350° C.

|  | Kinetic Diameter, A | Pressure, Torr | Temp., °C. | Wt. % Adsorbed |
|---|---|---|---|---|
| O$_2$ | 3.46 | 100 | −183 | 13.2 |
| O$_2$ | 3.46 | 750 | −183 | 18.1 |
| Neopentane | 6.2 | 750 | 24 | 7.3 |
| H$_2$O | 2.65 | 4.6 | 24 | 11.0 |

-continued

| | Kinetic Diameter, A | Pressure, Torr | Temp., °C. | Wt. % Adsorbed |
|---|---|---|---|---|
| $H_2O$ | 2.65 | 21.0 | 24 | 27.2 |

The pore size of the calcined product is greater than 6.2 A, as shown by adsorption of neopentane, kinetic diameter of 6.2 A.

(c) Ion-exchange studies were carried out on 1.0 gram of the product of part (a) calcined in air for 2 hours at 600° C. The sampe was slurried at room-temperature for 10 minutes with 25 cc of a saturated NaCl solution containing 1.0 gram of $NaHCO_3$. After being washed with 1 liter of hot water and 1 liter of cold water, the product was dried in air at 100° C. for 2 hours. Chemical analysis of the ion-exchanged material showed 0.96 wt-% $Na_2O$ and a composition in terms of molar ratios to be:

$SiO_2/Al_2O_3 = 0.49$ $P_2O_5/Al_2O_3 = 0.98$ $Na_2O/Al_2O_3 = 0.055$

EXAMPLE 14

(Preparation of SAPO-5)

Diethylethanolamine, (DEA) was employed to template the formation of SAPO-5 in a reaction mixture prepared by combining 204.3 grams of aluminum isopropoxide with a solution of 115.3 grams of 85 wt-% $H_3PO_4$ in 385.5 grams of water and stirring until homogeneous. Silica in the form of an aqueous sol (30 wt-% $SiO_2$) was then added in an amount of 30.1 grams. To one fourth by weight of the resulting composition was added 14.6 grams of the templating agent to form a final reaction mixture having the following composition in terms of mole ratios of oxides.

(DEA):0.3$SiO_2$:$Al_2O_3$:$P_2O_5$:50$H_2O$

Figure 2:
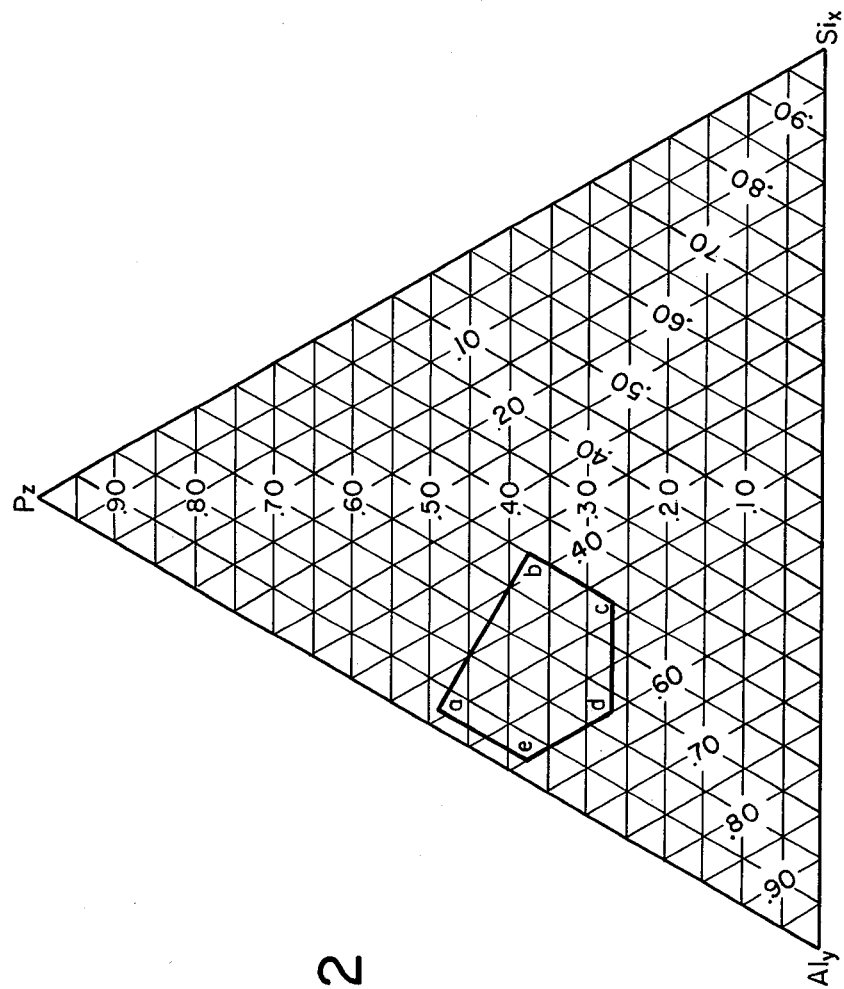
FIG. 2 is a ternary diagram showing the preferred compositional parameters of the silicoaluminophosphates of this invention in terms of mole fractions of silicon, aluminum and phosphorous.

After digestion and crystallization of the reaction mixture at autogenous pressure at 200° C. for 168 hours, the resulting SAPO-5 was found to have a chemical composition in terms of mole ratios of oxides of 0.11(DEA)$_2$0:0.15$SiO_2$:$Al_2O_3$:0.92$P_2O_5$:0.43$H_2O$ The species SAPO-5 as referred to herein is a silicoaluminophosphate material having a three-dimensional microporous crystal framework structure of $PO_2^+$, $AlO_2^-$ and $SiO_2$ tetrahedral units, and whose essential empirical chemical composition on an anhydrous basis is:

mR:($Si_xAl_yP_z$)$O_2$ wherein "R" represents at least one organic templating agent present in the intracrystalline pore system, "m" represents the moles of "R" present per mole of ($Si_xAl_yP_z$)$O_2$ and has a value of from zero to 0.3, "x", "y" and "z" represent respectively, the mole fractions of silicon, aluminum and phosphorus present in the oxide moiety, said mole fractions being within the compositional area bounded by points A, B, C, D and E on the ternary diagram which is FIG. 1, or preferably within the area bounded by points a, b, c, d and e on the ternary diagram which is FIG. 2 said silicoaluminophosphate having a characteristic X-ray powder diffraction pattern which contains at least the d-spacings set forth below in Table I. In the form as synthesized in accordance with the process of this invention, "m" has a value of from 0.02 to 0.3.

TABLE I

| 2θ | d | Relative Intensity |
|---|---|---|
| 7.35–7.65 | 12.0–11.56 | m–vs |
| 19.6–19.95 | 4.53–4.46 | m |
| 20.9–21.3 | 4.25–4.17 | m–vs |
| 22.3–22.6 | 3.99–3.93 | m–vs |
| 25.85–26.15 | 3.46–3.40 | w–m |

All of the as-synthesized SAPO-5 compositions for which x-ray powder diffraction data have presently been obtained have patterns which are within the generalized pattern of Table II below:

TABLE II

| 2θ | d | 100 × $I/I_o$ |
|---|---|---|
| 7.35–7.65 | 12.0–11.56 | 52–100 |
| 12.75–13.1 | 6.94–6.76 | 7–18 |
| 14.8–15.1 | 5.99–5.91 | 13–25 |
| 19.6–19.95 | 4.53–4.47 | 31–56 |
| 20.9–21.3 | 4.25–4.17 | 30–100 |
| 22.3–22.6 | 3.99–3.93 | 44–100 |
| 24.6–24.8 | 3.62–3.59 | 2–5 |
| 25.8–26.15 | 3.453–3.408 | 19–37 |
| 28.9–29.25 | 3.089–3.053 | 8–21 |
| 29.9–30.25 | 2.998–2.954 | 11–22 |
| 33.3–33.85 | 2.691–2.648 | 2–5 |
| 34.4–34.8 | 2.607–2.578 | 9–16 |
| 36.8–37.2 | 2.442–2.417 | 2–3 |
| 37.5–37.9 | 2.398–2.374 | 6–13 |
| 40.6–41.0 | 2.222–2.201 | 0–1 |
| 41.4–41.8 | 2.181–2.161 | 1–3 |
| 42.1–42.4 | 2.146–2.132 | 2–5 |
| 42.6–42.9 | 2.122–2.108 | 1–4 |
| 43.5–43.6 | 2.080–2.076 | 1–3 |
| 44.9–45.0 | 2.019–2.014 | 0–3 |
| 47.55–48.1 | 1.912–1.892 | 3–8 |
| 51.4–51.65 | 1.778–1.773 | 0–2 |
| 51.8–52.1 | 1.765–1.755 | 0–2 |
| 55.4–55.8 | 1.658–1.647 | 1–4 |

It will be noted in the case of SAPO-5 that the essential d-spacings of Table I are common to the X-ray patterns of all of the as-synthesized forms, i.e., template-containing, and those calcined forms of SAPO-5 which contain no templating agent. It has been found, however, that in the case of the X-ray patterns of several other SAPO species, there can be an apparent substantial difference in the position and intensities of certain d-spacings between the as-synthesized and the calcined form. These differences are not believed to be indicative of a fundamental structure change as a consequence of calcination, but rather indicate a relaxation of lattice distortion caused by the presence of organic templating agents in the intracrystalline pore system which are too large to be accommodated without some bond-stretching within the SAPO crystal lattice. Upon calcination, the removal of the organic species by thermal destruction permits the structure to relax to its normal condition. Thus it may be possible to utilize a templating agent in the preparation of SAPO-5 or any SAPO species of this invention which is large enough to change the position of one or more d-spacings with respect to the X-ray patterns presented in this application for such species while not creating a distinct silicoaluminophosphate crystal structure.

EXAMPLE 15

(Preparation of SAPO-11)

(a) A reaction mixture was prepared by combining 160 grams of water and 90.7 grams of aluminum isopropoxide (Al(OC$_3$H$_7$)$_3$) to which was added 51.3 grams of 85 wt. % orthophosphoric acid (H$_3$PO$_4$) and the mixture stirred well. To this was added 1.4 grams of a fumed silica (95 wt. % SiO$_2$; 5 wt. % H$_2$O) and then, after stirring, 7.4 grams of di-n-propylamine (Pr$_2$NH) was added to one-third by weight of the above mixture. The final mixture was stirred until homogeneous. The composition of the final reaction mixture in molar oxide ratios was:

1.0Pr$_2$NH:0.1SiO$_2$:Al$_2$O$_3$:P$_2$O$_5$:42H$_2$O

In terms of molar proportions in which the silicon, aluminum and phosphorus sources are expressed as TO$_2$, i.e., (Si$_x$Al$_y$P$_z$)O$_2$, units, the reaction mixture can be expressed as:

0.24(Pr$_2$NH):(Si$_{0.02}$Al$_{0.49}$Si$_{0.49}$)O$_2$:10.2H$_2$O

The reaction mixture was sealed in a stainless steel pressure vessel lined with polytetrafluoroethylene and heated in an oven at 150° C. at autogenous pressure for 133 hours. The solid reaction product was recovered by centrifugation, washed with water, and dried in air at room temperature. Chemical analysis established the composition to comprise 3.5 wt.-% C, 0.65 wt.-% N, 38.2 wt.-% Al$_2$O$_3$, 35.9 wt.-% P$_2$O$_5$, 2.9 wt.-% SiO$_2$, 17.7 wt.-% LOI, giving a product composition (anhydrous basis) for the SAPO-11 as follows:

0.037Pr$_2$NH:(Si$_{0.04}$Al$_{0.57}$P$_{0.39}$)O$_2$ or, in terms of mole ratios of oxides:
0.13Pr$_2$NH:Al$_2$O$_3$:0.68P$_2$O$_5$:0.13SiO$_2$:2.1H$_2$O The as-synthesized composition had an x-ray powder diffraction pattern characterized by the following data:

TABLE F

| 2θ | d | 100 × I/I$_o$ |
|---|---|---|
| 8.05 | 10.98 | 20 |
| 9.4 | 9.41 | 36 |
| 13.1 | 6.76 | 13 |
| 15.65 | 5.66 | 23 |
| 16.3 | 5.44 | 3 |
| 18.95 | 4.68 | 5 |
| 20.4 | 4.35 | 36 |
| 21.0 | 4.23 | 100 |
| 22.1 | 4.02 | 54 |
| 22.5 | 3.95 | } 56 |
| 22.7 sh* | 3.92 | |
| 23.15 | 3.84 | 66 |
| 24.5 | 3.63 | } 8 |
| 24.7 | 3.60 | |
| 26.4 | 3.38 | 19 |
| 27.2 | 3.28 | 1 |
| 28.6 | 3.121 | 14 |
| 29.0 | 3.079 | 3 |
| 29.45 | 3.033 | 6 |
| 31.5 | 2.840 | 8 |
| 32.8 | 2.730 | 13 |
| 34.1 | 2.629 | 8 |
| 35.75 | 2.512 | 3 |
| 36.3 | 2.475 | 3 |
| 37.5 | 2.398 | |

TABLE F-continued

| 2θ | d | 100 × I/I$_o$ |
|---|---|---|
| 37.8 | 2.380 | } 10 |
| 39.3 | 2.292 | 3 |
| 40.3 | 2.238 | 2 |
| 42.8 | 2.113 | 6 |
| 44.9 | 2.019 | 4 |
| 46.8 | 1.941 | 1 |
| 48.7 | 1.870 | 2 |
| 50.5 | 1.807 | 3 |
| 54.6 | 1.684 | 4 |

*sh = shoulder (b) A portion of the product of part (a) was calcined in air at 500° C. for 1 hour, then at 600° C. for 1 hour. The calcined product has an x-ray powder diffraction pattern characterized by the following data:

| 2θ | d | 100 × I/I$_o$ |
|---|---|---|
| 8.1 | 10.9 | 54 |
| 9.6 | 9.2 | 53 |
| 12.8 | 6.92 | } 18 |
| 13.05 | 6.78 | |
| 15.85 | 5.59 | } 46 |
| 16.1 (sh) | 5.50 | |
| 19.4 (sh) | 4.58 | } 30 |
| 20.3 | 4.37 | |
| 21.3 | 4.17 | 100 |
| 21.9 (sh) | 4.06 | 39 |
| 22.3 | 3.99 | 75 |
| 22.9 (sh) | 3.88 | 41 |
| 23.3 | 3.82 | 60 |
| 24.1 | 3.69 | 9 |
| 24.9 | 3.58 | 5 |
| 26.35 | 3.38 | 20 |
| 28.9 | 3.089 | 12 |
| 29.5 | 3.028 | 11 |
| 30.3 | 2.950 | 5 |
| 31.7 | 2.823 | 9 |
| 32.75 | 2.734 | 14 |
| 34.0 | 2.637 | 4 |
| 34.55 | 2.596 | 5 |
| 36.2 | 2.481 | 7 |
| 37.1 | 2.423 | 2 |
| 37.8 | 2.380 | 10 |
| 39.4 | 2.287 | 2 |
| 41.0 | 2.201 | 1 |
| 43.2 | 2.094 | 3 |
| 44.7 | 2.027 | 3 |
| 48.3 | 1.884 | 1 |
| 51.2 | 1.784 | 2 |

*sh = shoulder (c) Adsorption capacities were measured on this calcined product using a standard McBain-Bakr gravimetric adsorption apparatus. The following data were obtained on a sample activated at 350° C.

| | Kinetic Diameter, Å | Pressure, Torr | Temp, °C. | Wt. % Adsorbed |
|---|---|---|---|---|
| O$_2$ | 3.46 | 102 | −183 | 7.3 |
| O$_2$ | 3.46 | 743 | −183 | 15.3 |
| Cyclohexane | 6.0 | 52 | 24.6 | 6.9 |
| Neopentane | 6.2 | 300 | 24.8 | 1.7 |
| H$_2$O | 2.65 | 4.6 | 23.9 | 11.4 |
| H$_2$O | 2.65 | 20.2 | 23.2 | 18.0 |

The pore size of the calcined product is >6.0 Å and <6.2 Å as shown by adsorption of cyclohexane, kinetic

EXAMPLE 16

(Preparation of SAPO-11)

SAPO-11 was crystallized from a reaction system containing a mixture of two organic templating agents prepared by combining an aqueous solution consisting of 11.53 grams of 85 wt-% orthophosphoric acid and 22.0 grams of water with 6.9 grams of a hydrated aluminum oxide (a pseudo-boehmite, 74.2 wt-% $Al_2O_3$, 25.8 wt-% $H_2O$) and stirring until homogeneous. To this mixture was added a mixture of 1.3 grams of a fumed silica (92.8 wt.% $SiO_2$, 7.2 wt.-% $H_2O$) in 32.46 grams of an aqueous solution of 40.0 wt.-% tetra-n-butylammonium hydroxide (TBAOH). This mixture was stirred until homogeneous, and then 5.10 grams of di-n-propylamine ($Pr_2NH$) was added with stirring until again homogeneous. The composition of the final reaction mixture in molar oxide ratios was:

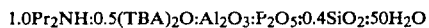

1.0$Pr_2NH$:0.5$(TBA)_2O$:$Al_2O_3$:$P_2O_5$:0.4$SiO_2$:50$H_2O$

The reaction mixture was crystallized at 200° C. under autogenous pressure for 24 hours in a reactor lined with polytetrafluoroethylene. X-ray analyses of a portion of the crystalline product indicated the product to have an X-ray powder diffraction pattern essentially identical to the SAPO-11 product of Example 15(a) supra.

EXAMPLE 17

(Preparation of SAPO-11)

A reaction mixture was prepared by combining 23.06 grams of 85 wt.-% orthophosphoric acid ($H_3PO_4$) and 23.06 grams of water, to which was added 13.81 grams of a hydrated aluminum oxide (a pseudo-boehmite phase, 74.2 wt.-% $Al_2O_3$, 25.8 wt.-% $H_2O$) and stirred until homogeneous. To this mixture was added a mixture of 3.90 grams of a fumed silica (92.8 wt.-% $SiO_2$, 7.2 wt.-% $H_2O$) in 103.5 grams of a solution of 25.0 wt.-% tetra-n-butylammonium hydroxide (TBAOH) in methanol. This mixture was stirred until homogenous and then 20.41 grams of di-n-propylamine was added with stirring until a homogeneous mixture was obtained. The composition of the final reaction mixture in molar oxide ratios was:

2.0$Pr_2NH$:0.5$(TBA)_2O$:$Al_2O_3$:$P_2O_5$:0.6$SiO_2$:16.75$H_2O$:24.3$CH_3OH$

A portion of the reaction mixture was placed in a stainless steel pressure vessel lined with an inert plastic material and heated in an oven at 200° C. at autogenous pressure for 48 hours. The solid reaction product was recovered by centrifuging and washing with water, and dried in air at room temperature. A portion of the solids was submitted for X-ray and chemical analysis. The above product was impure, but the major constituent had an X-ray powder diffraction pattern essentially identical to that of the SAPO-11 composition of Example 15(a) supra. By chemical analysis, the composition was found to be 31.5 wt.-% $Al_2O_3$, 40.9 wt.-% $P_2O_5$, 12.0 wt.-% $SiO_2$, 8.1 wt.-% C, 1.2 wt.-% N, and 13.9 wt.-% LOI.

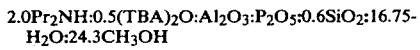

EXAMPLE 18

(Preparation of SAPO-11)

A reaction mixture was prepared by combining 57.8 grams of 85 wt. % orthophosphoric acid ($H_3PO_4$) and 29.5 grams of water, which was added to 102.1 grams aluminum isopropoxide ($Al(OC_3H_7)_3$) and the mixture stirred well. The mixture was added to 30.1 grams of an aqueous sol containing 30 wt. % $SiO_2$, and 4 grams of water and the mixture stirred until homogeneous. To 65.7 grams of this mixture was added 6.7 grams of di-n-propylamine ($Pr_2NH$), and the mixture stirred until homogeneous. The composition of the final reaction mixture in molar oxide ratios was:

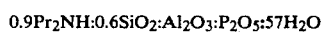

0.9$Pr_2NH$:0.6$SiO_2$:$Al_2O_3$:$P_2O_5$:57$H_2O$

Part of the reaction mixture was sealed in a stainless steel pressure vessel lined with an inert plastic material and heated in an oven at 200° C. at autogenous pressure for 48 hours. The solid reaction product was recovered by centrifugation, washed with water, and dried in air at room temperature. X-ray analysis and chemical analysis established the product to be SAPO-11. The product had an x-ray powder diffraction pattern essentially identical to that in Example 15(a). In accordance with the data from the chemical analysis, the composition consisted of 4.9 wt. % C, 0.9 wt. % N, 36.9 wt. % $Al_2O_3$, 46.3 wt. % $P_2O_5$, 5.5 wt. % $SiO_2$, 9.4 wt. % LOI, giving a product composition (anhydrous basis) of:

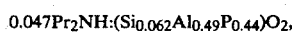

0.047$Pr_2NH$:$(Si_{0.062}Al_{0.49}P_{0.44})O_2$, or in terms of mole ratios of oxides:

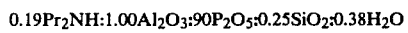

0.19$Pr_2NH$:1.00$Al_2O_3$:90$P_2O_5$:0.25$SiO_2$:0.38$H_2O$

EXAMPLE 19

(Preparation of SAPO-11)

A reaction mixture was prepared in the same way as in Example 18. Part of the reaction mixture was placed in a stainless steel pressure vessel lined with polytetrafluoroethylene and heated in an oven at 200° C. at autogenous pressure for 168 hours. The solid reaction product was recovered by centrifugation, washed with water, and dried in air at 100° C. A portion of the solids was submitted for x-ray and infrared analysis. The SAPO-11 product had an x-ray powder diffraction pattern essentially identical to that in Example 15(a).

EXAMPLE 20

(Preparation of SAPO-11)

(a) A reaction mixture was prepared in essentially the same way as in Example 19. One half of the reaction mixture was sealed in a stainless steel pressure vessel lined with an inert plastic material and heated in an oven at 200° C. at autogenous pressure for 168 hours. The solid reaction product was recovered by centrifugation, washed with water, and dried in air at 100° C. Chemical analysis of the SAPO-11 product showed 37.0 wt.-% $Al_2O_3$, 44.6 wt.-% $P_2O_5$, 7.6 wt.-% $SiO_2$, 9.3 wt.-% LOI, (C and N were not determined) giving a non-volatile product composition in solid molar oxide ratios of:

0.35$SiO_2$:1.00$Al_2O_3$:0.87$P_2O_5$

The above product had an x-ray powder diffraction pattern essentially identical to that in Example 15(a).

(b) A portion of the above product was calcined in air at about 550° C. for 7 hours. The calcined product had an x-ray powder diffraction pattern characterized by the following data:

TABLE J

| 2θ | d | 100 × I/I$_o$ |
|---|---|---|
| 8.1 | 10.92 | 25 |
| 9.85 | 8.98 | 48 |
| 11.7 | 7.56 | 4 |
| 12.8 | 6.92 | 21 |
| 13.6 | 6.51 | 3 |
| 14.7 | 6.03 | 3 |
| 16.1 | 5.50 | 63 |
| 17.6 | 5.04 | 2 |
| 19.55 | 4.54 | 10 |
| 20.0 | 4.44 | 26 |
| 20.8 | 4.27 | 9 |
| 21.95 | 4.05 | 100 |
| 22.3 | 3.99 } | 52 |
| 22.5 | 3.95 | |
| 23.5 | 3.786 | 56 |
| 24.1 | 3.693 | 17 |
| 24.3 | 3.663 | 8 |
| 25.8 | 3.453 | 19 |
| 26.8 | 3.326 | 9 |
| 27.25 | 3.273 | 12 |
| 27.7 | 3.220 | 14 |
| 28.6 | 3.121 | 3 |
| 29.7 | 3.008 | 27 |
| 30.4 | 2.940 | 16 |
| 31.8 | 2.814 | 6 |
| 32.7 | 2.739 | 19 |
| 34.1 | 2.629 | 5 |
| 34.6 | 2.592 | 3 |
| 35.65 | 2.518 | 7 |
| 37.3 | 2.411 | 5 |
| 38.4 | 2.344 | 2 |
| 38.8 | 2.321 | 11 |
| 41.05 | 2.199 | 5 |
| 43.6 | 2.076 | 2 |
| 44.7 | 2.027 | 3 |
| 45.45 | 1.996 | 2 |
| 49.2 | 1.852 | 7 |
| 53.7 | 1.707 | 2 |
| 54.6 | 1.681 | 1 |

(c) Adsorption capacities were measured on this calcined product using a standard McBain-Bakr gravimetric adsorption apparatus. The following data were obtained on a sample activated at 350° C.

| | Kinetic Diameter, A | Pressure, Torr | Temp., °C. | Wt. % Adsorbed |
|---|---|---|---|---|
| O$_2$ | 3.46 | 102 | −183 | 8.4 |
| O$_2$ | 3.46 | 743 | −183 | 10.9 |
| Cyclohexane | 6.0 | 52 | 24.6 | 4.5 |
| Neopentane | 6.2 | 300 | 24.8 | 0.8 |
| H$_2$O | 2.65 | 4.6 | 23.9 | 10.5 |
| H$_2$O | 2.65 | 20.2 | 23.2 | 15.4 |

The pore size of the calcined product is >6.0 A and <6.2 A as shown by adsorption of cyclohexane, kinetic diameter of 6.0 A and nil adsorption of neopentane, kinetic diameter of 6.2 A.

(d) Another portion of the solid crystalline product obtained in part (a) was calcined in air on a programmed run from 100° C. to 600° C. for 8 hours. The calcined product had an x-ray powder diffraction pattern essentially identical to that in Example 15(b).

(e) Adsorption capacities were measured on this calcined product of part (d) using a standard McBain-Bakr gravimetric adsorption apparatus. The following data were obtained on a sample activated at 350° C.

| | Kinetic Diameter, A | Pressure, Torr | Temp., °C. | Wt. % Adsorbed |
|---|---|---|---|---|
| O$_2$ | 3.46 | 102 | −183 | 8.1 |
| O$_2$ | 3.46 | 743 | −183 | 11.2 |
| Cyclohexane | 6.0 | 52 | 24.6 | 4.6 |
| Neopentane | 6.2 | 300 | 24.8 | 0.7 |
| H$_2$O | 2.65 | 4.6 | 23.9 | 10.6 |
| H$_2$O | 2.65 | 20.2 | 23.2 | 15.2 |

The pore size of the calcined product is >6.0 A and <6.2 A as shown by adsorption of cyclohexane, kinetic diameter of 6.0 A and nil adsorption of neopentane, kinetic diameter of 6.2 A.

EXAMPLE 21

(Preparation of SAPO-11)

A reaction mixture was prepared by combining 23.1 grams of 85 wt. % orthophosphoric acid (H$_3$PO$_4$) and 60 grams of water, which was added to 40.9 grams of aluminum isopropoxide (Al(OC$_3$H$_7$)$_3$) and 5.0 grams of water and the mixture stirred well. To this mixture was added 6.0 grams of an aqueous sol containing 30 wt. % SiO$_2$, and then 5 grams of water and stirred until homogeneous. To this mixture were added 10.1 grams of diisopropylamine (i-Pr$_2$NH) and 5.0 grams of water, and the mixture stirred until homogeneous. The composition of the final reaction mixture in molar oxide ratios was:

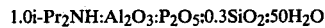

1.0i-Pr$_2$NH:Al$_2$O$_3$:P$_2$O$_5$:0.3SiO$_2$:50H$_2$O

Part of the reaction mixture was placed in a stainless steel pressure vessel lined with an inert plastic material and heated in an oven at 200° C. at autogenous pressure for 48 hours. The solid reaction product was recovered by centrifugation, washed with water, and dried in air at 100° C. The SAPO-11 product was impure but the major phase had an X-ray powder diffraction pattern essentially identical to that in Example 15(a).

EXAMPLE 22

(Preparation of SAPO-11)

To a reaction mixture having the composition (in terms of oxide mole ratios):

(n-C$_3$H$_7$)$_2$NH:Al$_2$O$_3$:P$_2$O$_5$:0.6SiO$_2$:50H$_2$O and formed from di-n-propylamine, aluminum isopropoxide, silica sol, phosphoric acid and water, was added 10 wt.-% SAPO-11 seed crystals (based on the solids content of the gel), and the mixture crystallized in a stirred reactor under autogenous pressure at 150° C. for 19 hours. The SAPO-11 product had an X-ray powder diffraction pattern essentially identical to the product of Example 15(a) above.

The species SAPO-11 as referred to herein is a silicoaluminophosphate material having a three-dimensional microporous crystal framework structure of PO$_2$$^+$, AlO$_2$$^-$ and SiO$_2$ tetrahedral units, and whose essential empirical chemical composition on an anhydrous basis is:

mR:(Si$_x$Al$_y$P$_z$)O$_2$ wherein "R" represents at least one organic templating agent present in the intracrystalline pore system; "m" represents the moles of "R" present per mole of $(Si_xAl_yP_z)O_2$ and has a value from zero to 0.3, "x", "y" and "z" represent respectively, the mole fractions of silicon, aluminum and phosphorus present in the oxide moiety, said mole fractions being within the compositional area bounded by points A, B, C, D and E on the ternary diagram which is FIG. 1 or preferably within the area bounded by points a, b, c, d and e on the ternary diagram which is FIG. 2, said silicoaluminophosphate having a characteristic X-ray powder diffraction pattern which contains at least the d-spacings set forth below in Table III. In the form as synthesized in accordance with the process of this invention, "m" has a value of from 0.02 to 0.3.

TABLE III

| 2θ | d | Relative Intensity |
|---|---|---|
| 9.4–9.65 | 9.41–9.17 | m |
| 20.3–20.6 | 4.37–4.31 | m |
| 21.0–21.3 | 4.23–4.17 | vs |
| 22.1–22.35 | 4.02–3.99 | m |
| 22.5–22.9 (doublet) | 3.95–3.92 | m |
| 23.15–23.35 | 3.84–3.81 | m - s |

All of the as-synthesized SAPO-11 compositions for which x-ray powder diffraction data have presently been obtained have patterns which are within the generalized pattern of the Table IV below.

TABLE IV

| 2θ | d | 100 × I/I$_o$ |
|---|---|---|
| 8.05–8.3 | 10.98–10.65 | 20–42 |
| 9.4–9.65 | 9.41–9.17 | 36–58 |
| 13.1–13.4 | 6.76–6.61 | 12–16 |
| 15.6–15.85 | 5.68–5.59 | 23–38 |
| 16.2–16.4 | 5.47–5.40 | 3–5 |
| 18.95–19.2 | 4.68–4.62 | 5–6 |
| 20.3–20.6 | 4.37–4.31 | 36–49 |
| 21.0–21.3 | 4.23–4.17 | 100 |
| 22.1–22.35 | 4.02–3.99 | 47–59 |
| 22.5–22.9 (doublet) | 3.95–3.92 | 55–60 |
| 23.15–23.35 | 3.84–3.81 | 64–74 |
| 24.5–24.9 (doublet) | 3.63–3.58 | 7–10 |
| 26.4–26.8 (doublet) | 3.38–3.33 | 11–19 |
| 27.2–27.3 | 3.28–3.27 | 0–1 |
| 28.3–28.5 (shoulder) | 3.15–3.13 | 11–17 |
| 28.6–28.85 | 3.121–3.094 | |
| 29.0–29.2 | 3.079–3.058 | 0–3 |
| 29.45–29.65 | 3.033–3.013 | 5–7 |
| 31.45–31.7 | 2.846–2.823 | 7–9 |
| 32.8–33.1 | 2.730–2.706 | 11–14 |
| 34.1–34.4 | 2.629–2.607 | 7–9 |
| 35.7–36.0 | 2.515–2.495 | 0–3 |
| 36.3–36.7 | 2.475–2.449 | 3–4 |
| 37.5–38.0 (doublet) | 2.398–2.368 | 10–13 |
| 39.3–39.55 | 2.292–2.279 | 2–3 |
| 40.3 | 2.238 | 0–2 |
| 42.2–42.4 | 2.141–2.132 | 0–2 |
| 42.8–43.1 | 2.113–2.099 | 3–6 |
| 44.8–45.2 (doublet) | 2.023–2.006 | 3–5 |
| 45.9–46.1 | 1.977–1.969 | 0–2 |
| 46.8–47.1 | 1.941–1.929 | 0–1 |
| 48.7–49.0 | 1.870–1.859 | 2–3 |
| 50.5–50.8 | 1.807–1.797 | 3–4 |
| 54.6–54.8 | 1.681–1.675 | 2–3 |
| 55.4–55.7 | 1.658–1.650 | 0–2 |

EXAMPLE 23

(Preparation of SAPO-16)

A reaction mixture was prepared by combining 46.0 grams of 85 wt. % orthophosphoric acid and 100 grams of water which was added to 81.7 grams of aluminum isopropoxide (Al(OC$_3$H$_7$)$_3$) and 5.0 grams of water and the mixture stirred well. To the above mixture were added 12.0 grams of an aqueous sol containing 30 wt. % SiO$_2$, and 5.0 additional grams of water, and the mixture stirred until homogeneous. To one-half (by weight) of this mixture were added 11.1 grams of quinuclidine, C$_7$H$_{13}$N, (Q) and 21.9 grams of water, and the mixture stirred until homogeneous. The composition of the final reaction mixture in molar oxide ratios was:

1.0Q:Al$_2$O$_3$:P$_2$O$_5$:0.3SiO$_2$:50H$_2$O

Part of the reaction mixture was sealed in a stainless steel pressure vessel having an inert plastic liner and heated in an oven at 200° C. at autogenous pressure for 48 hours. The solid reaction product, denominated SAPO-16, was recovered by centrifugation, washed with water, and dried in air at 100° C. X-ray analysis was performed on a portion of the solids which passed through 100 mesh sieve. The SAPO-16 product had an x-ray powder diffraction pattern characterized by the following data:

TABLE K

| 2θ | d | 100 × I/I$_o$ |
|---|---|---|
| 11.45 | 7.73 | 54 |
| 17.35 | 5.11 | 4 |
| 18.8 | 4.72 | 51 |
| 22.05 | 4.03 | 100 |
| 26.65 | 3.345 | 20 |
| 29.2 | 3.058 | 6 |
| 29.85 | 2.993 | 25 |
| 32.7 | 2.739 | 3 |
| 34.8 | 2.578 | 4 |
| 38.05 | 2.365 | 8 |
| 39.9 | 2.259 | 3 |
| 44.4 | 2.040 | 2 |
| 48.5 | 1.877 | 6 |
| 49.0 | 1.859 | 1 |
| 52.4 | 1.746 | 2 |
| 54.8 | 1.675 | 2 |

EXAMPLE 24

(Preparation of SAPO-16)

A reaction mixture was prepared by combining 132 grams of water and 132.8 grams of aluminum isopropoxide (Al(OC$_3$H$_7$)$_3$) to which was added 45.0 grams of water and 30.1 grams of an aqueous sol containing 30 wt. % SiO$_2$, and the mixture stirred well. To this mixture was added 57.7 grams of 85 wt. % orthophosphoric acid, and the mixture stirred until homogeneous. To this mixture were added an aqueous solution containing 27.8 grams of quinuclidine, C$_7$H$_{13}$N, (Q) and 45 grams of water, and then 5 additional grams of water, and the mixture stirred until homogeneous. The composition of the final reaction mixture in molar oxide ratios was:

1.0Q:1.3Al$_2$O$_3$:P$_2$O$_5$:0.6SiO$_2$:60H$_2$O

Part of the reaction mixture was sealed in a stainless steel pressure vessel lined with polytetrafluoroethylene and heated in an oven at 200° C. at autogenous pressure for 338 hours. The solid reaction product was recovered by centrifugation, washed with water, and dried in air at 100° C. The SAPO-16 product had an x-ray powder diffraction pattern essentially identical to that in Example 23. By chemical analysis, the composition of the SAPO-16 product was found to be 12.2 wt. % C, 1.9 wt. % N, 7.8 wt. % SiO$_2$, 34.6 wt. % Al$_2$O$_3$, 32.1 wt. % P$_2$O$_5$, 24.6 wt. % LOI, corresponding to the formula (anhydrous basis)

$$0.116\ \text{Quinuclidine}:(Si_{0.10}Al_{0.54}P_{0.36})O_2$$

In terms of mole ratios of oxides, the composition was:

$$0.215Q_2O:Al_2O_3:0.38SiO_2:0.67P_2O_5:1.4H_2O$$

The species SAPO-16 as referred to herein is a silicoaluminophosphate material having a three-dimensional microporous crystal framework structure of PO$_2^+$, AlO$_2^-$ and SiO$_2$ tetrahedral units, and whose essential empirical chemical composition on an anhydrous basis is:

$$mR:(Si_xAl_yP_z)O_2$$

wherein "R" represents at least one organic templating agent present in the intracrystalline pore system; "m" represents the moles of "R" present per mole of (Si$_x$Al$_y$P$_z$)O$_2$ and has a value of from zero to 0.3, "x", "y" and "z" represent respectively, the mole fractions of silicon, aluminum and phosphorus present in the oxide moiety, said mole fractions being within the compositional area bounded by points A, B, C, D and E on the ternary diagram which is FIG. 1, or preferably within the area bounded by points a, b, c, d and e on the ternary diagram which is FIG. 2, said silicoaluminophosphate having a characteristic X-ray powder diffraction pattern which contains at least the d-spacings set forth below in Table V. In the form as synthesized in accordance with the process of this invention, "m" has a value of from 0.02 to 0.3.

TABLE V

| 2θ | d | Relative Intensity |
|---|---|---|
| 11.3–11.5 | 7.83–7.69 | m |
| 18.7–18.9 | 4.75–4.70 | m |
| 21.9–22.3 | 4.06–3.99 | vs |
| 26.5–27.0 | 3.363–3.302 | w–m |
| 29.7–30.05 | 3.008–2.974 | w–m |

All of the as-synthesized SAPO-16 compositions for which X-ray powder diffraction data have presently been obtained have patterns which are within the generalized pattern of Table VI, below.

TABLE VI

| 2θ | d | 100 × I/I$_o$ |
|---|---|---|
| 11.3–11.5 | 7.83–7.69 | 52–66 |
| 17.0–17.5 | 5.22–5.07 | 0–4 |
| 18.7–18.9 | 4.75–4.70 | 50–58 |
| 21.9–22.3 | 4.06–3.99 | 100 |
| 26.5–27.0 | 3.363–3.302 | 15–23 |
| 29.1–29.4 | 3.069–3.038 | 5–13 |
| 29.7–30.05 | 3.008–2.974 | 23–26 |
| 32.7–32.9 | 2.739–2.722 | 0–3 |
| 34.4–34.8 | 2.607–2.578 | 2–4 |
| 38.0–38.3 | 2.368–2.350 | 7–9 |
| 39.9–40.3 | 2.259–2.238 | 0–7 |
| 44.3–44.45 | 2.045–2.038 | 0–4 |
| 48.5–48.7 | 1.877–1.870 | 6–8 |
| 49.0–49.4 | 1.859–1.845 | 0–2 |
| 52.3–52.5 | 1.749–1.743 | 0–2 |
| 54.8–54.9 | 1.675–1.672 | 0–2 |

EXAMPLE 25

(Preparation of SAPO-17)

SAPO-17 was crystallized from a reaction mixture formed by combining 57.7 grams of 85 wt. % orthophosphoric acid and 130.0 grams of water with 132.8 grams of aluminum isopropoxide (Al(OC$_3$H$_7$)$_3$) and mixing well. To this mixture were added 47.0 grams of water and 30.1 grams of an aqueous sol containing 30 wt. % SiO$_2$, and the mixture stirred until homogeneous. To this mixture was added a solution of 27.8 grams of guinuclidine, C$_7$H$_{13}$N, (Q) in 50.0 grams of water, and the mixture stirred until homogeneous. The composition of the final reaction mixture in molar oxide ratios was:

$$Q:0.6SiO_2:1.3Al_2O_3:P_2O_5:60H_2O$$

Part of the reaction mixture was placed in a stainless steel pressure vessel lined with an inert plastic material and heated in an oven at 200° C. at autogenous pressure for 338 hours. The solid reaction product was recovered by centrifugation, washed with water, and dried in air at 100° C. The SAPO-17 product was impure but the minor phase had an X-ray powder diffraction pattern characterized by the following data:

TABLE L

| 2θ | d | 100 × I/I$_o$ |
|---|---|---|
| 7.75* | 11.4 | 100 |
| 9.8 | 9.03 | 5 |
| 13.4* | 6.61 | 60 |
| 15.55* | 5.70 | 65 |
| 16.7 | 5.31 | 5 |
| 18.0 | 4.93 | 25 |
| 19.7 | 4.51 | 10 |
| 20.6* | 4.31 | 100 |
| 21.4 (sh) | 4.15 | |
| 23.4 | 3.80 | 20 |
| 25.4 | 3.507 | 15 |
| 27.0 | 3.302 | 24 |
| 27.4 | 3.255 | 5 |
| 28.7 | 3.110 | 5 |
| 30.6 (sh) | 2.921 | |
| 31.35 | 2.853 | 10 |
| 32.0 | 2.797 | 20 |
| 33.4 | 2.683 | 5 |
| 36.05 | 2.491 | 10 |
| 36.45 | 2.465 | 10 |
| 40.0** | 2.254 | 40 |
| 40.3** | 2.238 | |
| 45.9 | 1.977 | 5 |
| 49.7 | 1.834 | 5 |
| 52.3** | 1.749 | 15 |
| 53.9 | 1.701 | 5 |
| 55.5 | 1.656 | 5 |

*probably contains peak from another phase
**contains peak from another phase

EXAMPLE 26

(Preparation of SAPO-17)

(a) A substantially purer SAPO-17 composition was prepared using cyclohexylamine (instead of the quinuclidine of Ex. 25 supra) as the templating agent and decreasing the relative proportion of silica in the gel. This superior reaction mixture was prepared by combining 81.7 grams of aluminum isopropoxide [Al(OC$_3$H$_7$)$_3$] with a solution of 46.1 grams of 85 wt. % orthophosphoric acid (H$_3$PO$_4$) in 159.6 grams of H$_2$O, stirring until homogeneous, and then adding 4.0 grams of an aqueous silica sol containing 30 wt.-% SiO$_2$. The resulting mixture was stirred until it was homogeneous. To this mixture was added 19.8 grams of cyclohexylamine (CHA), and the mixture stirred until homogeneous. The composition of the final reaction mixture in molar oxide ratios was:

1.0CHA:0.1SiO$_2$:Al$_2$O$_3$:P$_2$O$_5$:50H$_2$O

A portion of the reaction mixture was sealed in a stainless steel pressure vessel lined with polytetrafluoroethylene and heated in an oven at 200° C. at autogenous pressure for 50 hours. The solid reaction product was recovered by filtration, washed with water, and dried in air at 100° C. By chemical analysis, the composition of the product was found to be 9.5 wt.-% C; 1.6 wt.-% SiO$_2$; 37.8 wt.-% Al$_2$O$_3$; 39.9 wt.-% P$_2$O$_5$ and 19.8 wt.-% LOI, corresponding to the formula (anhydrous basis):

0.103CHA:(Si$_{0.02}$Al$_{0.56}$P$_{0.42}$)O$_2$, or in terms of molar oxide ratios:

0.18(CHA)$_2$O:Al$_2$O$_3$:0.76P$_2$O$_5$:0.07SiO$_2$

The SAPO-17 product was impure and had an x-ray powder diffraction pattern characterized by the following data:

TABLE M

| 2θ | d | 100 × I/I$_o$ |
|---|---|---|
| 7.7 | 11.5 | 100 |
| 9.8 | 9.03 | 36 |
| 10.9* | 8.12 | 9 |
| 11.8 | 7.50 | 1 |
| 13.4** | 6.61 | 95 |
| 14.2 | 6.24 | 6 |
| 15.5 | 5.72 | 37 |
| 16.6 | 5.34 | 19 |
| 17.4* | 5.10 | 8 |
| 18.0 | 4.93 | 18 |
| 19.65 | 4.52 | 39 |
| 20.5 | 4.33 | 80 |
| 21.4** | 4.15 | 35 |
| 22.0* | 4.04 | 16 |
| 22.5 | 3.95 | 7 |
| 23.3** | 3.82 | 38 |
| 23.8 | 3.74 | 32 |
| 25.4 | 3.507 | 38 |
| 27.0** | 3.302 | 49 |
| 27.4 | 3.255 | 9 |
| 28.7** | 3.110 | 18 |
| 30.6 | 2.921 | 5 |
| 31.3 | 2.858 | 20 |
| 31.85 | 2.810 | 48 |
| 32.2* | 2.780 | sh |
| 33.55 | 2.671 | 19 |
| 34.6* | 2.592 | 1 |
| 35.9** | 2.501 | 8 |
| 36.4 | 2.468 | 4 |
| 37.4 | 2.404 | 2 |
| 37.9 | 2.374 | 2 |
| 39.8 | 2.265 | 3 |
| 40.3 | 2.238 | 1 |
| 40.9 | 2.206 | 1 |
| 42.1 | 2.146 | 2 |
| 42.6 | 2.122 | 1 |
| 43.7 | 2.071 | 11 |
| 45.6 | 1.989 | 1 |
| 46.5 | 1.953 | 2 |
| 47.8 | 1.903 | 1 |
| 48.7 | 1.870 | 1 |
| 49.3 | 1.848 | sh |
| 49.6 | 1.838 | 15 |
| 52.0 | 1.759 | 10 |
| 53.8 | 1.704 | 2 |
| 55.45 | 1.657 | 11 |

**contains peak from another phase
*Peak from another phase (b) The product was calcined for 4 hours at 550° C. in air. The calcined product had an x-ray powder diffraction pattern characterized by the following data (known impurity peaks have been omitted):

TABLE N

| 2θ | d | 100 × I/I$_o$ |
|---|---|---|
| 7.7 | 11.5 | 92 |
| 9.65 | 9.17 | 32 |
| 11.5 | 7.69 | 10 |
| 13.5* | 6.56 | 100 |
| 13.9 | 6.37 | 21 |
| 15.6 | 5.68 | 11 |
| 16.65 | 5.32 | 22 |
| 19.0 | 4.67 | 7 |
| 19.4 | 4.58 | 6 |
| 20.7 | 4.29 | 22 |
| 21.45* | 4.14 | 13 |
| 23.5 | 3.79 | 19 |
| 23.7 | 3.75 | sh |
| 24.5 | 3.63 | 19 |
| 27.15 | 3.285 | 17 |
| 28.0 | 3.187 | 5 |
| 30.1 | 2.969 | 1 |
| 30.6 | 2.921 | 3 |
| 31.25 | 2.862 | 14 |
| 32.0 | 2.797 | 9 |
| 33.55 | 2.671 | 6 |
| 35.0 | 2.564 | 2 |
| 36.2 | 2.481 | 3 |
| 39.4 | 2.287 | 2 |
| 40.2 | 2.243 | 1 |
| 41.3 | 2.186 | 2 |
| 41.9 | 2.156 | 1 |
| 42.6 | 2.122 | 3 |
| 43.5 | 2.080 | 1 |
| 46.0 | 1.973 | 1 |
| 46.4 | 1.957 | 1 |
| 47.1 | 1.929 | 2 |
| 47.9 | 1.899 | 2 |
| 50.1 | 1.821 | 5 |
| 51.2 | 1.784 | 5 |
| 52.7 | 1.737 | 1 |
| 55.2 | 1.664 | 2 |

*contains peak from another phase (c) Adsorption capacities were measured on the calcined product of part (b) supra using standard McBain-Bakr gravimetric adsorption apparatus. The following data were obtained on a sample activated at 350° C.:

|  | Kinetic Diameter, Å | Pressure, Torr | Temp., °C. | Wt. % Adsorbed |
|---|---|---|---|---|
| O$_2$ | 3.46 | 98.5 | −183 | 21.5 |
| O$_2$ | 3.46 | 740 | −183 | 29.4 |
| n-hexane | 4.3 | 53.5 | 24 | 10.3 |
| H$_2$O | 2.65 | 4.6 | 23 | 25.2 |
| H$_2$O | 2.65 | 19.4 | 24 | 35.0 |
| isobutane | 5.0 | 400 | 24 | 1.1 | the pore size of the calcined product is >4.3 Å and <5.0 Å as shown by the adsorption of n-hexane, kinetic diameter of 4.3 Å, and negligible adsorption of isobutane, kinetic diameter of 5.0 Å.

The species SAPO-17 as referred to herein is a silicoaluminophosphate material having a three-dimensional microporous crystal framework structure of PO$_2$+, AlO$_2$− and SiO$_2$ tetrahedral units, and whose essential empirical chemical compositon on an anhydrous basis is:

$$mR:(Si_xAl_yP_z)O_2$$

wherein "R" represents at least one organic templating agent present in the intracrystalline pore system; "m" represents the moles of "R" present per mole of $(Si_xAl_yP_z)O_2$ and has a value of from zero to 0.3, "x", "y" and "z" represent respectively, the mole fractions of silicon, aluminum and phosphorous present in the oxide moiety, said mole fractions being within the compositional area bounded by points A, B, C, D and E on the ternary diagram which is FIG. 1, or preferably within the area bounded by points a, b, c, d and e on the ternary diagram which is FIG. 2, said silicoaluminophosphate having a characteristic X-ray powder diffraction pattern which contains at least the d-spacings set forth below in Table VII. In the form as synthesized in accordance with the process of this invention, "m" has a value of from 0.02 to 0.30.

TABLE VII

| 2θ | d | Relative Intensity |
|---|---|---|
| 7.70–7.75 | 11.5–11.4 | vs |
| 13.4 | 6.61 | s–vs |
| 15.5–15.55 | 5.72–5.70 | s |
| 19.65–19.7 | 4.52–4.51 | w–m |
| 20.5–20.6 | 4.33–4.31 | vs |
| 31.85–32 | 2.810–2.797 | w–m |

All of the as-synthesized SAPO-17 compositions for which x-ray powder diffraction data have presently been obtained have patterns which are within the generalized pattern of Table VIII below.

TABLE VIII

| 2θ | d | 100 × I/I$_o$ |
|---|---|---|
| 7.70 | 11.5–11.45 | 100 |
| 9.8 | 9.03 | 5–36 |
| 11.8 | 7.50 | 1 |
| 13.4 | 6.61 | 60–95 |
| 14.2 | 6.24 | 6 |
| 15.5 | 5.72–5.70 | 37–65 |
| 16.6 | 5.34 | 19 |
| 18.0 | 4.93 | 18–25 |
| 19.65–19.7 | 4.52–4.51 | 10–39 |
| 20.5–20.6 | 4.33–4.31 | 80–100 |
| 21.4 (sh) | 4.15 | |
| 22.5 | 3.95 | 7 |
| 23.3–23.4 | 3.82–3.80 | 20–38 |
| 23.8 | 3.74 | 32 |
| 25.4 | 3.507 | 15–38 |
| 27.0 | 3.302 | 25–49 |
| 27.4 | 3.255 | 5–9 |
| 28.7 | 3.110 | 5–18 |
| 30.6 (sh) | 2.921 | sh–5 |
| 31.3–31.35 | 2.858–2.853 | 10–20 |
| 31.85–32.0 | 2.810–2.797 | 20–48 |
| 33.4–33.55 | 2.683–2.671 | 5–19 |
| 35.9–36.05 | 2.501–2.491 | 8–10 |
| 36.4–36.45 | 2.468–2.465 | 4–10 |
| 40.3 | 2.238 | 1 |
| 43.7 | 2.071 | 11 |
| 45.9 | 1.977 | 5 |
| 49.6–49.7 | 1.838–1.834 | 5–15 |
| 52.0–52.3 | 1.704–1.749 | 10–15 |
| 53.8–53.9 | 1.704–1.701 | 2–5 |
| 55.45–55.5 | 1.657–1.656 | 5–11 |

EXAMPLE 27

(Preparation of SAPO-20)

(a) SAPO-20 was crystallized from a gel prepared by combining a solution of 57.6 grams of 85 wt. % orthophosphoric acid (H$_3$PO$_4$) in 60.2 grams of water with 34.4 grams of a hydrated aluminum oxide (a pseudoboehmite phase, 74.2 wt. % Al$_2$O$_3$ 25.8 wt. % H$_2$O). To this mixture was added 50.1 grams of an aqueous silica sol containing 30 wt.-% SiO$_2$, and after stirring well, was combined with 68 grams of tetramethylammoniumhydroxide pentahydrate (TMAOH.5H$_2$O) and 70 grams of water, and the mixture stirred until homogeneous. The composition of the final reaction mixture in molar oxide ratios was:

0.75(TMA)$_2$O:SiO$_2$:Al$_2$O$_3$:P$_2$O$_5$:50H$_2$O

Part of the reaction mixture was placed in a stainless steel pressure vessel lined with polytetrafluoroethylene and heated in an oven at 125° C. at autogenous pressure for 68 hours. The solid reaction product was recovered by centrifugation, washed with water, and dried in air at 100° C. The SAPO-20 product had an x-ray powder diffraction pattern characterized by the following data:

TABLE O

| 2θ | d | 100 × I/I$_o$ |
|---|---|---|
| 14.1 | 6.28 | 40 |
| 19.9 | 4.46 | 41 |
| 22.2 | 4.00 | 5 |
| 24.4 | 3.65 | 100 |
| 28.2 | 3.164 | 13 |
| 31.5 | 2.840 | 11 |
| 34.7 | 2.585 | 14 |
| 37.5 | 2.398 | 2 |
| 40.2 | 2.243 | 4 |
| 42.85 | 2.110 | 6 |
| 47.65 | 1.908 | 5 |
| 52.0 | 1.759 | 10 |

By chemical analysis, the composition of the SAPO-20 was 9.9 wt. % C, 2.9 wt. % N, 11.3 wt. % SiO$_2$, 30.3 wt. % Al$_2$O$_3$, 35.7 wt. % P$_2$O$_5$, 21.6 wt. % LOI, giving a product composition in molar oxide ratios of:

0.35(TMA)$_2$O:0.63SiO$_2$:Al$_2$O$_3$:0.85P$_2$O$_5$:0.53H$_2$O which corresponds to the formula (anhydrous basis)

0.16(TMA):(Si$_{0.15}$Al$_{0.47}$P$_{0.38}$)O$_2$ (b) A portion of the product of part (a) above was calcined in air at 500° C. for 2 hours. Sometime thereafter adsorption capacities of the calcined product were determined using a standard McBain-Bakr gravimetric adsorption apparatus. The following data were obtained on a sample activated at 350° C.

| | Kinetic Diameter, A | Pressure, Torr | Temp., °C. | Wt. % Adsorbed |
|---|---|---|---|---|
| O$_2$ | 3.46 | 100 | −183 | 3.2 |
| O$_2$ | 3.46 | 761 | −183 | 12.8 |
| H$_2$O | 2.65 | 4.6 | 25.1 | 14.6 |
| H$_2$O | 2.65 | 20.0 | 25.0 | 25.1 |

The pore size of the calcined product is greater than 2.65 A and less than 3.46 A, as shown by adsorption of water, kinetic diameter of 2.65 A, and low adsorption of oxygen at 100 torr, kinetic diameter of 3.46 A. X-ray analysis of the SAPO-20 sample used in the adsorption studies established that the x-ray powder diffraction pattern was essentially unchanged as a result of the calcination and subsequent contact with the adsorbate species.

EXAMPLE 28

(Preparation of SAPO-20)

This preparation utilizes a reaction mixture which contains a significant amount of intentionally added sodium in the form of sodium aluminate. A first mixture was formed by combining a solution of 76.9 grams of 85 wt. % orthophosphoric acid ($H_3PO_4$) in 60.1 grams of water with 45.8 grams of a hydrated aluminum oxide (a pseudo-boehmite phase, 74.2 wt. % $Al_2O_3$, 25.8 wt. % $H_2O$) and stirring until homogeneous. To this mixture was added a solution of 192.3 grams of tetramethylammonium hydroxide pentahydrate (TMAOH5H$_2$O) in 121.1 grams of water and the mixture stirred until homogeneous. A second mixture was prepared by combining a solution of 23.5 grams of sodium aluminate (1.21Na$_2$O.Al$_2$O$_3$.3.2H$_2$O) in 38.0 grams of water with 80.1 grams of an aqueous sol of 30 wt. % SiO$_2$ and 8.2 additional grams of water. To this mixture was added 98.7 grams of the first-prepared mixture, and the resulting composition stirred until homogeneous. The composition of the final mixture in molar oxide ratios was:

1.1(TMA)$_2$O:4.0SiO$_2$:1.66Al$_2$O$_3$:0.66P$_2$O$_5$:1.-2Na$_2$O:95H$_2$O

Part of the reaction mixture was placed in a stainless steel pressure vessel lined with an inert plastic material and heated in an oven at 200° C. at autogenous pressure for 168 hours. The solid reaction product was recovered by centrifugation, washed with water, and dried in air at 100° C. The SAPO-20 product had an x-ray powder diffraction pattern essentially identical to that shown in Example 27 for the as-synthesized material. Chemical analysis showed 6.9 wt.-% C, 1.6 wt.-% N, 8.0 wt.-% Na$_2$O, 39.6 wt.-% SiO$_2$, 24.7 wt.-% Al$_2$O$_3$, 10.5 wt.-% P$_2$O$_5$, 16.6 wt.-% LOI, giving a product composition in molar oxide ratios of:

0.3(TMA)$_2$O:0.5Na$_2$O:2.7SiO$_2$:Al$_2$O$_3$:0.31P$_2$O$_5$:0.8-H$_2$O which corresponds to the formula (anhydrous basis):

0.113(TMA):(0.19Na):(Si$_{0.51}$Al$_{0.38}$P$_{0.12}$)O$_2$

EXAMPLE 29

(Preparation of SAPO-20)

SAPO-20 was produced in about 95% purity from a reaction mixture templated with tetramethylammonium hydroxide using aluminum isopropoxide as the source of alumina and a fumed silica as the silica source. The overall reaction mixture composition, in terms of molar oxide ratios, was:

0.5(TMA)$_2$O:0.1SiO$_2$:Al$_2$O$_3$:0.9P$_2$O$_5$:49H$_2$O

Crystallization was carried out at 150° C. for 133 hours under autogenous pressure. The X-ray powder pattern of the major product phase was essentially identcal to that in Example 27(a). The chemical composition of the product was 8.0 wt.-% C, 2.23 wt.-% N, 3.3 wt.-% SiO$_2$, 34.9 wt.-% Al$_2$O$_3$, 34.0 wt.-% P$_2$O$_5$, 21.5 wt.-% LOI, giving a product composition in molar oxide ratios of:

0.24(TMA)$_2$O:0.16SiO$_2$:Al$_2$O$_3$:0.70P$_2$O$_5$:1.1H$_2$O which corresponds to the formula (anhydrous basis)

0.13(TMA):(Si$_{0.05}$Al$_{0.56}$P$_{0.39}$)O$_2$

EXAMPLE 30

(Preparation of SAPO-20)

(a) A reaction mixture was prepared by adding 1.09 grams of a reactive amorphous precipitated silica (91.4 wt.-% SiO$_2$, 8.6 wt.-% H$_2$O) to a solution of 14.50 grams of tetramethylammonium hydroxide pentahydrate TMAOH.5H$_2$O in 20.0 grams of water, and mixed until homogeneous. To this mixture were added 6.12 grams of a hydrated aluminum oxide (a pseudo-boehmite phase, 74.2 wt.-% Al$_2$O$_3$, 25.8 wt.-% H$_2$O) and 9.55 grams of 85% orthophosphoric acid (H$_3$PO$_4$) and 6.21 grams of water and the mixture stirred until homogeneous. The composition of the final reaction mixture in molar oxide ratios was:

1.1Al$_2$O$_3$:1.0P$_2$O$_5$:1.0(TMA)$_2$O:0.4SiO$_2$:50.0H$_2$O

Part of the reaction mixture was placed in a stainless steel pressure vessel with an inert plastic liner and heated in an oven at 200° C. at autogenous pressure for 24 hours. The solid reaction product was recovered by filtering, washed with water, and dried in air at room temperature. The SAPO-20 product had an x-ray powder diffraction pattern characterized by the following data:

TABLE P

| 2θ | d | 100 × I/I$_o$ |
|---|---|---|
| 14.1 | 6.28 | 39 |
| 19.8 | 4.48 | 49 |
| 22.2 | 4.00 | 6 |
| 24.3 | 3.66 | 100 |
| 28.1 | 3.175 | 11 |
| 31.7 | 2.822 | 12 |
| 34.7 | 2.585 | 16 |
| 37.5 | 2.398 | 1 |
| 40.2 | 2.243 | 5 |
| 42.7 | 2.117 | 6 |
| 47.5 | 1.914 | 6 |
| 51.9 | 1.762 | 12 |

(b) Adsorption capacities were measured on this calcined (500° C. for one hour) product using a standard McBain-Bakr gravimetric adsorption apparatus. The following data were obtained on a sample activated at 350° C. in vacuum.

| | Kinetic Diameter, A | Pressure, Torr | Temp °C. | Wt. % Adsorbed |
|---|---|---|---|---|
| O$_2$ | 3.46 | 100 | −183 | 0 |
| O$_2$ | 3.46 | 750 | −183 | 0 |
| H$_2$O | 2.65 | 4.6 | 24 | 32.1 |
| H$_2$O | 2.65 | 20 | 24 | 39.8 |

The pore size of the calcined product is greater than 2.65 A as shown by adsorption of H$_2$O, kinetic diameter 2.65 A, and less than 3.46 A, as shown by no adsorption of O$_2$, kinetic diameter 3.46 A.

(c) The above product, after calcination and McBain adsorption studies, had an X-ray powder diffraction pattern characteristic of SAPO-20 (short scan).

| 2θ | d | 100 × I/I₀ |
|---|---|---|
| 14.0 | 6.33 | 100 |
| 19.8 | 4.48 | 38 |
| 22.2 | 4.00 | 8 |
| 24.3 | 3.663 | 95 |
| 28.2 | 3.164 | 23 |
| 31.5 | 2.840 | 18 |
| 34.6 | 2.592 | 20 |

(d) EDAX (energy dispersive analysis by X-ray) microprobe analysis performed in conjunction with SEM (scanning electron microscope) study, on clean crystals having a crystal morphology characteristic of SAPO-20 gives the following analysis, based on relative peak heights:

|  | Area Scan | Average of Spot Probes | Range |
|---|---|---|---|
| Si | 0.42 | 0.40 | 0.36–0.43 |
| Al | 1.0 | 1.0 | 1.0 |
| P | 0.77 | 0.79 | 0.76–0.85 |

EXAMPLE 31
(Preparation of SAPO-20)

SAPO-20 was successfully prepared using pyrrolidine as the templating agent in a reaction mixture containing aluminum isopropoxide and an aqueous silica sol as the source of alumina and silica respectively. Orthophosphoric acid was the phosphorus source. The overall reaction gel composition in terms of molar oxide ratios was:

$C_4H_9N:0.3SiO_2:Al_2O_3:P_2O_5:39H_2O$

The gel was crystallized at 200° C. for 48 hours. Chemical analysis showed 10.0 wt. % C, 2.2 wt. % N, 6.4 wt. % SiO₂, 32.6 wt. % Al₂O₃, 41.0 wt. % P₂O₅, 18.7 wt. % LOI, giving a product composition in molar oxide ratios of:

$0.325(C_4H_9N)_2O:0.33SiO_2:Al_2O_3:0.90P_2O_5:0.68H_2O$ which corresponds to the formula (anhydrous basis)

$0.16(C_4H_9N):(Si_{0.08}Al_{0.48}P_{0.44})O_2$

The species SAPO-20 as referred to herein is a silicoaluminophosphate material having a three-dimensional microporous crystal framework structure of $PO_2^+$, $AlO_2^-$ and $SiO_2$ tetrahedral units, and whose essential empirical chemical composition on an anhydrous basis is:

$mR:(Si_xAl_yP_z)O_2$ wherein "R" represents at least one organic templating agent present in the intracrystalline pore system; "m" represents the moles of "R" present per mole of $(Si_xAl_yP_z)O_2$ and has a value of from zero to 0.3, "x", "y" and "z" represent respectively, the mole fractions of silicon, aluminum and phosphorus present in the oxide moiety, said mole fractions being within the compositional area bounded by points A, B, C, D and E on the ternary diagram which is FIG. 1, or preferably within the area bounded by points a, b, c, d and e on the ternary diagram which is FIG. 2, said silicoaluminophosphate having a characteristic X-ray powder diffraction pattern which contains at least the d-spacings set forth below in Table IX. In the form as synthesized in accordance with the process of this invention, "m" has a value of from 0.02 to 0.3.

TABLE IX

| 2θ | d | Relative Intensity |
|---|---|---|
| 13.7–14.25 | 6.46–6.22 | m |
| 19.55–20.0 | 4.54–4.44 | w–m |
| 24.05–24.45 | 3.700–3.641 | vs |
| 34.35–35.0 | 2.611–2.564 | w |
| 42.5–43.0 | 2.127–2.103 | vw–w |

All of the as-synthesized SAPO-20 compositions for which X-ray powder diffraction data have presently been obtained have patterns which are within the generalized pattern of Table X, below.

TABLE X

| 2θ | d | 100 × I/I₀ |
|---|---|---|
| 13.7–14.25 | 6.46–6.22 | 38–63 |
| 19.55–20.0 | 4.54–4.44 | 25–58 |
| 21.9–22.35 | 4.06–3.98 | 0–9 |
| 24.05–24.45 | 3.700–3.641 | 100 |
| 27.85–28.55 | 3.203–3.126 | 8–17 |
| 31.25–31.8 | 2.862–2.814 | 5–16 |
| 34.35–35.0 | 2.611–2.564 | 12–22 |
| 37.3–37.5 | 2.411–2.398 | 0–3 |
| 39.9–40.4 | 2.259–2.233 | 2–6 |
| 42.5–43.0 | 2.127–2.103 | 3–24 |
| 47.25–47.8 | 1.924–1.903 | 2–8 |
| 51.6–52.2 | 1.771–1.752 | 2–17 |

EXAMPLE 32
(Preparation of SAPO-34)

In the preparation of SAPO-34, a reaction mixture was formed by combining 28.8 grams of 85 wt.% orthophosphoric acid (H₃PO₄) with a mixture of 17.2 grams of a hydrated aluminum oxide (a pseudo-boehmite phase, 74.2 wt.% Al₂O₃, 25.8 wt.% H₂O) in 18.4 grams of water. To this mixture was added 151.7 grams of an aqueous solution of 40.7 wt.% tetraethylammonium hydroxide (TEAOH) and the mixture stirred until homogeneous. To 81.9 grams of this mixture was added a solution of 11.7 grams of sodium aluminate (Al₂O₃:1.2-1Na₂O:3.2H₂O) in 23.0 grams of water and 40.0 grams of an aqueous sol of 30 wt.% SiO₂, and the mixture stirred until homogeneous. The composition of the final reaction mixture in molar oxide ratios was:

$1.6(TEA)_2O:1.2Na_2O:4SiO_2:2Al_2O_3:P_2O_5:112H_2O$

Part of the reaction mixture was sealed in a stainless steel pressure vessel having an inert plastic liner, and heated in an oven at 200° C. at autogenous pressure for 168 hours. The solid reaction product was recovered by filtration, washed with water, and dried in air at 110° C. The crystalline product was impure but the major phase, SAPO-34, had an X-ray powder diffraction pattern characterized by the following data:

TABLE Q

| 2θ | d | 100 × I/I₀ |
|---|---|---|
| 9.6 | 9.21 | 100 |
| 13.0 | 6.81 | 17 |
| 14.05 | 6.30 | 23 |
| 16.1 | 5.50 | 33 |
| 17.85 | 4.97 | 75 |
| 19.0 | 4.67 | 2 |
| 20.7 | 4.29 | 99 |
| 22.05 | 4.03 | 4 |
| 23.1 | 3.85 | 10 |
| 24.95 | 3.57 | 76 |
| 26.0 | 3.43 | 19 |
| 27.7 | 3.220 | 3 |
| 28.15 | 3.170 | 12* |
| 29.4 | 3.038 | 4 |
| 30.7 | 2.912 | 67 |
| 31.05 | 2.880 | 28 |
| 32.4 | 2.763 | 2 |
| 33.4 | 2.683 | 6 |
| 34.55 | 2.596 | 14 |
| 36.0 | 2.495 | 11 |
| 39.7 | 2.270 | 4 |
| 43.4 | 2.085 | 3 |
| 47.6 | 1.910 | 6 |
| 48.8 | 1.866 | 7 |
| 49.2 | 1.852 | 5 |
| 50.65 | 1.802 | 8 |
| 53.2 | 1.722 | 6 |
| 54.25 | 1.691 | 4 |
| 55.9 | 1.645 | 4 |

*contains peak from an impurity.

By chemical analysis, the composition of the solids product was established to be 2.8 wt.% C, 0.5 wt.% N, 37.0 wt.% $SiO_2$, 27.6 wt.% $Al_2O_3$, 12.2 wt.% $P_2O_5$, 7.4 wt.% $Na_2O$, 15.9 wt.% LOI, giving an overall product composition in molar oxide ratios of:

0.05(TEA)$_2$O:2.3SiO$_2$:0.4Na$_2$O:Al$_2$O$_3$:0.3P$_2$O$_5$:2.4-H$_2$O,

EXAMPLE 33

(Preparation of SAPO-34)

SAPO-34 exhibiting an X-ray powder diffraction pattern essentially identical with that set forth in Example 32, supra and having a chemical composition in terms of mole ratios of oxides 0.1(TEA)$_2$O:0.17SiO$_2$:Al$_2$O$_3$:0.69P$_2$O$_5$:1.5H$_2$O and a formula (anhydrous basis)

0.06(TEA):(Si$_{0.05}$Al$_{0.56}$P$_{0.39}$)O$_2$ was prepared as follows: A mixture of 90.7 grams of aluminum isopropoxide (Al(OC$_3$H$_7$)$_3$) and 160 grams of water was combined with 51.3 grams of 85 wt.% orthophosphoric acid (H$_3$PO$_4$) while stirring. To this mixture was added 1.4 grams of fumed silica (95 wt.% SiO$_2$, 5 wt.% water) and the mixture stirred until homogeneous. To one third by weight of this mixture was added 27.2 grams of an aqueous solution of 40 wt.% tetraethylammonium hydroxide (TEAOH), and the mixture stirred until homogeneous. The composition of the final reaction mixture in molar oxide ratios was:

0.5(TEA)$_2$O:0.1SiO$_2$:Al$_2$O$_3$:P$_2$O$_5$:57H$_2$O

The gel was crystallized at 150° C. for 133 hours at autogenous pressure, the product recovered by centrifugation, washed with water and dried in air at room temperature.

EXAMPLE 34

(Preparation of SAPO-34)

(a) Using the same reagents in Example 33, supra, except that the silica source was an aqueous silica sol rather than fumed silica, a reaction mixture was prepared having the composition:

0.5(TEA)$_2$O:0.6SiO$_2$:Al$_2$O$_3$:P$_2$O$_5$:52H$_2$O

This composition was crystallized under autogenous pressure at 200° C. for 48 hours to yield SAPO-34 as evidenced by its X-ray powder diffraction pattern which was characterized by the following data:

TABLE R

| 2θ | d | 100 × I/I₀ |
|---|---|---|
| 9.5 | 9.31 | 100 |
| 12.9 | 6.86 | 11 |
| 14.05 | 6.30 | 10 |
| 16.05 | 5.52 | 50 |
| 18.0 | 4.93 | 11 |
| 20.6 | 4.31 | 73 |
| 22.3 | 3.99 | 2 |
| 23.1 | 3.85 | 3 |
| 25.2 | 3.53 | 14 |
| 25.85 | 3.446 | 14 |
| 27.6 | 3.232 | 2 |
| 28.3 | 3.153 | 1 |
| 29.5 | 3.028 | 4 |
| 30.55 | 2.926 | 24 |
| 31.2 | 2.867 | 18 |
| 32.35 | 2.767 | 2 |
| 33.8 | 2.652 | 1 |
| 34.4 | 2.607 | 4 |
| 36.35 | 2.471 | 2 |
| 38.8 | 2.321 | 1 |
| 39.6 | 2.276 | 3 |
| 43.3 | 2.090 | 3 |
| 47.5 | 1.914 | 2 |
| 49.0 | 1.859 | 6 |
| 50.2 | 1.817 | 1 |
| 51.0 | 1.791 | 3 |
| 53.05 | 1.726 | 3 |
| 54.45 | 1.685 | 1 |
| 55.8 | 1.647 | 4 |

EDAX (energy dispersive analysis by X-ray) microprobe analysis, performed in conjunction with SEM (scanning electron microscope) study, on clean crystals having a crystal morphology characteristic of SAPO-34 gives the following analysis based on relative peak heights:

Si: 0.3
Al: 1.0
P: 0.8

(b) A substantially identical reaction mixture composition as in part (a) above, formed from the same reagents and crystallized at 150° C. for 336 hours yielded a SAPO-34 product having the chemical composition 10.2 wt.% C, 1.5 wt.% N, 34.4 wt.% Al$_2$O$_3$, 38.3 wt.% P$_2$O$_5$, 7.7 wt.% SiO$_2$ and 19.9 wt.% LOI. This corresponds to a composition in terms of molar oxide ratios of 0.16(TEA)$_2$O:0.38SiO$_2$:Al$_2$O$_3$:0.80P$_2$O$_5$:0.70H$_2$O which in turn corresponds to the formula (anhydrous basis)

0.08(TEA).(Si$_{0.10}$Al$_{0.50}$P$_{0.40}$)O$_2$

EXAMPLE 35

(Preparation of SAPO-34)

(a) A reaction mixture was prepared by combining 81.7 grams of aluminum isopropoxide ($Al(OC_3H_7)_3$) with a solution of 46.1 grams of 85 wt.% orthophosphoric acid in 104.9 grams of water, while stirring. To this mixture were added 12 grams of an aqueous sol of 30 wt.% $SiO_2$ and 5 grams of water, and the mixture stirred until homogeneous. To this mixture was added 73.7 grams of an aqueous solution of 40 wt.% tetraethylammonium hydroxide (TEAOH). One half by weight of this mixture was combined with 36.8 grams of 40% TEAOH, and the mixture stirred until homogeneous. The composition of the final reaction mixture in molar oxide ratios was:

$(TEA)_2O : 0.3 SiO_2 : Al_2O_3 : P_2O_5 : 50.0 H_2O$

The reaction mixture was placed in a stainless steel pressure vessel lined with an inert plastic material (polytetrafluoroethylene) and heated in an oven at 200° C. at autogeneous pressure for 120 hours. The solid reaction product (SAPO-34) was recovered by centrifugation, washed with water, and dried in air at 100° C. By chemical analysis, the product was established to comprise 10.5 wt.% C, 1.6 wt.% N, 34.1 wt.% $Al_2O_3$, 39.2 wt.% $P_2O_5$, 6.8 wt.% $SiO_2$ and 19.2 wt.% LOI, giving a product composition in molar oxide ratios of:

$0.17(TEA)_2O : 0.33 SiO_2 : Al_2O_3 : 0.82 P_2O_5 : 0.40 H_2O$, which corresponds to the formula (anhydrous basis)

$0.09(TEA) \cdot (Si_{0.08}Al_{0.51}P_{0.41})O_2$

The above product had an X-ray powder diffraction pattern essentially identical to that in Example 32.

(b) A portion of the solid crystalline SAPO-34 of part (a) was calcined in air at 550° C. for 2 hours. Adsorption capacities were measured on this calcined product using a standard McBain-Bakr gravimetric adsorption apparatus. The following data were obtained on a sample activated at 350° C.

|  | Kinetic Diameter, A | Pressure, Torr | Temp., °C. | Wt. % Adsorbed |
|---|---|---|---|---|
| $O_2$ | 3.46 | 104 | −183 | 25.1 |
| $O_2$ | 3.46 | 746 | −183 | 36.6 |
| n-Hexane | 4.3 | 46 | 23.4 | 11.0 |
| $H_2O$ | 2.65 | 4.6 | 23.0 | 30.1 |
| $H_2O$ | 2.65 | 19.5 | 22.8 | 42.3 |

The pore size of the calcined product is greater than 4.3 A, as shown by adsorption of n-hexane, kinetic diameter of 4.3 A.

(c) The product after McBain adsorption studies had an X-ray powder diffraction pattern characterized by the following data:

TABLE S

| 2θ | d | 100 × I/I₀ |
|---|---|---|
| 9.45 | 9.36 | 100 |
| 12.95 | 6.84 | 25 |
| 14.0 | 6.33 | 5 |
| 16.1 | 5.50 | 27 |
| 16.9 | 5.25 | 3 |
| 17.7 | 5.01 | 9 |
| 19.05 | 4.66 | 3 |

TABLE S-continued

| 2θ | d | 100 × I/I₀ |
|---|---|---|
| 20.75 | 4.28 | 55 |
| 21.25 | 4.18 | 1 |
| 22.0 | 4.04 | 3 |
| 22.55 | 3.94 | 2 |
| 23.15 | 3.84 | 4 |
| 24.8 | 3.59 | 21 |
| 25.05 | 3.555 | 11 |
| 27.8 | 3.209 | } 4 |
| 28.1 (sh) | 3.175 | |
| 29.6 | 3.018 | 3 |
| 30.8 | 2.903 | 26 |
| 31.6 | 2.831 | 2 |
| 32.3 | 2.772 | 2 |
| 33.3 | 2.691 | 2 |
| 34.7 | 2.585 | 4 |
| 35.85 | 2.505 | 4 |
| 38.6 | 2.332 | 1 |
| 39.85 | 2.262 | 2 |
| 42.7 | 2.118 | 2 |
| 43.5 | 2.080 | 2 |
| 47.05 | 1.932 | 1 |
| 47.9 | 1.899 | 2 |
| 48.8 | 1.866 | 4 |
| 50.5 | 1.807 | 3 |
| 51.9 | 1.762 | 1 |
| 53.4 | 1.716 | 2 |
| 54.15 | 1.694 | 2 |
| 54.6 | 1.681 | 1 |

EXAMPLE 36

(Preparation of SAPO-34)

(a) Isopropylamine (i-$PrNH_2$) was successfully employed to template the formation of SAPO-34 in a reaction mixture having the composition:

i-$PrNH_2 : 0.6 SiO_2 : Al_2O_3 : P_2O_5 : 50 H_2O$ and formed from aluminum isopropoxide, an aqueous silica sol, orthophosphoric acid and water. The reaction gel was crystallized at 200° C. for 51 hours at autogenous pressure. X-ray analysis confirmed the formation of SAPO-34.

(b) A portion of the solid crystalline product of part (a) above was calcined in air for 3.5 hours at about 600° C. The major species of the calcined product had an X-ray powder diffraction pattern essentially identical with that of Example 34(a).

(c) Adsorption capacities were measured on the calcined product of part (b) using a standard McBain-Bakr adsorption apparatus. The following data were obtained on a sample activted at 350° C.

|  | Kinetic Diameter, A | Pressure, Torr | Temp., °C. | Wt. % Adsorbed |
|---|---|---|---|---|
| $O_2$ | 3.46 | 98 | −183 | 15.0 |
| $O_2$ | 3.46 | 746 | −183 | 21.7 |
| n-hexane | 4.3 | 97 | 24 | 3.7 |
| isobutane | 5.0 | 402 | 26 | 0.2 |
| $H_2O$ | 2.65 | 4.6 | 22 | 18.7 |
| $H_2O$ | 2.65 | 19.4 | 24 | 23.7 |

The pore side of the calcined product is >4.3 and <5.0 A as shown by the adsorption of n-hexane, kinetic diameter of 4.3 A, and negligible adsorption of isobutane, kinetic diameter of 5.0 A.

EXAMPLE 37

(Preparation of SAPO-34)

(a) SAPO-34 was crystallized from a system containing a mixture of two organic templating agents by combining orthophosphoric acid, a hydrated aluminum oxide, a fumed silica, water, tetraethylammonium hydroxide and di-n-propylamine to form a reaction mixture having a composition in terms of molar ratios of oxides of:

$Al_2O_3:P_2O_5:0.6SiO_2:0.5(TEA)_2O:1.5(Pr_2NH):50\ H_2O$

After digestion and crystallization at 200° C. for 24 hours, the recovered product was identified by X-ray analysis to be essentially SAPO-34 and to have a chemical composition of 33.0 wt.-% $Al_2O_3$, 34.4 wt.-% $P_2O_5$, 10.3 wt.-% $SiO_2$, 11.1 wt.-% C, 1.7 wt.-% N and 21.3 wt.-% loss on ignition (LOI).

(b) A portion of the product of part (a) supra was calcined at 600° C. for 1 hour, and adsorption capacities determined using a standard McBain-Bakr gravimetric adsorption apparatus. The following data were obtained on a sample activated at 350° C.

|  | Kinetic Diameter, A | Pressure, Torr | Temp., °C. | Wt. % Adsorbed |
|---|---|---|---|---|
| $O_2$ | 3.46 | 100 | −183 | 25.5 |
| $O_2$ | 3.46 | 753 | −183 | 34.8 |
| Cyclohexane | 6.0 | 58 | 24.4 | 2.0 |
| Neopentane | 6.2 | 745 | 24.5 | 1.7 |
| $H_2O$ | 2.65 | 4.6 | 24.2 | 28.6 |
| $H_2O$ | 2.65 | 22.0 | 24.2 | 34.9 |
| n-Hexane | 4.3 | 45.0 | 24.4 | 11.9 |

EXAMPLE 38

(Preparation of SAPO-34)

SAPO-34 was crystallized from a reaction system containing both sodium and TEA ions prepared by combining 66.4 grams of aluminum isopropoxide with a solution of 28.8 grams of 85 wt.-% orthophosphoric acid in 70.1 grams of $H_2O$. To this mixture was added a mixture of 15.0 grams of an aqueous silica sol (30 wt.-% $SiO_2$) and a solution of 3.0 grams of NaOH in 10.0 grams $H_2O$. Thereafter 46.0 grams of an aqueous solution of 40 wt.-% tetraethylammonium hydroxide was added and the mixture stirred until homogeneous. The composition of the final mixture was:

$0.5(TEA)_2O:0.3Na_2O:1.3Al_2O_3:0.6SiO_2:P_2O_5:60\ H_2O$

After crystallization in a sealed reactor at 200° C. for 187 hours, the SAPO-34 product (identified by X-ray analysis) had a chemical composition: 4.5 wt.-% C, 37.7 wt.-% $Al_2O_3$, 22.9 wt.-% LOI, 29.5 wt.-% $P_2O_5$, 4.9 wt.-% $Na_2O$ and 4.5 wt.-% $SiO_2$.

The species SAPO-34 as referred to herein is a silicoaluminophosphate material having a three-dimensional microporous crystal framework structure of $PO_2^+$, $AlO_2^-$ and $SiO_2$ tetrahedral units, and whose essential empirical chemical composition in the as-synthesized form and on an anhydrous basis is:

$mR:(Si_xAl_yP_z)O_2$ wherein "R" represents at least one organic templating agent present in the intracrystalline pore system; "m" represents the moles of "R" present per mole of $(Si_xAl_yP_z)O_2$ and has a value of from 0.02 to 0.3, "x", "y" and "z" represent respectively, the mole fractions of silicon, aluminum and phosphorus present in the oxide moiety, said mole fractions being within the compositional area bounded by points A, B, C, D and E on the ternary diagram which is FIG. 1, or preferably within the area bounded by points a, b, c, d and e on the ternary diagram which is FIG. 2, said silicoaluminophosphate having a characteristic X-ray powder diffraction pattern which contains at least the d-spacings set forth below in Table XI.

TABLE XI

| 2θ | d | Relative Intensity |
|---|---|---|
| 9.45–9.65 | 9.36–9.17 | s–vs |
| 16.0–16.2 | 5.54–5.47 | w–m |
| 17.85–18.15 | 4.97–4.89 | w–s |
| 20.55–20.9 | 4.32–4.25 | m–vs |
| 24.95–25.4 | 3.57–3.51 | w–s |
| 30.5–30.7 | 2.931–2.912 | w–s |

All of the as-synthesized SAPO-34 compositions for which X-ray powder diffraction data have presently been obtained have patterns which are within the generalized pattern of Table XII, below.

TABLE XII

| 2θ | d | 100 × $I/I_o$ |
|---|---|---|
| 9.45–9.65 | 9.36–9.17 | 81–100 |
| 12.8–13.05 | 6.92–6.78 | 8–20 |
| 13.95–14.2 | 6.35–6.24 | 8–23 |
| 16.0–16.2 | 5.54–5.47 | 25–54 |
| 17.85–18.15 | 4.97–4.89 | 11–76 |
| 19.0 | 4.67 | 0–2 |
| 20.55–20.9 | 4.32–4.25 | 44–100 |
| 22.05–22.5 | 4.03–3.95 | 0–5 |
| 23.0–23.15 | 3.87–3.84 | 2–10 |
| 24.95–25.4 | 3.57–3.51 | 12–87 |
| 25.8–26.0 | 3.45–3.43 | 14–26 |
| 27.5–27.7 | 3.243–3.220 | 1–4 |
| 28.05–28.4 | 3.181–3.143 | 1–12 |
| 29.2–29.6 | 3.058–3.018 | 3–9 |
| 30.5–30.7 | 2.931–2.912 | 19–75 |
| 31.05–31.4 | 2.880–2.849 | 15–28 |
| 32.2–32.4 | 2.780–2.763 | 1–5 |
| 33.4–33.85 | 2.683–2.648 | 0–6 |
| 34.35–34.65 | 2.611–2.589 | 4–15 |
| 36.0–36.5 | 2.495–2.462 | 2–11 |
| 38.8–38.9 | 2.321–2.315 | 0–2 |
| 39.6–39.7 | 2.276–2.270 | 2–4 |
| 43.1–43.5 | 2.099–2.080 | 3–6 |
| 47.4–47.7 | 1.918–1.907 | 2–6 |
| 48.8–49.2 | 1.866–1.852 | 4–7 |
| 49.9–50.45 | 1.828–1.809 | 0–2 |
| 50.65–51.3 | 1.802–1.781 | 1–8 |
| 53.0–53.25 | 1.728–1.720 | 2–7 |
| 54.25–54.7 | 1.691–1.678 | 0–4 |
| 55.7–55.9 | 1.650–1.645 | 2–5 |

EXAMPLE 39

(Preparation of SAPO-35)

SAPO-35 was synthesized from a reaction mixture which contained quinuclidine as the templating agent and which had an overall composition in terms of molar oxide ratios:

$4.0C_7H_{13}N:0.3SiO_2:Al_2O_3:P_2O_5:75H_2O$

This reaction mixture was prepared by combining 46.1 grams of 85 wt.% orthophosphoric acid (H$_3$PO$_4$) and 60.9 grams of water with 81.7 grams of aluminum isopropoxide (Al(OC$_3$H$_7$)$_3$) while stirring. To this mixture were added 12 grams of an aqueous sol of 30 wt.% SiO$_2$ and 5 grams of water, and the mixture stirred until homogeneous. To 87.4 grams of this mixture were added 37.8 grams of quinuclidine, C$_7$H$_{13}$N, (Q), and 75.1 grams H$_2$O, and the mixture stirred until homogeneous. A portion of the reaction mixture was sealed in a stainless steel reaction vessel having an inert liner and heated in an oven at 200° C. at autogeneous pressure for 168 hours. The solid reaction product was recovered by centrifugation, washed with water, and dried in air at 100° C. The product had an X-ray powder diffraction pattern characterized by the following data:

TABLE T

| 2θ | d | 100 × I/I$_o$ |
|---|---|---|
| 8.7 | 10.1 | 18 |
| 11.05 | 8.01 | 47 |
| 11.9 | 7.44 | 2 |
| 13.4 | 6.61 | 23 |
| 16.0 | 5.54 | 12 |
| 17.4 | 5.10 | } 83 |
| 17.7 (sh) | 5.01 | |
| 17.9 | 4.96 | 14 |
| 21.25 | 4.18 | 55 |
| 22.0 | 4.04 | 100 |
| 22.8 | 3.90 | 5 |
| 23.3 | 3.82 | 18 |
| 23.7 | 3.75 | 6 |
| 25.2 | 3.53 | 5 |
| 26.0 | 3.427 | 1 |
| 26.9 | 3.314 | 18 |
| 28.55 | 3.126 | 26 |
| 28.65 | 3.116 | 13 |
| 29.1 | 3.069 | 6 |
| 32.15 | 2.784 | 40 |
| 34.65 | 2.589 | 9 |
| 35.7 | 2.515 | 3 |
| 37.8 | 2.380 | 2 |
| 39.3 | 2.292 | 2 |
| 40.8 | 2.212 | 2 |
| 42.1 | 2.146 | 4 |
| 42.4 | 2.132 | 4 |
| 43.15 | 2.096 | 4 |
| 44.4 | 2.040 | 2 |
| 48.5 | 1.877 | 7 |
| 49.4 | 1.845 | 6 |
| 51.5 | 1.774 | 7 |
| 55.2 | 1.664 | 7 |

(b) EDAX (energy dispersive analysis by X-ray) microprobe analysis, performed in conjunction with SEM (scanning electron microscope) study, on clean crystals of SAPO-35 gives the following analysis based on relative peak heights:
Si: 0.2
Al: 1.0
P: 0.7–0.8

EXAMPLE 40

(Preparation of SAPO-35)

(A) A reaction mixture was prepared by combining 132 grams of water with 132.8 grams of aluminum isopropoxide (Al(OC$_3$H$_7$)$_3$) and then adding 30.1 grams of an aqueous sol containing 30 wt.% SiO$_2$ and 45 grams of water. To this mixture was added 57.7 grams of 85 wt.% orthophosphoric acid (H$_3$PO$_4$) and the mixture stirred until homogeneous. To this mixture was added a solution of 27.8 grams of quinuclidine, C$_7$H$_{13}$N, (Q) in 50 grams of water, and the mixture stirred until homogeneous. The composition of the final reaction mixture in molar oxide ratios was:

1.0Q:0.6SiO$_2$:1.3Al$_2$O$_3$:P$_2$O$_5$:60H$_2$O

Part of the reaction mixture was placed in a stainless steel pressure vessel lined with polytetrafluoroethylene and heated in an oven at 150° C. at autogenous pressure for 48 hours. The solid reaction product was recovered by centrifugation, washed in water, and dried in air at 100° C. The above product was impure but the major phase had an X-ray powder diffraction pattern essentially identical to that in Example 39.

(b) A portion of the solid crystalline product was calcined in air at about 600° C. for 2 hours. The whiter portion of the calcined product had an X-ray powder pattern characterized by the following data:

TABLE U

| 2θ | d | 100 × I/I$_o$ |
|---|---|---|
| 6.8 | 13.0 | 2 |
| 8.2 | 10.78 | 2 |
| 8.7 | 10.16 | 14 |
| 11.0 | 8.04 | 100 |
| 11.4 | 7.76 | 17 |
| 13.55 | 6.53 | 89 |
| 16.1 | 5.50 | 4 |
| 17.4 | 5.10 | 24 |
| 18.7 | 4.75 | 3 |
| 21.0 | 4.23 | 29 |
| 22.2 | 4.00 | 63 |
| 23.0 | 3.87 | 4 |
| 23.6 | 3.77 | 15 |
| 25.05 | 3.555 | 13 |
| 26.0 | 3.427 | 9 |
| 27.3 | 3.267 | 20 |
| 28.6 | 3.121 | 42 |
| 29.5 | 3.028 | 10 |
| 30.6 | 2.921 | 2 |
| 31.75 | 2.818 | 6 |
| 32.4 sh | 2.763 | } 32 |
| 32.6 | 2.747 | |
| 34.6 | 2.592 | 7 |
| 35.4 | 2.536 | 4 |
| 36.3 | 2.475 | 2 |
| 47.9 | 1.899 | 2 |
| 51.7 | 1.768 | 3 |

(c) Adsorption capacities were measured on this calcined product using a standard McBain-Bakr gravimetric adsorption apparatus. The following data were obtained on a sample activated at 350° C:

| | Kinetic Diameter, Å | Pressure, Torr | Temp., °C. | Wt. % Adsorbed |
|---|---|---|---|---|
| O$_2$ | 3.46 | 98 | −183 | 15.3 |
| O$_2$ | 3.46 | 746 | −183 | 30.3 |
| isobutane | 5.0 | 101 | 25 | 0.7 |
| n-hexane | 4.3 | 48 | 24 | 10.2 |
| H$_2$O | 2.65 | 4.6 | 22 | 22.2 |
| H$_2$O | 2.65 | 19 | 24 | 47.7 |

The pore size of the calcined product is >4.3 Å and <5.0 Å as shown by adsorption of n-hexane, kinetic diameter of 4.3 Å, and negligible adsorption of isobutane, kinetic diameter of 5.0 Å.

EXAMPLE 41

(Preparation of SAPO-35)

(a) A reaction mixture was prepared by combining 66.4 grams of aluminum isopropoxide and 67.8 grams H$_2$O, to which was added a mixture of 15.0 grams of an aqueous silica sol (30 wt.-% SiO2) and a solution of 3.0 grams NaOH in 20 grams H2O and the mixture stirred until homogeneous. To this mixture was added 28.8 grams of 85 wt.-% orthophosphoric acid to which had been added a solution of 13.9 grams of quinuclidine (C7H13N) in 25 grams of H2O. The final homogeneous reaction mixture had a chemical composition in terms of molar oxide ratios of:

0.5(C7H13N)2O:0.3Na2O:0.60SiO2:1.3Al2O3:-P2O5:60H2O

The reaction mixture was crystallized at 150° C. under autogenous pressure in a sealed reactor for 187 hours. The X-ray pattern of the recovered crystalline SAPO-35 product was essentially identical to that of the SAPO-35 composition of Example 40, supra. Chemical analysis showed 3.7 wt.-% C, 4.4 wt.-% SiO2, 4.8 wt.-% Na2O, 39.5 wt.-% Al2O3, 28.4 wt.-% P2O5, 22.5 wt.-% LOI, giving a composition in terms of molar oxide ratios of:

0.055(C7H13N)2O:0.20Na2O:Al2O3:0.19SiO2:0.52-P2O5:2.52H2O which corresponds to an essential empirical formula (anhydrous basis) of:

0.034C7H13N:(Si0.06Al0.62P0.32)O2

(b) Using the same reagents as in part (a) above, except that sodium was omitted, a reaction mixture was prepared having a composition in terms of molar oxide ratios:

0.5(C7H13N)2O:0.4SiO2:1.2Al2O3:P2O5:60H2O

This mixture was digested and crystallized for 160 hours at 150° C. in a sealed reactor. The X-ray powder diffraction pattern of the recovered product was essentially identical to that of the product of part (a) above. The chemical composition of the product was (anhydrous basis):

0.4C7H13N:0.23SiO2:Al2O3:0.64P2O5 corresponding to an essential empirical formula of:

0.11C7H13N:(Si0.07Al0.57P0.36)O2

The species SAPO-35 as referred to herein is a silicoaluminophosphate material having a three-dimensional microporous crystal framework structure of PO2+, AlO2− and SiO2 tetrahedral units, and whose essential empirical chemical composition on an anhydrous basis is:

mR:(Si$_x$Al$_y$P$_z$)O2 wherein "R" represents at least one organic templating agent present in the intracrystalline pore system; "m" represents the moles of "R" present per mole of (Si$_x$Al$_y$P$_z$)O2 and has a value of from zero to 0.3, "x", "y" and "z" represent respectively, the mole fractions of silicon, aluminum and phosphorus present in the oxide moiety, said mole fractions being within the compositional area bounded by points A, B, C, D and E on the ternary diagram which is FIG. 1, or preferably within the area bounded by points a, b, c, d and e on the ternary diagram which is FIG. 2, said silicoaluminophosphate having a characteristic X-ray powder diffraction pattern which contains at least the d-spacings set forth below in Table XIII. In the form as synthesized in accordance with the process of this invention, "m" has a value of from 0.02 to 0.3.

TABLE XIII

| 2θ | d | Relative Intensity |
|---|---|---|
| 10.9–11.05 | 8.12–8.01 | m |
| 17.2–17.4 | 5.16–5.10 | |
| 17.4–17.7 (sh) | 5.10–5.01 | s |
| 21.0–21.25 | 4.23–4.18 | m |
| 21.8–22.0 | 4.08–4.04 | vs |
| 32.0–32.15 | 2.797–2.784 | m |

All of the as-synthesized SAPO-35 compositions for which X-ray powder diffraction data have presently been obtained have patterns which are within the generalized pattern of Table XIV, below.

TABLE XIV

| 2θ | d | 100 × I/I$_o$ |
|---|---|---|
| 8.5–8.7 | 10.4–10.1 | 13–18 |
| 10.9–11.05 | 8.12–8.01 | 38–48 |
| 11.6–11.9 | 7.63–7.44 | 1–3 |
| 13.2–13.4 | 6.71–6.61 | 23–24 |
| 15.75–16.0 | 5.62–5.54 | 7–12 |
| 17.2–17.4 | 5.16–5.10 | |
| 17.4–17.7 (sh) | 5.10–5.01 | 66–83 |
| 17.6–17.9 | 5.04–4.96 | 9–18 |
| 21.0–21.25 | 4.23–4.18 | 47–56 |
| 21.8–22.0 | 4.08–4.04 | 100 |
| 23.0–23.3 | 3.87–3.82 | 14–18 |
| 23.55–23.75 | 3.78–3.75 | 6 |
| 24.9–25.2 | 3.58–3.53 | 3–6 |
| 25.85–26.0 | 3.446–3.427 | 0–2 |
| 26.7–26.9 | 3.339–3.314 | 16–19 |
| 28.4–28.55 | 3.143–3.126 | 22–26 |
| 28.65–28.85 | 3.116–3.095 | 13–20 |
| 29.0–29.1 | 3.079–3.069 | 4–6 |
| 32.0–32.15 | 2.797–2.784 | 33–47 |
| 34.55–34.7 | 2.596–2.585 | 6–9 |
| 35.6–35.8 | 2.522–2.508 | 3–4 |
| 37.7–37.8 | 2.386–2.380 | 2–3 |
| 39.2–39.3 | 2.298–2.292 | 2 |
| 40.7–40.8 | 2.217–2.212 | 0–2 |
| 41.95–42.1 | 2.154–2.146 | 3–5 |
| 42.4–42.55 | 2.132–2.125 | 2–4 |
| 42.95–43.2 | 2.106–2.094 | 2–4 |
| 44.4–44.5 | 2.040–2.036 | 1–2 |
| 48.4–48.55 | 1.881–1.875 | 7–8 |
| 49.3–49.45 | 1.848–1.843 | 6–8 |
| 51.4–51.5 | 1.778–1.774 | 5–8 |
| 55.2—55.25 | 1.664–1.663 | 4–7 |

EXAMPLE 42

(Preparation of SAPO 37)

A SAPO-37 was synthesized from a reaction mixture prepared by combining 9.2 grams of 85 wt.% orthophosphoric acid (H3PO4) and 5.8 grams of water, to which was added 5.5 grams of hydrated aluminum oxide (a pseudo-boehmite phase, 74.2 wt.% Al2O3, 25.8 wt.% H2O), and stirred until homogeneous. To this mixture was added a dispersion of 1.0 gram of fumed silica (92.8 wt.% SiO2, 7.2 wt.% H2O) in 40.8 grams of an aqueous solution of 40% tetra-n-propylammonium hydroxide (TPAOH). The mixture was stirred until homogeneous. The composition of the final reaction mixture in molar oxide ratios was:

Al$_2$O$_3$:P$_2$O$_5$:0.4SiO$_2$:(TPA)$_2$O:50H$_2$O

A portion of this mixture was crystallized at 200° C. for 24 hours under autogeneous pressure in a sealed reactor lined with an inert plastic material. The solid reaction product was recovered by centrifuging and washing with water, and dried in air at room temperature. The SAPO-37 product was impure but the major phase (~80%) had an X-ray powder diffraction pattern characterized by the following data:

TABLE VA

| 2θ | d | 100 × I/I$_o$ |
|---|---|---|
| 6.24 | 14.17 | 100 |
| 10.17 | 8.69 | 22 |
| 11.93 | 7.42 | 4 |
| 15.69 | 5.65 | 33 |
| 18.73 | 4.74 | 20 |
| 20.405 | 4.35 | 13 |
| 21.08 | 4.21 | 5 |
| 22.84 | 3.89 | 8 |
| 23.69 | 3.75 | 24 |
| 24.67 | 3.61 | 1 |
| 25.85 | 3.45 | 6 |
| 27.09 | 3.29 | 14 |
| 27.84 | 3.204 | 2 |
| 29.69 | 3.009 | 3 |
| 30.80 | 2.903 | 5 |
| 31.45 | 2.844 | 12 |
| 32.50 | 2.755 | 3 |
| 33.14 | 2.703 | 1 |
| 34.14 | 2.626 | 5 |
| 34.45 | 2.603 | 2 |
| 37.94 | 2.371 | 3 |
| 40.61 | 2.221 | 1 |
| 41.46 | 2.178 | 1 |
| 43.29 | 2.089 | 1 |
| 44.10 | 2.054 | 2 |

By chemical analysis the composition of the SAPO-37 product was found to be 12.1 wt.% C, 1.43 wt.% N, 8.98 wt.% SiO$_2$, 33.08 wt.% Al$_2$O$_3$, 33.69 wt.% P$_2$O$_5$, 24.25 wt.% LOI (by difference), giving a product composition in molar oxide ratios of:

0.13(TPA)$_2$O:0.46SiO$_2$:Al$_2$O$_3$:0.74P$_2$O$_5$:1.23H$_2$O which corresponds to the formula (anhydrous basis)

0.066(TPA):(Si$_{0.12}$Al$_{0.51}$P$_{0.37}$)O$_2$

EDAX (energy dispersive analysis by X-ray) microprobe analysis, performed in conjunction with SEM (scanning electron microscope) study, on clean crystals having a crystal morphology characteristic of SAPO-37 gives the following analysis based on relative peak heights:

|  | Range | Average |
|---|---|---|
| Si | 0.43–0.47 | 0.45 |
| Al | 1.0 | 1.0 |
| P | 0.76–0.82 | 0.795 |

EXAMPLE 43

(Preparation of SAPO-37)

(a) SAPO-37 was found to be suitably templated by a mixture of tetra-n-propylammonium ions and tetramethylammonium ions in a reaction mixture formed by combining 27.7 grams of 85 wt.% orthophosphoric acid (H$_3$PO$_4$) and 30.5 grams of water, to which was added 16.6 grams of hydrated aluminum oxide (a pseudo-boehmite phase, 74.2 wt.% Al$_2$O$_3$, 25.8 wt.% H$_2$O), and stirred until homogeneous. To this mixture was added a dispersion of 3.1 grams of a fumed silica (92.8 wt.% SiO$_2$, 7.2 wt.% H$_2$O) and 1.1 gram of tetramethylammonium hydroxide pentahydrate (TMAOH 5.H$_2$O) in 115.98 grams of an aqueous solution of 40 wt.% tetra-n-propylammonium hydroxide (TPAOH) and the mixture stirred until homogeneous. The composition of the final reaction mixture in molar oxide ratios was:

Al$_2$O$_3$:P$_2$O$_5$:0.4SiO$_2$:(TPA)$_2$O:0.025(TMA)$_2$O:50H$_2$O

A portion of the reaction mixture was placed in a stainless steel pressure vessel lined with polytetrafluoroethylene and heated in an oven at 200° C. at autogeneous pressure for 24 hours. The solid reaction product was recovered by centrifuging and washing with water, and dried in air at 100° C. The above product had an X-ray powder diffraction pattern characterized by the following data:

TABLE W

| 2θ | d | 100 × I/I$_o$ |
|---|---|---|
| 6.2 | 14.25 | 100 |
| 10.1 | 8.74 | 22 |
| 11.9 | 7.44 | 5 |
| 15.6 | 5.68 | 42 |
| 18.5 | 4.80 | 34 |
| 20.2 | 4.40 | 16 |
| 21.2 | 4.19 | 4 |
| 22.7 | 3.92 | 11 |
| 23.5 | 3.79 | 39 |
| 24.8 | 3.59 | 1 |
| 25.7 | 3.47 | 6 |
| 26.9 | 3.314 | 27 |
| 27.6 | 3.232 | 2 |
| 29.4 | 3.038 | 7 |
| 30.6 | 2.921 | 9 |
| 31.2 | 2.867 | 18 |
| 32.2 | 2.780 | 5 |
| 33.0 | 2.714 | 2 |
| 33.9 | 2.644 | 7 |
| 34.4 | 2.607 | 3 |
| 37.8 | 2.380 | 6 |
| 40.4 | 2.233 | 2 |
| 41.2 | 2.191 | 2 |
| 43.1 | 2.099 | 1 |
| 43.9 | 2.062 | 3 |

The chemical composition of the SAPO-37 product was determined to be 31.8 wt.% Al$_2$O$_3$, 31.4 wt.% P$_2$O$_5$, 9.2 wt.% SiO$_2$, 14.2 wt.% C, 1.8 wt.% N and 26.1 wt.% LOI, corresponding to a product composition in molar oxide ratios of:

1.0Al$_2$O$_3$:0.71P$_2$O$_5$:0.49SiO$_2$:0.13(TPA)$_2$O:0.07(TMA)$_2$O:0.89H$_2$O, and thus had the formula (anhydrous basis):

0.10(TPA+TMA):(Si$_{0.125}$Al$_{0.51}$P$_{0.365}$)O$_2$ (b) A portion of the solid crystalline product of part (a) was calcined in air at about 600° C. for 1 hour. The calcined product had an X-ray powder diffraction pattern characterized by the data shown in the following table:

TABLE Y

| 2θ | d | 100 × I/I$_o$ |
|---|---|---|
| 6.2 | 14.25 | 100 |
| 10.3 | 8.59 | 19 |

TABLE Y-continued

| 2θ | d | 100 × I/I₀ |
|---|---|---|
| 12.1 | 7.37 | 11 |
| 15.9 | 5.57 | 20 |
| 18.6 | 4.77 | 7 |
| 20.4 | 4.35 | 9 |
| 21.5 | 4.13 | 1 |
| 22.9 | 3.88 | 3 |
| 23.8 | 3.74 | 13 |
| 25.0 | 3.56 | 1 |
| 25.8 | 3.45 | 1 |
| 27.0 | 3.30 | 7 |
| 27.7 | 3.22 | 1 |
| 29.5 | 3.03 | 2 |
| 30.7 | 2.92 | 4 |
| 31.4 | 2.85 | 7 |
| 32.4 | 2.76 | 2 |
| 33.0 | 2.71 | 1 |
| 34.0 | 2.63 | 3 |
| 34.6 | 2.59 | 1 |
| 37.9 | 2.37 | 2 |
| 40.5 | 2.23 | 1 |
| 41.2 | 2.19 | 1 |
| 43.1 | 2.10 | 1 |
| 44.0 | 2.06 | 1 |

(c) Adsorption capacities were measured on this calcined product using a standard McBain-Bakr gravimetric adsorption apparatus. The following data were obtained on a sample activated at 350° C. in vacuum.

| | Kinetic Diameter, A | Pressure, Torr | Temp., °C. | Wt. % Adsorbed |
|---|---|---|---|---|
| $O_2$ | 3.46 | 100 | −183 | 35.0 |
| $O_2$ | 3.46 | 750 | −183 | 42.9 |
| Cyclohexane | 6.0 | 60 | 24 | 23.2 |
| Neopentane | 6.2 | 743 | 24 | 14.8 |
| $H_2O$ | 2.65 | 4.6 | 24 | 35.3 |

The pore size of the calcined product is greater than 6.2 A, as shown by adsorption of neopentane, kinetic diameter of 6.2 A.

(d) EDAX (energy dispersive analysis by X-ray) microprobe analysis, performed in conjunction with SEM (scanning electron microscope) study, on clean crystals having a crystal morphology characteristic of SAPO-37 gives the following analysis based on relative peak heights:

Si: 1
Al: 3
P: 2

(e) Mixtures of tetramethylammonium hydroxide with tri-n-propylamine and with tetra-n-butylammonium hydroxide were also found to facilitate the formation of SAPO-37.

EXAMPLE 44

(Preparation of SAPO-37)

Using the same general procedure and reagents as in Example 42, supra, but using a mixture of tetramethylammonium hydroxide and tetrapropylammonium hydroxide as the templating agent, a reaction mixture was prepared having the following composition in terms of molar oxide ratios:

0.025(TMA)₂O:1.0(TPA)₂O:Al₂O₃:P₂O₅:2.0SiO₂:50H₂O

Upon crystallization at 200° C. in a sealed reactor for 72 hours, the product was found to contain principally SAPO-37 in combination with about 20 wt.-% of the crystalline solids being identified as SAPO-5 and about 10 wt.-% SAPO-40.

The species SAPO-37 as referred to herein is a silicoaluminophosphate having a microporous crystalline framework structure and whose essential empirical chemical composition in the as-synthesized form and on anhydrous basis is:

wherein R represents at least one organic templating agent present in the intracrystalline pore system, "m" has a value of from 0.02 to 0.3, "x", "y" and "z" represent, respectively, the mole fraction of silicon, aluminum and phosphorus present in the oxide moiety, the value of x, y and z being within the compositional area bounded by points A, B, C, D and E on the ternary diagram which is FIG. 1, or preferably within the area bounded by points a, b, c, d and e on the ternary diagram which is FIG. 2, said silicoaluminophosphate having a characteristic X-ray powder diffraction pattern which contains at least the d-spacings set forth below in Table XV:

TABLE XV

| 2θ | d | Relative Intensity |
|---|---|---|
| 6.1–6.3 | 14.49–14.03 | vs |
| 15.5–15.7 | 5.72–5.64 | w–m |
| 18.5–18.8 | 4.80–4.72 | w–m |
| 23.5–23.7 | 3.79–3.75 | w–m |
| 26.9–27.1 | 3.31–3.29 | w–m |

All of the as-synthesized SAPO-37 compositions for which X-ray powder diffraction data have presently been obtained have patterns which are within the generalized pattern of Table XVI, below.

TABLE XVI

| 2θ | d | 100 × I/I₀ |
|---|---|---|
| 6.1–6.3 | 14.49–14.03 | 100 |
| 10.1–10.3 | 8.76–8.59 | 22–30 |
| 11.8–12.0 | 7.50–7.37 | 4–10 |
| 15.5–15.7 | 5.72–5.64 | 30–60 |
| 18.5–18.8 | 4.80–4.72 | 20–50 |
| 20.2–20.4 | 4.40–4.35 | 12–26 |
| 21.0–21.2 | 4.23–4.19 | 4–10 |
| 22.7–22.9 | 3.92–3.88 | 8–21 |
| 23.5–23.7 | 3.79–3.75 | 24–59 |
| 24.6–24.9 | 3.62–3.58 | 1–3 |
| 25.6–25.8 | 3.48–3.45 | 5–11 |
| 26.9–27.1 | 3.31–3.29 | 14–42 |
| 27.6–27.9 | 3.232–3.198 | 2–4 |
| 29.4–29.7 | 3.038–3.008 | 2–11 |
| 30.6–30.8 | 2.921–2.903 | 5–18 |
| 31.2–31.5 | 2.867–2.840 | 12–32 |
| 32.2–32.5 | 2.780–2.755 | 3–11 |
| 33.0–33.2 | 2.714–2.698 | 1–3 |
| 33.9–34.2 | 2.644–2.622 | 4–14 |
| 34.3–34.5 | 2.614–2.600 | 2–6 |
| 37.7–38.0 | 2.386–2.368 | 3–9 |
| 40.4–40.7 | 2.232–2.217 | 1–5 |
| 41.2–41.5 | 2.191–2.176 | 1–7 |
| 43.1–43.3 | 2.099–2.089 | 1–7 |
| 43.9–44.1 | 2.062–2.053 | 2–8 |

EXAMPLE 45

(Preparation of SAPO-40)

(a) A reaction mixture was prepared by combining 9.22 grams of 85 wt.% orthophosphoric acid ($H_3PO_4$) and 5.78 grams of water, to which was added 5.52 grams of a hydrated aluminum oxide, (a pseudo-boehmite phase, 74.2 wt.% Al$_2$O$_3$, 25.8 wt.% H$_2$O), and stirred until homogeneous. To this mixture was added a dispersion of 1.04 grams of a fumed silica (92.8 wt.% SiO$_2$, 7.2 wt.% H$_2$O) in 40.82 grams of an aqueous solution of 40 wt.% tetra-n-propylammonium hydroxide (TPAOH), and the mixture stirred until homogeneous. The composition of the final reaction mixture in molar oxide ratios was:

Al$_2$O$_3$:P$_2$O$_5$:0.4SiO$_2$:(TPA)$_2$O:50H$_2$O

The gel was crystallized at 200° C. for 24 hours under autogenous pressure to yield a crystalline product containing SAPO-40 which was recovered by centrifuging, washing with water, and drying in air at room temperature. The solids were subjected to X-ray analysis. The results indicate the presence of a minor proportion of SAPO-40 in admixture with other known SAPO phases. After removing peaks corresponding to other phases from the X-ray powder diffraction pattern, a pattern remained representing a minor component and characterized by the following data:

TABLE Z

| 2θ | d | 100 × I/I$_o$ |
|---|---|---|
| 8.061 | 10.97 | 85 |
| 12.46 | 7.10 | 100 |
| 13.711 | 6.46 | 42 |
| 14.044 | 6.31 | 30 |
| 17.632 | 5.03 | 17 |
| 21.899 | 4.06 | 22 |
| 24.020 | 3.70 | 15 |

(b) EDAX (energy dispersive analysis by X-ray) microprobe analysis, performed in conjunction with SEM (scanning electron microscope) study, on clean crystals of SAPO-40 gives the following analysis based on relative peak heights:
Si: 0.08
Al: 1.0
P: 0.87

EXAMPLE 46

(Preparation of SAPO-40)

(a) SAPO-40 was also produced by crystallizing at 200° C. for 96 hours under autogenous pressure a reaction mixture containing both sodium hydroxide and TPAOH in addition to phosphoric acid, a hydrated aluminum oxide, water and a fumed silica in proportions such that the reaction mixture had the composition:

Al$_2$O$_3$:P$_2$O$_5$:0.4SiO$_2$:(TPA)$_2$O:0.01Na$_2$O:50H$_2$O

A portion of the recovered solids was analyzed with X-radiation to produce a powder diffraction pattern characterized by the following data (peaks resulting solely from a minor SAPO-5 impurity have been omitted):

TABLE AA

| 2θ | d | 100 × I/I$_o$ |
|---|---|---|
| 7.60 | 11.63 | 18* |
| 8.03 | 11.01 | 100 |
| 12.43 | 7.12 | 18 |
| 13.68 | 6.47 | 43 |
| 14.02 | 6.32 | 12 |
| 16.12 | 5.50 | 1 |
| 17.36 | 5.11 | 7 |
| 18.50 | 4.80 | 14 |
| 19.72 | 4.50 | 6 |
| 20.39 | 4.36 | 13 |
| 21.40 | 4.15 | 10 |
| 21.68 | 4.10 | 6 |
| 22.93 | 3.88 | 4 |
| 23.74 | 3.75 | 19 |
| 24.21 | 3.68 | 5 |
| 24.62 | 3.61 | 1 |
| 27.32 | 3.264 | 22 |
| 27.84 | 3.204 | 15 |
| 28.10 | 3.176 | 4 |
| 28.59 | 3.123 | 1 |
| 30.34 | 2.946 | 3 |
| 30.61 | 2.920 | 2 |
| 31.07 | 2.878 | 3 |
| 31.76 | 2.817 | 4 |
| 32.33 | 2.769 | 3 |
| 33.28 | 2.692 | 2 |
| 33.77 | 2.654 | 2 |
| 35.07 | 2.559 | 2 |
| 35.82 | 2.507 | 3 |

*Contains peak from impurity

Chemical analysis indicated the product contained 8.9 wt.% C, 1.0 wt.% N, 34.4 wt.% Al$_2$O$_3$, 40.4 wt.% P$_2$O$_5$, 6.9 wt.% SiO$_2$, 0.7 wt.% Na$_2$O, 17.5 wt.% LOI, giving a product composition in molar oxide ratios of:

0.092(TPA)$_2$O:0.034Na$_2$O:1.00Al$_2$O$_3$:0.85P$_2$O$_5$:0.34SiO$_2$:0.81H$_2$O, and a formula (anhydrous basis)

[0.045(TPA),0.017Na]:(Si$_{0.085}$Al$_{0.495}$P$_{0.42}$)O$_2$ (b) A portion of the product of part (a) supra was calcined in air at 700° C. for 1 hour. The X-ray pattern of the calcined material was characterized by the following data after subtraction of peaks contributed by identified impurities:

TABLE BB

| 2θ | d | 100 × I/I$_o$ |
|---|---|---|
| 7.60 | 11.63 | 78 |
| 7.95 | 11.19 | 100 |
| 12.55 | 7.08 | 14 |
| 13.60 | 6.51 | 13 |
| 14.20 | 6.24 | 13 |
| 16.00 | 5.54 | 3 |
| 17.40 | 5.10 | 9 |
| 18.60 | 4.77 | 15 |
| 20.40 | 4.35 | 7 |
| 21.65 | 4.11 | 4 |
| 22.75 | 3.92 | 3 |
| 23.70 | 3.75 | 3 |
| 27.15 | 3.290 | 15 |
| 28.00 | 3.186 | 12 |
| 30.65 | 2.921 | 3 |
| 31.70 | 2.822 | 3 |
| 32.40 | 2.763 | 2 |

(c) Adsorption capacities were measured on this calcined product using a standard McBain-Bakr gravimetric adsorption apparatus. The following data were obtained on a sample activated at 350° C. in vacuum.

| | Kinetic Diameter, A | Pressure, Torr | Temp., °C. | Wt % Adsorbed |
|---|---|---|---|---|
| O$_2$ | 3.46 | 100 | −183 | 21.8 |
| O$_2$ | 3.46 | 750 | −183 | 24.4 |
| Cyclohexane | 6.0 | 60 | 24 | 8.0 |
| Neopentane | 6.2 | 743 | 24 | 5.1 |

| | Kinetic Diameter, A | Pressure, Torr | Temp., °C. | Wt % Adsorbed |
|---|---|---|---|---|
| H₂O | 2.65 | 4.6 | 24 | 22.7 |
| H₂O | 2.65 | 20 | 24 | 31.5 |
| Isobutane | 5.0 | 697 | 24 | 7.0 |
| SF₆ | 5.5 | 400 | 24 | 11.6 |

The pore size of the calcined product appears to be greater than 6.2 A, as shown by adsorption of neopentane, kinetic diameter 6.2 A. It should be noted, however, that the sample contained substantial amounts of SAPO-5, which adsorbs molecules as large as neopentane.

(d) EDAX (energy dispersive analysis by X-ray) microprobe analysis, performed in conjunction with SEM (scanning electron microscope) study, on clean crystals having a crystal morphology characteristic of SAPO-40 gives the following analysis based on relative peak heights:

| Laths | |
|---|---|
| Si | 0.14 |
| Al | 1.0 |
| P | 0.95 |

EXAMPLE 47

(Preparation of SAPO-40)

A reaction mixture was prepared by combining, in a manner to obtain a homogeneous composition, 6.90 grams of a hydrated aluminum oxide (74.2 wt.-% Al₂O₃, 25.8 wt.-% H₂O) with 11.53 grams of 85% orthophosphoric acid, and a solution of 0.38 gram ammonium acetate (NH₄Ac) in 11.16 grams H₂O, and finally with a mixture of 1.30 grams of a fumed silica (92.8 wt.-% SiO₂) in 50.9 grams of 40% aqueous tetra-n-propylammonium hydroxide solution (TPAOH). The composition of the reaction mixture was:

0.1NH₄Ac:(TPA)₂O:Al₂O₃:0.4SiO₂:P₂O₅:50H₂O

After digestion and crystallization in a sealed reactor at 200° C. for 24 hours, a SAPO-40-containing product was recovered. The SAPO-40 component exhibited an X-ray powder diffraction pattern essentially identical to that of Example 46.

The species SAPO-40 as referred to herein is a silicoaluminophosphate material having a three-dimensional microporous crystal framework structure of PO₂⁺, AlO₂⁻ and SiO₂ tetrahedral units, and whose essential empirical chemical composition on an anhydrous basis is:

mR:(Si$_x$Al$_y$P$_x$)O₂ wherein "R" represents at least one organic templating agent present in the intracrystalline pore system; "m" represents the moles of "R" present per mole of (Si$_x$Al$_y$P$_z$)O₂ and has a value of from zero to 0.3, "x", "y" and "z" represent respectively, the mole fractions of silicon, aluminum and phosphorus present in the oxide moiety, said mole fractions being within the compositional area bounded by points A, B, C, D and E on the ternary diagram which is FIG. 1, or preferably within the area bounded by points a, b, c, d and e on the ternary diagram which is FIG. 2, said silicoaluminophosphate having a characteristic X-ray powder diffraction pattern which contains at least the d-spacings set forth below in Table XVII. In the form as synthesized in accordance with the process of this invention, "m" has a value of from 0.02 to 0.3.

TABLE XVII

| | SAPO-40 | |
|---|---|---|
| 2θ | d | Relative Intensity |
| 7.5–7.7 | 11.79–11.48 | VW–M |
| 8.0–8.1 | 11.05–10.94 | S–VS |
| 12.4–12.5 | 7.14–7.08 | W–VS |
| 13.6–13.8 | 6.51–6.42 | M–S |
| 14.0–14.1 | 6.33–6.28 | W–M |
| 27.8–28.0 | 3.209–3.18 | W–M |

All of the as-synthesized SAPO-40 compositions for which X-ray powder diffraction data have presently been obtained have patterns which are within the generalized pattern of Table XVIII, below.

TABLE XVIII

| 2θ | d | 100 × I/I$_o$ |
|---|---|---|
| 7.5–7.71 | 11.79–11.48 | 6–51 |
| 8.0–8.11 | 11.05–10.94 | 85–100 |
| 12.4–12.5 | 7.14–7.08 | 15–100 |
| 13.6–13.8 | 6.51–6.42 | 43–62 |
| 14.0–14.1 | 6.33–6.28 | 12–36 |
| 16.1–16.3 | 5.50–5.44 | 1–2 |
| 17.3–17.7 | 5.13–5.01 | 6–17 |
| 18.5–18.6 | 4.80–4.77 | 14–30 |
| 19.7–20.0 | 4.51–4.44 | 6–22 |
| 20.3–20.5 | 4.37–4.33 | 12–19 |
| 21.3–21.5 | 4.17–4.13 | 10–19 |
| 21.6–21.9 | 4.11–4.06 | 6–22 |
| 22.9–23.2 | 3.88–3.83 | 4–9 |
| 23.7–23.8 | 3.75–3.74 | 19–30 |
| 24.0–24.3 | 3.71–3.66 | 0–5 |
| 24.6–24.7 | 3.62–3.60 | 1–17 |
| 27.3–27.5 | 3.267–3.24 | 22–29 |
| 27.8–28.0 | 3.209–3.18 | 15–33 |
| 28.0–28.2 | 3.187–3.164 | 0–4 |
| 28.5–28.7 | 3.132–3.110 | 0–2 |
| 29.2–29.3 | 3.058–3.048 | 0–9 |
| 30.3–30.4 | 2.950–2.940 | 0–3 |
| 30.6–30.7 | 2.921–2.912 | 0–2 |
| 31.0–31.2 | 2.885–2.867 | 0–3 |
| 31.7–31.9 | 2.823–2.805 | 4–5 |
| 32.3–32.5 | 2.772–2.755 | 3–5 |
| 33.2–33.4 | 2.698–2.683 | 1–2 |
| 33.7–33.8 | 2.660–2.652 | 2–3 |
| 35.0–35.2 | 2.564–2.550 | 2–3 |
| 35.8–35.9 | 2.508–2.501 | 2–3 |

EXAMPLE 48

(Preparation of SAPO-42)

(a) SAPO-42, which appears to be structurally similar to the aluminosilicate zeolite A, is found to be produced by the extended aging at lower temperatures of a gel composition which otherwise yields SAPO-20, a silicoaluminophosphate which has structural similarity to the aluminosilicate sodalite. The gel involved was prepared as in Example 28 supra and had a composition in molar oxide ratios of:

1.2Na₂O:1.1(TMA)₂O:4.0SiO₂:1.66Al₂O₃:0.66-P₂O₅:95H₂O

Part of the reaction mixture was placed in a sealed inert plastic container and heated in an oven at 100° C. at autogenous pressure for 480 hours. The solid reaction product was recovered by centrifugation, washed with water, and dried in air at 100° C. The above product had an X-ray powder diffraction pattern characterized by the following data:

TABLE CC

| 2θ | d | 100 × I/I₀ |
|---|---|---|
| 7.4 | 11.9 | 71 |
| 10.4 | 8.51 | 55 |
| 12.7 | 6.97 | 61 |
| 13.9 | 6.37 | 7 |
| 16.35 | 5.42 | 31 |
| 17.9 | 4.96 | 13 |
| 21.6 (sh) | 4.13 | 68 |
| 21.9 | 4.06 | |
| 23.1 | 3.85 | 17 |
| 24.25 | 3.67 | 100 |
| 26.4 | 3.376 | 29 |
| 27.4 | 3.255 | 83 |
| 30.25 | 2.955 | 75 |
| 31.1 | 2.876 | 15 |
| 32.9 | 2.722 | 19 |
| 33.7 | 2.660 | 9 |
| 34.45 | 2.603 | 37 |
| 36.05 | 2.491 | 19 |
| 36.9 | 2.436 | 5 |
| 38.35 | 2.347 | 5 |
| 40.5 | 2.227 | 7 |
| 41.85 | 2.158 | 11 |
| 42.55 | 2.125 | 6 |
| 43.15 | 2.096 | 3 |
| 43.85 | 2.065 | 1 |
| 44.5 | 2.036 | 9 |
| 47.7 | 1.907 | 8 |
| 48.3 | 1.884 | 4 |
| 49.0 | 1.859 | 1 |
| 49.5 | 1.841 | 6 |
| 50.05 | 1.822 | 4 |
| 52.4 | 2.746 | 3 |
| 53.0 | 1.728 | 16 |
| 53.6 | 1.710 | 2 |
| 54.65 | 1.679 | 16 |
| 55.2 | 1.664 | 2 |

By chemical analysis, the composition of the crystalline product was found to be 11.3 wt.% Na₂O, 38.3 wt.% SiO₂, 25.6 wt.% Al₂O₃, 1.6 wt.-% C, 0.43 wt.% N, 4.4 wt.% P₂O₅, 19.9 wt.% LOI, giving a product composition in molar oxide ratios of:

0.07(TMA)₂O:2.5SiO₂:0.7Na₂O:Al₂O₃:0.1P₂O₅:3.7-H₂O which corresponds in turn to the essential formula (anhydrous basis):

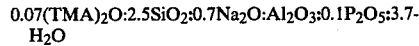

0.03(TMA):(Si$_{0.53}$Al$_{0.42}$P$_{0.04}$)O₂

(b) A portion of the SAPO-42 part (a) supra was calcined in air at 550° C. for 2 hours. Adsorption capacities were measured on this calcined sample using a standard McBain-Bakr gravimetric adsorption apparatus. The following data were obtained on a sample activated at 350° C.

| | Kinetic Diameter, A | Pressure, Torr | Temp., °C. | Wt.% Adsorbed |
|---|---|---|---|---|
| O₂ | 3.46 | 98.5 | −183 | 12.6 |
| O₂ | 3.46 | 740. | −183 | 17.0 |
| n-Hexane | 4.3 | 53.5 | 24 | 7.4 |
| Isobutane | 5.0 | 751. | 24 | 1.0 |
| H₂O | 2.65 | 4.6 | 23 | 15.5 |
| H₂O | 2.65 | 19.4 | 24 | 21.0 |

The pore size of the calcined product is >4.3 A, as shown by the adsorption of n-hexane.

EXAMPLE 49

(Preparation of SAPO-42)

A reaction mixture having the composition, in terms of molar oxide ratios of:

4.2(TEA)₂O:SiO₂:2.0Al₂O₃:P₂O₅:129H₂O was prepared, using as the reagents, water, a hydrated alumina, orthophosphoric acid, tetraethylammonium hydroxide (TEAOH) and a silica sol. In the preparation, an aluminophosphate gel was first prepared by combining 17.2 grams of the hydrated alumina (74.2 wt.-% Al₂O₃) with 18.4 grams H₂O, 28.8 grams of 85 wt.-% orthophosphoric acid and 151.7 grams of a 40.7 wt.-% aqueous solution of the TEAOH. A second mixture formed by combining the remaining alumina, TEAOH and the silica sol was then added to the initially prepared gel. The final reaction mixture was crystallized at 200° C. for 168 hours in a sealed reactor. X-ray analysis of the isolated product established that SAPO-42 had been produced.

The species SAPO-42 as referred to herein is a silicoaluminophosphate having a microporous crystalline framework structure and whose empirical chemical composition in the as-synthesized form and an anhydrous basis:

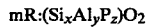

mR:(Si$_x$Al$_y$P$_z$)O₂ wherein R represents at least one organic templating agent present in the intracrystalline pore system, "m" has a value of from 0.02 to 0.3 "x", "y" and "z" represent, respectively, the mole fraction of silicon, aluminum and phosphorus present in the oxide moiety, the value of x, y and z being within the compositional area bounded by points A, B, C, D and E on the ternary diagram which is FIG. 1, or preferably within the area bounded by points a, b, c, d and e on the ternary diagram which is FIG. 2., said silicoaluminophosphate having a characteristic X-ray powder diffraction pattern which contains at least the d-spacings set forth below in Table XIX:

TABLE XIX

| 2θ | d | Relative Intensity |
|---|---|---|
| 7.15–7.4 | 12.36–11.95 | M-VS |
| 12.5–12.7 | 7.08–6.97 | M-S |
| 21.75–21.9 | 4.086–4.058 | M-S |
| 24.1–24.25 | 3.69–3.67 | VS |
| 27.25–27.4 | 3.273–3.255 | S |
| 30.05–30.25 | 2.974–2.955 | M-S |

All of the as-synthesized SAPO-42 compositions for which X-ray powder diffraction data have presently been obtained have patterns which are within the generalized pattern of Table XX, below:

TABLE XX

| 2θ | d | 100 × I/I₀ |
|---|---|---|
| 6.75–6.85 | 13.09–12.90 | sh-13 |
| 7.15–7.4 | 12.36–11.95 | 51–100 |
| 10.2–10.4 | 8.67–8.51 | 42–65 |
| 12.5–12.7 | 7.08–6.97 | 48–74 |
| 13.65–13.9 | 6.49–6.37 | 5–10 |
| 16.2–16.35 | 5.47–5.42 | 31–37 |
| 17.7–17.9 | 5.01–4.96 | 11–17 |

TABLE XX-continued

| 2θ | d | 100 × I/I₀ |
|---|---|---|
| 20.5 | 4.33 | 0-3 |
| 21.5-21.6 | 4.13-4.11 | sh-12 |
| 21.75-21.9 | 4.086-4.058 | 53-72 |
| 22.95-23.1 | 3.875-3.850 | 13-20 |
| 24.1-24.25 | 3.693-3.670 | 91-100 |
| 26.2-26.4 | 3.401-3.376 | 19-29 |
| 27.25-27.4 | 3.273-3.255 | 73-87 |
| 27.7 | 3.220 | 0-6 |
| 30.05-30.25 | 2.974-2.955 | 64-80 |
| 31.0-31.1 | 2.885-2.876 | 10-16 |
| 32.65-32.9 | 2.743-2.722 | 16-21 |
| 33.55-33.7 | 2.671-2.660 | 6-10 |
| 34.35-34.45 | 2.612-2.603 | 32-39 |
| 35.9-36.05 | 2.501-2.491 | 13-19 |
| 36.75-36.9 | 2.445-4.436 | 3-8 |
| 38.15-38.25 | 2.359-2.347 | 5-8 |
| 40.35-40.5 | 2.235-2.227 | 7-11 |
| 41.7-41.95 | 2.166-2.154 | 8-13 |
| 42.35-42.55 | 2.134-2.125 | 5-13 |
| 43.15-43.4 | 2.096-2.085 | 0-3 |
| 43.8-43.85 | 2.067-2.065 | 0-2 |
| 44.45-44.55 | 2.038-2.034 | 6-9 |
| 47.55-47.7 | 1.912-1.907 | 8-10 |
| 48.2-48.3 | 1.888-1.884 | 3-6 |
| 48.85-49.0 | 1.864-1.859 | 0-7 |
| 49.05-49.5 | 1.857-1.841 | 5-7 |
| 50.01-50.05 | 1.824-1.822 | 0-5 |
| 52.3-52.4 | 1.749-1.746 | 0-3 |
| 52.9-53.0 | 1.731-1.728 | 11-16 |
| 53.6 | 1.710 | 0-2 |
| 54.6-54.7 | 1.681-1.678 | 8-16 |
| 55.1-55.2 | 1.667-1.664 | 0-3 |

EXAMPLE 50

(Preparation of SAPO-44)

A SAPO species which has no known structural counterpart in the AlPO₄ or zeolite series, SAPO-44, is prepared by combining 23.1 grams of 85 wt.% orthophosphoric acid (H₃PO₄) and 57.8 grams of water with 40.9 grams of aluminum isopropoxide (Al(OC₃H₇)₃) and 5.0 grams of water and the mixture stirred until homogeneous. To this mixture were added 12.0 grams of an aqueous sol of 30 wt.% SiO₂ and 5.0 grams of water and the mixture stirred until homogenous. To this mixture were added 9.9 grams of cyclohexylamine (C₆H₁₁NH₂) and 5.0 grams of water, and the mixture stirred until homogenous. The composition of the final reaction mixture in molar oxide ratios was:

C₆H₁₁NH₂:0.6SiO₂:Al₂O₃:P₂O₅:50H₂O

Part of the reaction mixture was placed in a stainless steel pressure vessel lined with an inert plastic material and heated in an oven at 200° C. at autogenous pressure for 52 hours. The solid reaction product was recovered by centrifugation, washed with water, and dried in air at 100° C. The above product was impure but the major phase (SAPO-44) had an X-ray powder diffraction pattern characterized by the following data:

TABLE DD

| 2θ | d | 100 × I/I₀ |
|---|---|---|
| 7.5* | 11.8 | 2 |
| 9.5 | 9.31 | 100 |
| 10.95 | 8.08 | 4 |
| 13.0 | 6.81 | 31 |
| 13.3 | 6.66 | 1 |
| 13.75 | 6.44 | 3 |
| 14.9* | 5.95 | 1 |
| 16.15 | 5.49 | 51 |
| 17.4 | 5.10 | 9 |
| 19.0 | 4.67 | 6 |
| 19.7* | 4.51 | 1 |
| 20.85 | 4.26 | |
| 21.1 (sh)* | 4.21 | 98 |
| 21.9 | 4.06 | 25 |
| 22.5 (sh)* | 3.95 | |
| 22.7 | 3.92 | 7 |
| 23.1 | 3.85 | 12 |
| 24.55 | 3.626 | 55 |
| 25.9 (sh)* | 3.440 | |
| 26.2 | 3.401 | 22 |
| 26.9 | 3.314 | 1 |
| 27.9 | 3.198 | 10 |
| 28.5 | 3.132 | 2 |
| 29.0* | 3.079 | 1 |
| 29.7 | 3.008 | 4 |
| 30.2* | 2.959 | 18 |
| 30.9 | 2.894 | 80 |
| 31.6 | 2.831 | 1 |
| 32.15 | 2.784 | 2 |
| 32.55 | 2.751 | 3 |
| 33.0 | 2.714 | 5 |
| 33.6* | 2.667 | 1 |
| 34.8* | 2.578 | 3 |
| 35.6 | 2.522 | 11 |
| 38.5 | 2.338 | 1 |
| 39.2 | 2.298 | 1 |
| 39.9 | 2.259 | 2 |
| 42.3 | 2.137 | |
| 42.6 (sh) | 2.122 | 4 |
| 43.7 | 2.071 | 3 |
| 44.4 | 2.040 | 1 |
| 45.2 | 2.006 | 1 |
| 46.2 | 1.965 | 1 |
| 47.3 | 1.922 | 2 |
| 48.2* | 1.888 | 6 |
| 48.8 | 1.866 | 5 |
| 50.5 | 1.807 | 9 |
| 51.2 | 1.784 | 1 |
| 52.2 | 1.752 | 2 |
| 54.0 | 1.698 | 8 |

*Possibly contains peak of another phase

Chemical analysis indicated the composition of the product SAPO-44 to be 0.59(C₆H₁₁NH₂):0.47SiO₂:Al₂O₃:0.85P₂O₅:0.64H₂O This corresponds to an essential empirical formula (anhydrous basis) of 0.14(C₆H₁₁NH₂):(Si₀.₁₁Al₀.₄₈P₀.₄₁)O₂

(b) A portion of the solid crystalline product obtained by heating a portion of the above reaction mixture at 200° C. for 168 hours and exhibiting an X-ray powder diffraction pattern essentially identical to that above was calcined in air at about 550° C. for 2 hours. The calcined product had an X-ray powder diffraction pattern characterized by the following data:

TABLE EE

| 2θ | d | 100 × I/I₀ |
|---|---|---|
| 7.4* | 11.9 | 1 |
| 9.5 | 9.3 | 100 |
| 10.9 | 8.12 | 3 |
| 12.95 | 6.84 | 46 |
| 13.4 | 6.61 | 3 |
| 13.9 | 6.37 | 3 |
| 16.1 | 5.50 | 22 |
| 17.8 | 4.98 | 22 |

TABLE EE-continued

| 2θ | d | 100 × I/I₀ |
|---|---|---|
| 19.1 | 4.65 | 3 |
| 20.75 | 4.28 | 54 |
| 22.1 | 4.02 | 5 |
| 22.65 | 3.925 | 1 |
| 23.2 | 3.834 | 11 |
| 24.9 | 3.576 | 23 |
| 26.1 | 3.414 | 18 |
| 27.2 | 3.278 | 1 |
| 27.8 | 3.209 | 3 |
| 28.2 | 3.164 | 7 |
| 29.2 | 3.058 | 1 |
| 29.75 | 3.003 | 3 |
| 30.8 | 2.903 | 40 |
| 31.2 | 2.867 | 16 |
| 31.8 | 2.814 | 1 |
| 32.5 | 2.755 | 2 |
| 33.6* | 2.667 | 3 |
| 34.8* | 2.578 | 5 |
| 35.2 | 2.550 | 1 |
| 36.2 | 2.481 | 3 |
| 43.0 | 2.103 | 1 |
| 48.2* | 1.888 | 1 |
| 49.2 | 1.852 | 2 |
| 51.1 | 1.787 | 2 |
| 53.8 | 1.704 | 1 |
| 54.6 | 1.681 | 1 |

*possibly contains peak from another phase (c) Adsorption capacities were measured on this calcined product using a standard McBain-Bakr gravimetric adsorption apparatus. The following data were obtained on a sample activated at 350° C.:

| | Kinetic Diameter, Å | Pressure, Torr | Temp., °C. | Wt % Adsorbed |
|---|---|---|---|---|
| O₂ | 3.46 | 98 | −183 | 25.5 |
| O₂ | 3.46 | 746 | −183 | 32.3 |
| n-hexane | 4.3 | 48 | 23.9 | 3.6 |
| isobutane | 5.0 | 101 | 25.4 | 0 |

The pore size of the calcined product is >4.3 Å and <5.0 Å, as shown by adsorption of n-hexane, kinetic diameter of 4.3 Å and nil adsorption of isobutane, kinetic diameter of 5.0 Å.

The species SAPO-44 as referred to herein is a silicoaluminophosphate material having a three-dimensional microporous crystal framework structure of $PO_2^+$, $AlO_2^-$ and $SiO_2$ tetrahedral units, and whose essential empirical chemical composition on an anhydrous basis is:

$$mR:(Si_xAl_yP_x)O_2$$

wherein "R" represents at least one organic templating agent present in the intracrystalline pore system; "m" represents the moles of "R" present per mole of $(Si_x\text{-}Al_yP_z)O_2$ and has a value of from zero to 0.3, "x", "y" and "z" represent respectively, the mole fractions of silicon, aluminum and phosphorous present in the oxide moiety, said mole fractions being within the compositional area bounded by points A, B, C, D and E on the ternary diagram which is FIG. 1, or preferably within the area bounded by points a, b, c, d and e on the ternary diagram which is FIG. 2, said silicoaluminophosphate having a characteristic X-ray powder diffraction pattern which contains at least the d-spacings set forth below in Table XXI. In the form as synthesized in accordance with the process of this invention, "m" has a value of from 0.03 to 0.3.

TABLE XXI

| 2θ | d | Relative Intensity |
|---|---|---|
| 9.4–9.55 | 9.41–9.26 | VS |
| 13.0–13.1 | 6.81–6.76 | W–M |
| 16.1–16.2 | 5.50–5.47 | W–M |
| 20.75–20.85 | 4.28–4.26 | S–VS |
| 30.85–30.95 | 2.898–2.889 | M–S |

All of the as-synthesized SAPO-44 compositions for which X-ray powder diffraction data have presently been obtained have patterns which are within the generalized pattern of Table XXII, below:

TABLE XXII

| 2θ | d | 100 × I/I₀ |
|---|---|---|
| 9.4–9.5 | 9.41–9.26 | 97–100 |
| 10.95 | 8.08 | 4–12 |
| 13.0–13.1 | 6.81–6.76 | 15–31 |
| 13.3–13.4 | 6.66–6.61 | 1–6 |
| 13.75–13.8 | 6.44–6.42 | 3 |
| 16.1–16.2 | 5.50–5.47 | 31–55 |
| 17.35–17.4 | 5.11–5.10 | 9–16 |
| 19.0 | 4.67 | 6 |
| 20.75–20.85 | 4.28–4.26 | } 68–100 |
| 21.0–21.1 (sh) | 4.23–4.21 | |
| 21.8–21.9 | 4.08–4.06 | 25 |
| 22.6–22.7 | 3.93–3.92 | 3–7 |
| 23.1 | 3.85 | 7–12 |
| 24.45–24.55 | 3.641–3.626 | 55–74 |
| 26.15–26.2 | 3.408–3.401 | 16–22 |
| 26.9 | 3.314 | 1–2 |
| 27.8–27.9 | 3.209–3.198 | 7–10 |
| 28.5 | 3.132 | 2–7 |
| 29.7 | 3.008 | 3–4 |
| 30.2 | 2.959 | 18–20 |
| 30.85–30.95 | 2.898–2.889 | 45–50 |
| 31.6–31.65 | 2.831–2.827 | 1 |
| 32.15–32.2 | 2.784–2.780 | 2–7 |
| 32.55–32.6 | 2.751–2.747 | 1–3 |
| 33.0 | 2.714 | 5 |
| 34.8 | 2.578 | 1–3 |
| 35.6 | 2.522 | 8–11 |
| 38.5–38.6 | 2.338–2.332 | 1 |
| 39.2 | 2.298 | 1 |
| 39.9–40.0 | 2.259–2.254 | 1–2 |
| 42.2–42.3 | 2.141–2.137 | } 4 |
| 42.6 (sh) | 2.122 | |
| 42.9 (sh) | 2.108 | 4 |
| 43.6–43.7 | 2.076–2.071 | 2–3 |
| 44.3–44.4 | 2.045–2.040 | 1 |
| 45.1–45.2 | 2.010–2.006 | 1 |
| 46.1–46.2 | 1.969–1.965 | 1 |
| 47.2–47.3 | 1.926–1.922 | 2 |
| 48.15–48.2 | 1.890–1.888 | 6–7 |
| 48.7–48.8 | 1.870–1.866 | 5 |
| 50.4–50.5 | 1.811–1.807 | 7–9 |
| 51.2–51.3 | 1.784–1.781 | 1 |
| 52.1–52.2 | 1.755–1.752 | 2 |
| 53.9–54.0 | 1.701–1.698 | 6–8 |

EXAMPLE 51

(Preparation of SAPO-31)

SAPO-31 was crystallized from a reaction mixture prepared by combining 81.7 grams of aluminum isopropoxide (Al(OC₃H₇)₃) with 46.1 grams of 85 wt.% orthophosphoric acid (H₃PO₄) and 85.0 grams of water and stirring until homogeneous. To this mixture were added 24.0 grams of an aqueous sol of 30 wt.% SiO₂ and 42.8 grams of water, and the mixture stirred until homogeneous. To this mixture were added 20.2 grams of di-n-propylamine (Pr₂NH) and 34.0 grams of water, and the mixture stirred until homogeneous. To this mixture was added 5.8 grams of AlPO$_4$-31 seed crystals and the mixture stirred until homogeneous. The composition of the final reaction mixture in molar oxide ratios was: Pr$_2$NH:0.6SiO$_2$:Al$_2$O$_3$:P$_2$O$_5$:50H$_2$O and contained 10 wt. % AlPO$_4$-31 seed crystals based on the solids content. A portion of this reaction mixture was placed in a stainless steel pressure vessel lined with an inert plastic material and heated in an oven at 200° C. at autogenous pressure for 24 hours. The solid reaction product was recovered by filtration, washed with water, and dried in air at 100° C. The chemical composition of the SAPO-31 product in terms of molar oxide ratios (anhydrous basis) was:

0.16(Pr$_2$NH):Al$_2$O$_3$:0.15SiO$_2$:0.83P$_2$O$_5$ which corresponds to the formula:

0.04Pr$_2$NH:(Si$_{0.04}$Al$_{0.53}$P$_{0.43}$)O$_2$

The x-ray powder diffraction pattern of the SAPO-31-containing product was characterized by the following data:

TABLE EF

| 2θ | d | 100 × I/I$_o$ |
|---|---|---|
| 7.25* | 12.193 | (sh) |
| 8.539 | 10.355 | 72 |
| 9.530* | 9.280 | 14 |
| 13.279* | 6.668 | 4 |
| 15.774* | 5.618 | 8 |
| 17.104 | 5.184 | 6 |
| 18.380 | 4.827 | 3 |
| 20.280 | 4.379 | 43 |
| 20.5* | 4.332 | (sh) |
| 21.153* | 4.200 | 22 |
| 22.033 | 4.034 | 28 |
| 22.662* | 3.924 | 100 |
| 23.316 | 3.815 | 14 |
| 25.145 | 3.542 | 3 |
| 25.718 | 3.464 | 3 |
| 26.566* | 3.355 | 3 |
| 26.701 | 3.339 | 4 |
| 27.976 | 3.189 | 9 |
| 28.810* | 3.099 | 4 |
| 29.797 | 2.998 | 6 |
| 31.760 | 2.817 | 16 |
| 33.016 | 2.713 | 3 |
| 34.367* | 2.609 | 2 |
| 35.215 | 2.549 | 8 |
| 36.090 | 2.489 | 2 |
| 37.777* | 2.381 | 3 |
| 37.938* | 2.372 | 3 |
| 38.113 | 2.361 | 3 |
| 39.402 | 2.287 | 3 |
| 39.641 | 2.274 | 2 |
| 40.195 | 2.244 | 2 |
| 44.891* | 2.019 | 2 |
| 45.345 | 2.000 | 2 |
| 46.708 | 1.945 | 2 |
| 51.670 | 1.769 | 3 |

*contains impurity peak

The X-ray powder diffraction pattern of the SAPO-31-containing product after calcination in air for 7 hours at 550° C. was characterized by the following data:

TABLE FF

| 2θ | d | 100 × I/I$_o$ |
|---|---|---|
| 7.7 | 11.5 | (sh) |
| 8.5 | 10.4 | 100 |
| 8.9 | 9.94 | (sh) |
| 9.6 | 9.21 | (sh) |
| 9.8 | 9.03 | 3 |
| 12.85 | 6.89 | 1 |
| 14.7 | 6.03 | 7 |
| 16.1 | 5.50 | 3 |
| 17.05 | 5.20 | 10 |
| 18.45 | 4.81 | 2 |
| 20.3 | 4.37 | 34 |
| 21.4 | 4.15 | (sh) |
| 22.05 | 4.03 | 37 |
| 22.6 | 3.93 | 81 |
| 23.35 | 3.81 | 3 |
| 25.1 | 3.548 | 3 |
| 25.7 | 3.466 | 4 |
| 27.9 | 3.198 | 11 |
| 29.7 | 3.008 | 8 |
| 31.0 | 2.885 | 1 |
| 31.7 | 2.823 | 18 |
| 32.4 | 2.763 | 1 |
| 35.1 | 2.557 | 7 |
| 36.2 | 2.481 | 2 |
| 37.2 | 2.417 | 2 |
| 37.6 | 2.392 | 2 |
| 38.3 | 2.350 | 2 |
| 39.3 | 2.292 | 3 |
| 39.6 | 2.276 | 1 |
| 40.3 | 2.238 | 3 |
| 43.2 | 2.094 | 1 |
| 44.0 | 2.058 | 1 |
| 45.0 | 2.014 | 2 |
| 47.1 | 1.929 | 3 |
| 47.6 | 1.910 | 2 |
| 48.6 | 1.873 | 2 |
| 49.2 | 1.852 | 1 |
| 50.8 | 1.797 | 1 |
| 51.6 | 1.771 | 4 |
| 55.6 | 1.653 | 1 |

(b) Adsorption capacities were measured on the product of part(a). The following data were obtained on a sample activated at 350° C. in vacuum.

| | Kinetic Diameter, Å | Pressure Torr | Temp., °C. | Wt. % Adsorbed |
|---|---|---|---|---|
| O$_2$ | 3.46 | 99 | −183 | 8.8 |
| O$_2$ | 3.46 | 740 | −183 | 15.4 |
| H$_2$O | 2.65 | 4.6 | 23 | 6.9 |
| H$_2$O | 2.65 | 19.4 | 24 | 21.1 |
| Cyclohexane | 6.0 | 49 | 25 | 7.2 |
| Neopentane | 6.2 | 400 | 24 | 5.9 |

It is apparent from these data that the pore size of SAPO-31 is greater than 6.2 Å.

EXAMPLE 52

(Preparation of SAPO-31)

SAPO-31 was produced using a different source of silica from a reaction mixture prepared by combining 81.6 grams of aluminum isopropoxide (Al(OC$_3$H$_7$)$_3$) and 100 grams of water with 51.3 grams of 85 wt. % orthophosphoric acid (H$_3$PO$_4$). To this mixture was added 1.33 grams of fume silica (95 wt. % SiO$_2$, 5 wt. % H$_2$O) and the mixture stirred until homogeneous. To one third by weight of this mixture were added 16.3 grams of water and 7.4 grams of di-n-propylamine (Pr$_2$NH), and the mixture stirred until homogeneous. The composition of the final reaction mixture in molar oxide ratios was:

Pr$_2$NH:0.1SiO$_2$:0.9Al$_2$O$_3$:P$_2$O$_5$:49H$_2$O

The reaction mixture was placed in a stainless steel pressure vessel lined with polytetrafluoroethylene and heated in an oven at 150° C. at autogenous pressure for 133 hours. The solid reaction product was recovered by centrifugation, washed with water, and dried in air at room temperature. The product was impure but the minor phase had an X-ray powder diffraction pattern characterized by the following data:

TABLE GG

| 2θ | d |
|---|---|
| 8.5 | 10.4 |
| 9.5* | 9.31 |
| 13.35* | 6.63 |
| 15.8* | 5.61 |
| 17.2 | 5.16 |
| 18.4 | 4.82 |
| 20.3 | 4.37 |
| 21.1* | 4.21 |
| 21.9 (sh) | 4.06 |
| 22.65* | 3.926 |
| 25.6 | 3.480 |
| 27.9 | 3.198 |
| 28.4 | 2.143 |
| 31.6* | 2.831 |
| 35.05 | 2.560 |

*contains peak from another phase

EXAMPLE 53

(Preparation of SAPO-31)

A homogeneous mixture was prepared by combining 306.4 grams of aluminum isopropoxide with a solution of 173.0 grams of 85 wt. % orthophosphoric acid in 545.3 grams of water. Thereafter were added in sequence, with intermittant stirring to achieve homogeneity after each addition, (a) 90.2 grams of an aqueous silica sol (30 wt. % SiO₂), (b) 75.9 grams of di-n-propylamine (n-C₃H₇)₂NH, and (c) 21.0 grams of AlPO₄-31 seed crystals. The composition of the final reaction mixture, in terms of molar oxide ratios, was (exclusive of the seed crystals).

$$(n\text{-}C_3H_7)_2NH{:}0.6SiO_2{:}Al_2O_3{:}P_2O_5{:}50H_2O$$

and contained 10 weight percent AlPO₄-31 seeds based on the overall solids content. The reaction mixture was placed in a stainless steel pressure reactor lined with an inert plastic material and heated under autogenous pressure for 96 hours at 200° C. The solid reaction product was recovered by centrifugation, washed with water, and dried in air at 110° C. The product was calcined in air using the following ramp schedule: (a) raised from room temperature to 230° C. over the period of 0.5 hour; (b) held at 230° C. for 2 hours; (c) increased from 230° C. to 500° C. over the period of 1 hour; (d) held at 500° C. for 2 hours; and (e) cooled from 500° C. to room temperature over the period of 4 hours. The calcined product had an X-ray powder diffraction pattern characterized by the following data:

TABLE GH

| 2θ | d | 100 × I/I₀ |
|---|---|---|
| 7.45* | 11.87 | <1 |
| 8.6 | 10.28 | 75 |
| 9.8* | 9.03 | <1 |
| 14.8 | 5.99 | 5 |
| 16.1 | 5.50 | <1 |
| 17.15 | 5.17 | 10 |
| 18.1* | 4.90 | <1 |
| 18.4 | 4.82 | 4 |
| 20.3 | 4.37 | 55 |
| 21.0* | 4.23 | <1 |
| 22.1 | 4.02 | 50 |
| 22.7 | 3.92 | 100 |
| 23.6* | 3.77 | <1 |
| 25.2 | 3.53 | 6 |
| 25.75 | 3.46 | 8 |
| 26.55* | 3.357 | <1 |
| 28.0 | 3.187 | 14 |
| 29.75 | 3.003 | 9 |
| 31.0 | 2.885 | 2 |
| 31.8 | 2.814 | 31 |
| 35.2 | 2.550 | 9 |
| 36.2 | 2.481 | 5 |
| 37.3 | 2.411 | 3 |
| 37.8 | 2.380 | 1 |
| 38.2 | 2.356 | 3 |
| 39.4 | 2.287 | 4 |
| 39.7 | 2.270 | <1 |
| 40.3 | 2.238 | 3 |
| 43.2 | 2.094 | <1 |
| 44.1 | 2.053 | <1 |
| 45.3 | 2.002 | 1 |
| 46.2 | 1.965 | <1 |
| 46.8 | 1.941 | 4 |
| 47.5 | 1.914 | 2 |
| 48.5 | 1.877 | <1 |
| 48.7 | 1.870 | 3 |
| 49.1 | 1.855 | 1 |
| 50.9 | 1.794 | 1 |
| 51.7 | 1.768 | 6 |
| 55.5 | 1.656 | 2 |

*Contains peak from another phase

The species SAPO-31 as referred to herein is a silicoaluminophosphate having a three-dimensional microporous crystal framework structure of $PO_2^+$, $AlO_2^-$ and $SiO_2$ tetrahedral units, and whose essential empirical chemical composition on an anhydrous basis is:

$$mR{:}(Si_xAl_yP_z)O_2$$

wherein R represents at least one organic templating agent present in the intracrystalline pore system; "m" represents the moles of "R" present per mole of $(Si_xAl_yP_z)O_2$ and has a value of from zero to 0.3; "x", "y" and "z" represent respectively, the mole fractions of silicon, aluminum and phosphorus present in the oxide moiety, said mole fractions being within the compositional area bounded by points A, B, C, D and E on the ternary diagram which is FIG. 1, or preferably within the area bounded by points a, b, c, d and e on the ternary diagram which is FIG. 2, said silicoaluminophosphate having a characteristic X-ray powder diffraction pattern which contains at least the d-spacings set forth below in Table XXIII. In the form as synthesized in accordance with the process of this invention, "m" has a value of from 0.02 to 0.3.

TABLE XXIII

| 2θ | d | Relative Intensity |
|---|---|---|
| 8.5–8.6 | 10.40–10.28 | M-S |
| 20.2–20.3 | 4.40–4.37 | M |
| 21.9–22.1 | 4.06–4.02 | W-M |
| 22.6–22.7 | 3.93–3.92 | VS |
| 31.7–31.8 | 2.823–2.814 | W-M |

All of the as-synthesized SAPO-31 compositions for which X-ray powder diffraction data have presently been obtained have patterns which are within the generalized pattern of Table XXIII, below.

TABLE XXIV

| 2θ | d | 100 × I/I₀ |
|---|---|---|
| 6.1 | 14.5 | 0–1 |

TABLE XXIV-continued

| 2θ | d | 100 × I/I₀ |
|---|---|---|
| 8.5-8.6* | 10.40-10.28 | 60-72 |
| 9.5* | 9.31 | 7-14 |
| 13.2-13.3* | 6.71-6.66 | 1-4 |
| 14.7-14.8 | 6.03-5.99 | 1-2 |
| 15.7-15.8* | 5.64-5.61 | 1-8 |
| 17.05-17.1 | 5.20-5.19 | 2-4 |
| 18.3-18.4 | 4.85-4.82 | 2-3 |
| 20.2-20.3 | 4.40-4.37 | 44-55 |
| 21.1-21.2* | 4.21-4.19 | 6-28 |
| 21.9-22.1* | 4.06-4.02 | 32-38 |
| 22.6-22.7* | 3.93-3.92 | 100 |
| 23.3-23.35* | 3.818-3.810 | 2-20 |
| 25.1* | 3.548 | 3-4 |
| 25.65-25.75 | 3.473-3.460 | 2-3 |
| 26.5* | 3.363 | 1-4 |
| 27.9-28.0 | 3.198-3.187 | 8-10 |
| 28.7* | 3.110 | 0-2 |
| 29.7 | 3.008 | 4-5 |
| 31.7-31.8 | 2.823-2.814 | 15-18 |
| 32.9-33.0* | 2.722-2.714 | 0-3 |
| 35.1-35.2 | 2.557-2.550 | 5-8 |
| 36.0-36.1 | 2.495-2.488 | 1-2 |
| 37.2 | 2.417 | 1-2 |
| 37.9-38.1* | 2.374-2.362 | 2-4 |
| 39.3 | 2.292 | 2-3 |
| 43.0-43.1* | 2.103-2.100 | 1 |
| 44.8-45.2* | 2.023-2.006 | 1 |
| 46.6 | 1.949 | 1-2 |
| 47.4-47.5 | 1.918 | 1 |
| 48.6-48.7 | 1.873-1.870 | 2 |
| 50.7-50.8 | 1.801-1.797 | 1 |
| 51.6-51.7 | 1.771-1.768 | 2-3 |
| 55.4-55.5 | 1.658-1.656 | 1 |

*Possibly contains peak from minor impurity

EXAMPLE 54
(Preparation of SAPO-41)

(a) A reaction mixture was prepared by combining 9.22 grams of 85 wt. % orthophosphoric acid (H₃PO₄) and 5.78 grams of water, to which was added 5.52 grams of hydrated aluminum oxide, (a pseudo-boehmite phase, 74.2 wt. % Al₂O₃, 25.8 wt. % H₂O) and stirred until homogeneous. To this mixture was added a mixture of 1.04 grams of a fume silica (92.8 wt. % SiO₂, 7.2 wt. % H₂O) in 41.67 grams of an aqueous solution of 25.9 wt. % tetra-n-butylammonium hydroxide (TBAOH). This mixture was stirred until homogeneous and then another 41.67 grams of TBAOH was slowly added with stirring until a homogeneous mixture was obtained. The composition of the final reaction mixture in molar oxide ratios was:

$$(TBA)_2O:Al_2O_3:P_2O_5:0.4SiO_2:98.7H_2O$$

A portion of the reaction mixture was sealed in a stainless steel pressure vessel lined with an inert plastic material and heated in an oven at 200° C. at autogenous pressure for 144 hours. The solid reaction product was recovered by centrifuging and washing with water, and dried in air at room temperature. The product had an X-ray powder diffraction pattern characterized by the following data:

TABLE HH

| 2θ | d | 100 × I/I₀ |
|---|---|---|
| 6.7 | 13.19 | 24 |
| 9.6 | 9.21 | 25 |
| 13.6 | 6.51 | 28 |
| 18.2 | 4.87 | 10 |
| 20.5 | 4.33 | 10 |
| 21.1 | 4.21 | 100 |
| 22.1 | 4.02 | 82 |
| 22.8 | 3.90 | 43 |
| 23.1 | 3.85 | 30 |
| 25.3 | 3.52 | 20 |
| 25.7 | 3.47 | 28 |
| 29.3 | 3.048 | 23 |
| 31.4 | 2.848 | 10 |
| 33.1 | 2.706 | 7 |
| 37.6 | 2.392 | 15 |
| 38.1 | 2.362 | 7 |
| 39.6 | 2.276 | 5 |
| 43.0 | 2.103 | 8 |
| 49.1 | 1.855 | 8 |
| 51.5 | 1.774 | 8 |

By chemical analysis the composition of the SAPO-41 was found to be 5.2 wt. % C; 38.1 wt. % Al₂O₃; 41.1 wt. % P₂O₅; 7.1 wt. % SiO₂; and by difference, LOI was 13.7 wt. %; giving a product composition in terms of molar oxide ratios of:

$$0.036(TBA)_2O:1.0Al_2O_3:0.77P_2O_5:0.32SiO_2:1.0H_2O$$

which corresonds to the formula $$0.02TBA:(Si_{0.08}Al_{0.52}P_{0.40})O_2$$

(b) A portion of the above solid product was calcined in air at 600° C. for 2 hours and then at 700° C. for 1 hour. The calcined product had an X-ray powder diffraction pattern characterized by the following data:

TABLE JJ

| 2θ | d | 100 × I/I₀ |
|---|---|---|
| 6.7 | 13.19 | 17 |
| 9.7 | 9.12 | 33 |
| 13.6 | 6.51 | 27 |
| 18.4 | 4.82 | 10 |
| 20.5 | 4.33 | 6 |
| 21.3 | 4.17 | 100 |
| 22.3 | 3.99 | 62 |
| 22.8 | 3.90 | 38 |
| 23.0 | 3.87 | 36 |
| 25.4 | 3.52 | 25 |
| 25.7 | 3.466 | 23 |
| 28.1 | 3.175 | 4 |
| 29.4 | 3.038 | 19 |
| 31.4 | 2.849 | 10 |
| 33.2 | 2.698 | 10 |
| 36.7 | 2.449 | 4 |
| 37.9 | 2.374 | 10 |
| 38.4 | 2.344 | 4 |
| 39.7 | 2.270 | 4 |
| 43.3 | 2.089 | 6 |
| 51.5 | 1.774 | 2 |

(c) Adsorption capacities were measured on this calcined product of part (b) using a standard McBain-Bakr gravimetric adsorption apparatus. The following data were obtained on a sample activated at 350° C.

| | Kinetic Diameter, Å | Pressure Torr | Temp., °C. | Wt. % Adsorbed |
|---|---|---|---|---|
| O₂ | 3.46 | 100 | −183 | 9.3 |
| O₂ | 3.46 | 750 | −183 | 11.8 |
| Cyclohexane | 6.0 | 60 | 24 | 4.2 |
| Neopentane | 6.2 | 743 | 24 | 1.2 |
| H₂O | 2.65 | 4.6 | 24 | 10.4 |
| H₂O | 2.65 | 20.0 | 24 | 21.9 |

The pore size of the calcined product is between 6.0 and 6.2 A as shown by adsorption of cyclohexane, kinetic diameter of 6.0 A and negligible adsorption of neopentane, kinetic diameter of 6.2 A.

EDAX (energy dispersive analysis by X-ray) microprobe analysis, performed in conjunction with SEM (scanning electron microscope) study on crystals having a crystal morphology characteristic of SAPO-41 gives the following analysis based on relative peak heights:

|  | Rod | Agglomerate |
|---|---|---|
| Si | 0.09 | 0.11 |
| Al | 1.0 | 1.0 |
| P | 0.87 | 0.74 |

The species SAPO-41 as referred to herein is a silicoaluminophosphate having a three-dimensional microporous crystal framework structure of $PO_2^+$, $AlO_2^-$ and $SiO_2$ tetrahedral units, and whose essential empirical chemical composition on an anhydrous basis is:

$$mR:(Si_xAl_yP_z)O_2$$

wherein R represents at least one organic templating agent present in the intracrystalline pore system; "m" represents the moles of "R" present per mole of $(Si_xAl_yP_z)O_2$ and has a value of from zero to 0.3; "x", "y" and "z" represent respectively, the mole fractions of silicon, aluminum and phosphorus present in the oxide moiety, said mole fractions being within the compositional area bounded by points A, B, C, D and E on the ternary diagram which is FIG. 1, or preferably within the area bounded by points a, b, c, d and e on the ternary diagram which is FIG. 2, said silicoaluminophosphate having a characteristic X-ray powder diffraction pattern which contains at least the d-spacings set forth below in Table XXV. In the form as synthesized in accordance with the process of this invention, "m" has a value of from 0.02 to 0.3.

TABLE XXV

| 2θ | d | Relative Intensity |
|---|---|---|
| 13.6–13.8 | 6.51–6.42 | W–M |
| 20.5–20.6 | 4.33–4.31 | W–M |
| 21.1–21.3 | 4.21–4.17 | VS |
| 22.1–22.3 | 4.02–3.99 | M–S |
| 22.8–23.0 | 3.90–3.86 | M |
| 23.1–23.4 | 3.82–3.80 | W–M |
| 25.5–25.9 | 3.493–3.44 | W–M |

All of the as-synthesized SAPO-41 compositions for which X-ray powder diffraction data have presently been obtained have patterns which are within the generalized pattern of Table XXVI, below.

TABLE XXVI

| 2θ | d | 100 × I/I$_o$ |
|---|---|---|
| 6.7–6.8 | 13.19–12.99 | 15–24 |
| 9.6–9.7 | 9.21–9.11 | 12–25 |
| 13.6–13.8 | 6.51–6.42 | 10–28 |
| 18.2–18.3 | 4.87–4.85 | 8–10 |
| 20.5–20.6 | 4.33–4.31 | 10–32 |
| 21.1–21.3 | 4.21–4.17 | 100 |
| 22.1–22.3 | 4.02–3.99 | 45–82 |
| 22.8–23.0 | 3.90–3.87 | 43–58 |
| 23.1–23.4 | 3.82–3.80 | 20–30 |
| 25.2–25.5 | 3.53–3.49 | 8–20 |

TABLE XXVI-continued

| 2θ | d | 100 × I/I$_o$ |
|---|---|---|
| 25.5–25.9 | 3.493–3.44 | 12–28 |
| 29.3–29.5 | 3.048–3.028 | 17–23 |
| 31.4–31.6 | 2.849–2.831 | 5–10 |
| 33.1–33.3 | 2.706–2.690 | 5–7 |
| 37.6–37.9 | 2.392–2.374 | 10–15 |
| 38.1–38.3 | 2.362–2.350 | 7–10 |
| 39.6–39.8 | 2.276–2.265 | 2–5 |
| 42.8–43.0 | 2.113–2.103 | 5–8 |
| 49.0–49.3 | 1.859–1.848 | 1–8 |
| 51.5 | 1.774 | 0–8 |

The present SAPO compositions exhibit novel surface selectivity characteristics which render them useful as catalyst or catalyst bases in a number of hydrocarbon conversion and oxidative combustion reactions. They can be impregnated or otherwise loaded with catalytically active metals by methods well known in the art and used, for example, in fabricating catalysts compositions having silica or alumina bases.

Among the hydrocarbon conversion reactions catalyzed by SAPO compositions are cracking, hydrocracking, alkylation of both the aromatic and isoparaffin types, isomerization, including xylene isomerization, polymerization, reforming, hydrogenation, dehydrogenation, transalkylation, dealkylation and hydration.

Using SAPO catalysts compositions which contain a hydrogenation promotor such as platinum, palladium, tungsten, nickel or molybdenum, heavy petroleum residual stocks, cyclic stocks and other hydrocrackable charge stocks can be hydrocracked at temperatures in the range of 400° F. to 825° F. using molar ratios of hydrogen to hydrocarbon in the range of between 2 and 80, pressures between 10 and 3500 p.s.i.g., and a liquid hourly space velocity (LHSV) of from 0.1 to 20, preferably 1.0 to 10.

The SAPO catalyst compositions employed in hydrocracking are also suitable for use in reforming processes in which the hydrocarbon feedstocks contact the catalyst at temperatures of from about 700° F. to 1000° F., hydrogen pressures of from 100 to 500 p.s.i.g., LHSV values in the range of 0.1 to 10 and hydrogen to hydrocarbon molar ratios in the range of 1 to 20, preferably between 4 and 12.

These same catalysts, i.e., those containing hydrogenation promoters, are also useful in hydroisomerization processes in which feedstocks such as normal paraffins are converted to saturated branched-chain isomers. Hydroisomerization is carried out at a temperature of from about 200° F. to 600° F., preferably 300° F. to 550° F. with an LHSV value of from about 0.2 to 1.0. Hydrogen is supplied to the reactor in admixture with the hydrocarbon feedstock in molar proportions (H/Hc) of between 1 and 5.

At somewhat higher temperatures, i.e., from about 650° F. to 1000° F., preferably 850° F. to 950° F. and usually at somewhat lower pressures within the range of about 15 to 50 p.s.i.g., the same catalyst compositions are used to hydroisomerize normal paraffins. Preferably the paraffin feedstock comprises normal paraffins having a carbon number range of $C_7$–$C_{20}$. Contact time between the feedstock and the catalyst is generally relatively short to avoid undesirable side reactions such as olefin polymerization and paraffin cracking. LHSV values in the range of 0.1 to 10, preferably 1.0 to 6.0 are suitable.

The unique crystal structure of the present SAPO catalysts and their availability in most cases as as-synthesized compositions which have a total lack of alkali metal content, favor their use in the conversion of alkylaromatic compounds, particularly the catalytic disproportionation of toluene, xylene, trimethylbenzenes, tetramethylbenzenes and the like. In the disproportionation process isomerization and transalkylation can also occur. Group VIII noble metal adjuvants alone or in conjunction with Group VI-B metals such as tungsten, molybdenum and chromium are preferably included in the catalyst composition in amounts of from about 3 to 15 weight-% of the overall composition. Extraneous hydrogen can, but need not be present in the reaction zone which is maintained at a temperature of from about 400° to 750° F., pressures in the range of 100 to 2000 p.s.i.g. and LHSV values in the range of 0.1 to 15.

Catalytic cracking processes are preferably carried out with SAPO compositions using feedstocks such as gas oils, heavy naphthas, deasphalted crude oil residue etc. with gasoline being the principal desired product. Temperature conditions of 850° to 1100° F., LHSV values of 0.5 to 10 and pressure conditions of from about 0 to 50 p.s.i.g. are suitable.

Dehydrocyclization reactions employing paraffinic hydrocarbon feedstocks, preferably normal paraffins having more than 6 carbon atoms, to form benzene, xylenes, toluene and the like are carried out using essentially the same reaction conditions as for catalytic cracking. For these reactions it is preferred to use the SAPO catalyst in conjunction with a Group VII non-noble metal cation such as cobalt and nickel.

In catalytic dealkylation wherein it is desired to cleave paraffinic side chains from aromatic nuclei without substantially hydrogenating the ring structure, relatively high temperatures in the range of about 800° F.–1000° F. are employed at moderate hydrogen pressures of about 300–1000 p.s.i.g., other conditions being similar to those described above for catalytic hydrocracking. Preferred catalysts are of the same type described above in connection with catalytic dehydrocyclization. Particularly desirable dealkylation reactions contemplated herein include the conversion of methylnaphthalene to naphthalene and toluene and/or xylenes to benzene.

In catalytic hydrofining, the primary objective is to promote the selective hydrodecomposition of organic sulfur and/or nitrogen compounds in the feed, without substantially affecting hydrocarbon molecules therein. For this purpose it is preferred to employ the same general conditions described above for catalytic hydrocracking, and catalysts of the same general nature described in connection with dehydrocyclization operations. Feedstocks include gasoline fractions, kerosenes, jet fuel fractions, diesel fractions, light and heavy gas oils, deasphalted crude oil residua and the like any of which may contain up to about 5 weight-percent of sulfur and up to about 3 weight-percent of nitrogen.

Similar conditions can be employed to effect hydrofining, i.e., denitrogenation and desulfurization, of hydrocarbon feeds containing substantial proportions of organonitrogen and organosulfur compounds. It is generally recognized that the presence of substantial amounts of such constituents markedly inhibits the activity of catalysts of hydrocracking. Consequently, it is necessary to operate at more extreme conditions when it is desired to obtain the same degree of hydrocracking conversion per pass on a relatively nitrogenous feed than are required with a feed containing less organonitrogen compounds. Consequently, the conditions under which denitrogenation, desulfurization and/or hydrocracking can be most expeditiously accomplished in any given situation are necessarily determined in view of the characteristics of the feedstocks in particular the concentration of organonitrogen compounds in the feedstock. As a result of the effect of organonitrogen compounds on the hydrocracking activity of these compositions it is not at all unlikely that the conditions most suitable for denitrogenation of a given feedstock having a relatively high organonitrogen content with minimal hydrocracking, e.g., less than 20 volume percent of fresh feed per pass, might be the same as those preferred for hydrocracking another feedstock having a lower concentration of hydrocracking inhibiting constituents e.g., organonitrogen compounds. Consequently, it has become the practice in this art to establish the conditions under which a certain feed is to be contacted on the basis of preliminary screening tests with the specific catalyst and feedstock.

Isomerization reactions are carried out under conditions similar to those described above for reforming, using somewhat more acidic catalysts. Olefins are preferably isomerized at temperatures of 500° F.–900° F., while paraffins, naphthenes and alkyl aromatics are isomerized at temperatures of 700° F.–1000° F. Particularly desirable isomerization reactions contemplated herein include the conversion of n-heptane and/or n-octane to isoheptanes, iso-octanes, butane to iso-butane, methylcyclopentane to cyclohexane, meta-xylene and/or ortho-xylene to para-xylene, 1-butene to 2-butene and/or isobutene, n-hexene to isohexane, cyclohexane to methylcyclopentene etc. The preferred cation form is a combination of the SAPO with polyvalent metal compounds (such as sulfides) of metals of Group II-A, Group II-B and rare earth metals. For alkylation and dealkylation processes the SAPO compositions having pores of at least 5 A are preferred. When employed for dealkylation of alkyl aromatics, the temperature is usually at least 350° F. and ranges up to a temperature at which substantial cracking of the feedstock or conversion products occurs, generally up to about 700° F. The temperature is preferably at least 450° F. and not greater than the critical temperature of the compound undergoing dealkylation. Pressure conditions are applied to retain at least the aromatic feed in the liquid state. For alkylation the temperature can be as low as 250° F. but is preferably at least 350° F. In alkylation of benzene, toluene and xylene, the preferred alkylating agents are olefins such as ethylene and propylene.

The present silicoaluminophospahte compositions can be used in the same conventional molecular sieving processes as heretofore have been carried out using aluminosilicate or aluminophosphate molecular sieves. For use in these processes the SAPO compositions are preferably activated to remove any molecular species which may be present in the intracrystalline pore system as a result of synthesis or otherwise. It is sometimes necessary to thermally destroy organic species present in as-synthesized SAPO's since some are too large to be desorbed by conventional means.

As an indication of the catalytic cracking activity of the present class of novel silicoaluminosilicates, certain of the SAPO species were tested for n-butane cracking using a bench-scale apparatus. The reactor was a cylindrical quartz tube 254 mm. in length and 10.3 mm. I.D. In each test the reactor was loaded with particles of the test SAPO which were 20-40 mesh (U.S. std.) in size and in an amount of from 0.5 to 5 grams, the quantity being selected so that the conversion of n-butane was at least 5% and not more than 90% under the test conditions. Most of the SAPO samples had been previously calcined in air to remove organic materials from the pore system, and were activated in situ in the reactor in a flowing stream of helium at 500° C. for one hour. The feedstock was a helium-n-butane mixture containing 2 mole percent n-butane and was passed through the reactor at a rate of 50 cc./minute. Analysis of the feedstock and the reactor effluent were carried out using conventional gas chromatography techniques. The reactor effluent was analyzed after 10 minutes of on-stream operation. From the analytical data the pseudo-first-order rate constant ($k_A$) was calculated. Pertinent data is set forth in tabular form below.

| SAMPLE OF EX. NO. | SAPO SPECIES | AIR CALCINATION BEFORE TEST | $k_{(A)}$ |
|---|---|---|---|
| 13 | 5 | 1 hr. at 600° C. | 1.4 |
| 9(a) | 5 | 1 hr. at 600° C. | 7.4 |
| 15 | 11 | 1 hr. each at 500° C. and 600° C. | 0.5 |
| 26 | 17 | 4 hrs. at 550° C. | 0.5 |
| 51 | 31 | 7 hrs. at 550° C. | 0.2 |
| 37 | 34 | 1 hr. at 600° C. | 3.0 |
| 42 | 37 | none | 1.1 |
| 43 | 37 | none | 1.6 |
| 50 | 44 | 3.5 hrs. at 600° C. | 2.4 |

The SAPO compositions are useful as adsorbents and are capable of separating mixtures of molecular species both on the basis of molecular size (kinetic diameters) and degree of polarity of the involved molecules. In the case of selective adsorption based on molecular size, the SAPO adsorbent is chosen in view of the dimensions of its pores such that at least the smallest molecular specie of the mixture can enter the intracrystalline void space while at least the largest specie is excluded. Separations based on degree of polarity, the more hydrophilic SAPO species will preferentially adsorb the more polar molecular species of a mixture having different degrees of polarity even though both molecular species can enter the SAPO pore system.

We claim:

1. Microporous crystalline silicoaluminophosphates the pores of which are uniform and have nominal diameters of greater than about 3 Angstroms and whose essential empirical chemical composition in the as-synthesized and anhydrous form is

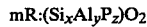

$$mR:(Si_xAl_yP_z)O_2$$

wherein "R" represents at least one organic templating agent present in the intracrystalline pore system; "m" has a value of from 0.02 to 0.3; "m" represents the moles of "R" present per mole of $(Si_xAl_yP_z)O_2$; "x", "y" and "z" represent the mole fractions of silicon, aluminum and phosphorus respectively, present as tetrahedral oxides, said mole fractions being such that they are within the pentagonal compositional area defined by points ABCD and E of the ternary diagram which is FIG. 1 of the drawings.

2. Microporous crystalline silicoaluminophosphates according to claim 1 wherein the mole fractions of silicon, aluminum and phosphorus are within the pentagonal compositional area defined by points a, b, c, d and e of the ternary diagram which is FIG. 2 of the drawings.

3. Crystalline silicoaluminophosphate according to claim 1 or claim 2 having a characteristic X-ray powder diffraction pattern which contains at least the d-spacings set forth in Table I.

4. Crystalline silicoaluminophosphate according to claim 1 or claim 2 having a characteristic X-ray powder diffraction pattern which contains at least the d-spacings set forth in Table III.

5. Crystalline silicoaluminophosphate according to claim 1 or claim 2 having a characteristic X-ray powder diffraction pattern which contains at least the d-spacings set forth in Table V.

6. Crystalline silicoaluminophosphate according to claim 1 or claim 2 having a characteristic X-ray powder diffraction pattern which contains at least the d-spacings set forth in Table VII.

7. Crystalline silicoaluminophosphate according to claim 1 or claim 2 having a characteristic X-ray powder diffraction pattern which contains at least the d-spacings set forth in Table IX.

8. Crystalline silicoaluminophosphate according to claim 1 or claim 2 having a characteristic X-ray powder diffraction pattern which contains at least the d-spacings set forth in Table XI.

9. Crystalline silicoaluminophosphate according to claim 1 or claim 2 having a characteristic X-ray powder diffraction pattern which contains at least the d-spacings set forth in Table XIII.

10. Crystalline silicoaluminophosphate according to claim 1 or claim 2 having a characteristic X-ray powder diffraction pattern which contains at least the d-spacings set forth in Table XV.

11. Crystalline silicoaluminophosphate according to claim 1 or claim 2 having a characteristic X-ray powder diffraction pattern which contains at least the d-spacings set forth in Table XVII.

12. Crystalline silicoaluminophosphate according to claim 1 or claim 2 having a characteristic X-ray powder diffraction pattern which contains at least the d-spacings set forth in Table XIX.

13. Crystalline silicoaluminophosphate according to claim 1 or claim 2 having a characteristic X-ray powder diffraction pattern which contains at least the d-spacings set forth in Table XXI.

14. Crystalline silicoaluminophosphate according to claim 1 or claim 2 having a characteristic X-ray powder diffraction pattern which contains at least the d-spacings set forth in Table XXIII.

15. Crystalline silicoaluminophosphate according to claim 1 or claim 2 having a characteristic X-ray powder diffraction pattern which contains at least the d-spacings set forth in Table XXV.

16. Crystalline silicoaluminophosphate prepared by calcining the compositions of claim 1 or claim 2 or claim 3 or claim 4 or claim 5 or claim 6 or claim 7 or claim 8 or claim 9 or claim 10 or claim 11 or claim 12 or claim 13 or claim 14 or claim 15 at a temperature sufficiently high to remove at least some of the organic templating agent present in the intracrystalline pore system.

17. Silicoaluminophosphate material having a three-dimensional microporous framework structure of $PO_2^+$, $AlO_2^-$ and $SiO_2$ tetrahedral units, and whose essential empirical chemical composition on an anhydrous basis is:

$$mR:(Si_xAl_yP_z)O_2$$

wherein R represents at least one organic templating agent present in the intracrystalline pore system; "m" represents the moles of "R" present per mole of $(Si_xAl_yP_z)O_2$ and has a value of from zero to 0.3; "x", "y" and "z" represent respectively, the mole fractions of silicon, aluminum and phosphorus present in the oxide moiety, said mole fractions being within the compositional area bounded by points A, B, C, D and E on the ternary diagram which is FIG. 1, said silicoaluminophosphate having a characteristic X-ray powder diffraction pattern which contains at least the d-spacings set forth below in any one of Tables I, III, V, VII, IX, XIII, XVII, XXI, XXIII or XXV.

18. Composition according to claim 17 wherein the mole fractions of silicon, aluminum and phosphorus are within the pentagonal compositional area defined by points a, b, c, d and e of the ternary diagram which is FIG. 2 of the drawings.

19. Composition according to claim 17 or claim 16 which has the characteristic X-ray powder diffraction pattern containing at least the d-spacings of Table I.

20. Composition according to claim 17 or claim 18 which has the characteristic X-ray powder diffraction pattern containing at least the d-spacings of Table III.

21. Composition according to claim 17 or claim 18 which has the characteristic X-ray powder diffraction pattern containing at least the d-spacings of Table V.

22. Composition according to claim 17 or claim 18 which has the characteristic X-ray powder diffraction pattern containing at least the d-spacings of Table VII.

23. Composition according to claim 17 or claim 18 which has the characteristic X-ray powder diffraction powder containing at least the d-spacings of Table IX.

24. Composition according to claim 17 or claim 18 which has the characteristic X-ray powder diffraction pattern containing at least the d-spacings of Table XIII.

25. Composition according to claim 17 or claim 18 which has the characteristic X-ray powder diffraction pattern containing at least the d-spacings of Table XVII.

26. Composition according to claim 17 or claim 18 which has the characteristic X-ray powder diffraction pattern containing at least the d-spacings of Table XXI.

27. Composition according to claim 17 or claim 18 which has the characteristic X-ray powder diffraction pattern containing at least the d-spacings of Table XXIII.

28. Composition according to claim 17 or claim 18 which has the characteristic X-ray powder diffraction pattern containing at least the d-spacings of Table XXV.

29. Composition according to claim 17 or claim 18 wherein in the formula $$mR:(Si_xAl_yP_z)O_2$$

"m" has a value of zero, said composition having an X-ray powder diffraction pattern essentially as set forth in any one of Tables D, J, N, U, BB, EE, FF, and JJ.

30. Process for preparing a crystalline silicoaluminophosphate of claim 1 which comprises forming a reaction mixture containing reactive sources of $SiO_2$, $Al_2O_3$, and $P_2O_5$ and an organic templating agent, said reaction mixture having a composition expressed in terms of molar oxide ratios of:

$$aR_2O:(Si_xAl_yP_z)O_2:bH_2O$$

wherein "R" is an organic templating agent; "a" has a value large enough to constitute an effective amount of "R" and is within the range of greater than 0 to 3; "b" has a value of from zero to 500; "x", "y" and "z" represent the mole fractions, respectively, of silicon, aluminum and phosphorus in the $(Si_xAl_yP_z)O_2$ constituent and each has a value of at least 0.01 and crystallizing the reaction mixture thus formed at a temperature of at least 100° C. until crystals of the silicoaluminophosphate are formed.

31. Process according to claim 30 wherein "b" has a value of from 2 to 30.

32. Process according to claim 30 or claim 1 wherein the source of phosphorus in the reaction mixture is orthophosphoric acid.

33. Process according to claim 30 or claim 1 wherein the source of aluminum in the reaction mixture is at least one compound selected from the group consisting of pseudo-boehmite and aluminum alkoxide, and the source of phosphorus is orthophosphoric acid.

34. Process according to claim 33 wherein the aluminum alkoxide is aluminum isopropoxide.

35. Process according to claim 30 or claim 1 wherein the organic templating agent is a quaternary ammonium or quaternary phosphonium compound having the formula $$R_4X^+$$

wherein X is nitrogen or phosphorus and each R is an alkyl or aryl group containing from 1 to 8 carbon atoms.

36. Process according to claim 35 wherein the organic templating agent is an amine.

37. Process according to claim 35 wherein the templating agent is selected from the group consisting of tetrapropylammonium ion; tetraethylammonium ion; tripropylamine; triethylamine; triethanolamine; piperidine; cyclohexylamine; 2-methyl pyridine; N,N-dimethylbenzylamine; N,N-diethylethanolamine; dicyclohexylamine; N,N-dimethylethanolamine; choline; N,N-dimethylpiperazine; 1,4-diazabicyclo-(2,2,2)octane; N-methyldiethanolamine; N-methylethanolamine; N-methylpiperidine; 3-methylpiperidine; N-methylcyclohexylamine; 3-methylpyridine; 4-methylpyridine; quinuclidine; N,N'-dimethyl-1,4-diazabicyclo(2,2,2)octane ion; tetramethylammonium ion; tetrabutylammonium ion; tetrapentylammonium ion; di-n-butylamine; neopentylamine; di-n-pentylamine; isopropylamine; t-butylamine; ethylenediamine and 2-imidazolidone; di-n-propylamine; and a polymeric quaternary ammonium salt $[(C_{14}H_{32}N_2)]_x^+$ wherein x is a value of at least 2.

38. Process for preparing a crystalline silicoaluminophosphate of claim 1 which comprises forming a reaction mixture having a composition expressed in terms of molar oxide rations of:

$$aR_2O:bM_2O:(Si_xAl_yP_z)O_2:cH_2O$$

wherein "R" is an organic templating agent; "a" has a value great enough to constitute an effective concentration of "R" and is within the range >0 to 3; "M" is an alkali metal; "b" has a value of zero to 2.5; "c" has a value of from zero to 500; "x", "y" and "z" represent the mole fractions, respectively, of silicon, aluminum and phosphorus in the $(Si_xAl_yP_z)O_2$ constituent, and each have a value of at least 0.01 and being within the quadrilateral compositional area defined by points f, g, h and i which is FIG. 3 of the drawings, the said points f, g, h and i representing the following values for "x", "y" and "z":

| Point | Mole Fraction | | |
|---|---|---|---|
| | x | y | z |
| f | 0.01 | 0.98 | 0.01 |
| g | 0.01 | 0.01 | 0.98 |
| h | 0.32 | 0.24 | 0.44 |
| i | 0.98 | 0.01 | 0.01; | said reaction mixture having been formed by combining at least a portion of each of the aluminum and phosphorus sources in the substantial absence of the silicon source and thereafter combining the resulting mixture with the remaining constituents to form the complete reaction mixture, and thereafter crystallizing said complete reaction mixture at a temperature of from 100° C. to about 250° C. in a sealed reactor until crystals of the silicoaluminophosphate are formed.

* * * * *